United States Patent
Allen et al.

(10) Patent No.: US 8,513,284 B2
(45) Date of Patent: Aug. 20, 2013

(54) FUSED PYRIDINE AND PYRAZINE DERIVATIVES AS KINASE INHIBITORS

(75) Inventors: Daniel Rees Allen, Saffron Walden (GB); Julien Alistair Brown, Slough (GB); Roland Burli, Saffron Walden (GB); Alan Findlay Haughan, Saffron Walden (GB); Jonathan David MacDonald, Leeds (GB); Elizabeth Anne Saville-Stones, Saffron Walden (GB); Andrew Sharpe, Saffron Walden (GB)

(73) Assignee: UCB Pharma, S.A., Brussels (BE)

( * ) Notice: Subject to any disclaimer, the term of this patent is extended or adjusted under 35 U.S.C. 154(b) by 0 days.

(21) Appl. No.: 13/201,160

(22) PCT Filed: Feb. 11, 2010

(86) PCT No.: PCT/GB2010/000243
§ 371 (c)(1),
(2), (4) Date: Dec. 9, 2011

(87) PCT Pub. No.: WO2010/092340
PCT Pub. Date: Aug. 19, 2010

(65) Prior Publication Data
US 2012/0077815 A1    Mar. 29, 2012

(30) Foreign Application Priority Data

Feb. 13, 2009 (GB) .................................. 0902450.6
Aug. 19, 2009 (GB) .................................. 0914533.5

(51) Int. Cl.
*A61K 31/47* (2006.01)
(52) U.S. Cl.
USPC .......................................... 514/313; 546/159
(58) Field of Classification Search
USPC .......................................... 514/313; 546/159
See application file for complete search history.

(56) References Cited

U.S. PATENT DOCUMENTS

| 2005/0014771 A1 | 1/2005 | Hayakawa et al. |
| 2006/0178514 A1 | 8/2006 | Baruah et al. |

FOREIGN PATENT DOCUMENTS

| WO | 2006/073973 A2 | 7/2006 |
| WO | 2007/088999 A1 | 8/2007 |
| WO | 2007/092854 A2 | 8/2007 |
| WO | 2008/118454 A2 | 10/2008 |
| WO | 2008/118455 A1 | 10/2008 |
| WO | 2008/118468 A1 | 10/2008 |
| WO | 2009/081105 A2 | 7/2009 |
| WO | 2009/097278 A1 | 8/2009 |
| WO | 2010/027097 A1 | 3/2010 |
| WO | WO 2010/036380 | * 4/2010 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Singh, V., et al, "Reductive-Cyclization-Mediated Synthesis of Fused Polycyclic Quinolines from Baylis-Hillman Adducts of Acrylonitrile: Scope and Limitations," European Journal of Organic Chemistry, No. 20, 2009, pp. 3454-3466.
Ahuja, J.R., et al, "A new short synthesis of 3-3'-methylenebis[coumarins] and 3,3-methylenebis[2-diethylaminoquinolines]", Synthetic Communications, vol. 17, No. 16, 1987, pp. 1951-1958.

* cited by examiner

*Primary Examiner* — Douglas M Willis
(74) *Attorney, Agent, or Firm* — McDonnell Boehnen Hulbert & Berghoff LLP

(57) ABSTRACT

A series of amino-substituted fused pyridine and pyrazine derivatives, in particular amino-substituted quinoline and quinoxaline derivatives, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions.

8 Claims, No Drawings

FUSED PYRIDINE AND PYRAZINE DERIVATIVES AS KINASE INHIBITORS

BACKGROUND OF THE INVENTION

This application is a US national phase of International Application No. PCT/GB2010/000243 filed on Feb. 11, 2010, which claims the benefit of Great Britain patent application 0902450.6, filed Feb. 13, 2009, and Great Britain patent application 0914533.5, filed Aug. 19, 2009, the disclosures of which are incorporated herein by reference in their entirety.

The present invention relates to a class of fused pyridine and pyrazine derivatives, and to their use in therapy. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2008/118454, WO 2008/118455 and WO 2008/118468 describe various series of quinoline and quinoxaline derivatives that are structurally related to each other and are stated to be useful to inhibit the biological activity of human PI3Kδ and to be of use in treating PI3K-mediated conditions or disorders.

Copending international patent application PCT/GB2008/004171, published on 2 Jul. 2009 as WO 2009/081105, and copending international patent application PCT/GB2009/002504 (claiming priority from United Kingdom patent application 0819593.5) describe separate classes of fused bicyclic heteroaryl derivatives as selective inhibitors of PI3K enzymes that are of benefit in the treatment of adverse inflammatory, autoimmune, cardiovascular, neurodegenerative, metabolic, oncological, nociceptive and ophthalmic conditions.

None of the prior art available to date, however, discloses or suggests the precise structural class of fused pyridine and pyrazine derivatives as provided by the present invention. In particular, none of the available prior art publications provides for substitution by a non-cyclic amine moiety on the pyridine or pyrazine ring.

DESCRIPTION OF THE INVENTION

The compounds of the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides a compound of formula (I) or an N-oxide thereof, or a pharmaceutically acceptable salt or solvate thereof:

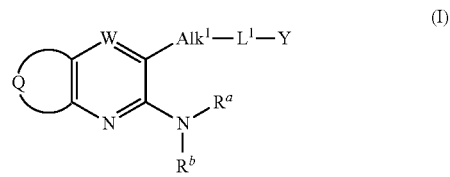

(I)

wherein

Q represents the residue of an optionally substituted phenyl ring; or an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl and triazolyl; or an optionally substituted six-membered heteroaromatic ring selected from pyridinyl, pyridazinyl, pyrimidinyl, pyrazinyl and triazinyl;

W represents C—$R^1$ or N;

$Alk^1$ represents an optionally substituted straight or branched $C_{1-3}$ alkylene chain;

$L^1$ represents oxygen, sulfur, N—$R^2$ or a covalent bond;

Y represents an optionally substituted mono- or bicyclic heteroaryl group containing at least one nitrogen atom;

$R^1$ represents hydrogen, halogen, $C_{1-6}$ alkyl or $C_{1-6}$ alkoxy;

$R^2$ represents hydrogen or $C_{1-6}$ alkyl;

$R^a$ represents hydrogen or trifluoromethyl; or $C_{1-6}$ alkyl, $C_{2-6}$ alkenyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and $R^b$ represents hydrogen, $C_{1-6}$ alkyl or $C_{3-7}$ cycloalkyl.

The present invention also provides a compound of formula (I) as depicted above or an N-oxide thereof, or a pharmaceutically acceptable salt or solvate thereof, wherein $R^a$ represents trifluoromethyl; or $C_{1-6}$ alkyl, $C_{2-6}$ alkenyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; and Q, W, $Alk^1$, $L^1$, Y, $R^1$, $R^2$ and $R^b$ are as defined above.

The present invention further provides a compound of formula (I) as depicted above or an N-oxide thereof, or a pharmaceutically acceptable salt or solvate thereof, wherein $R^a$ represents trifluoromethyl; or $C_{1-6}$ alkyl, $C_{3-7}$ cycloalkyl, $C_{3-7}$ cycloalkyl-($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and Q, W, $Alk^1$, $L^1$, Y, $R^1$, $R^2$ and $R^b$ are as defined above.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-3}$ alkylene chain" refers to a divalent straight or branched alkylene chain containing 1 to 3 carbon atoms. Typical examples include methylene, ethylene, methylmethylene, ethylmethylene and dimethylmethylene.

Suitable alkenyl groups include straight-chained and branched $C_{2-6}$ alkenyl groups. Typical examples include vinyl, allyl and dimethylallyl groups.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, tetrahydrothienyl, pyrrolidinyl, indolinyl, thiazolidinyl, imidazolidinyl, tetrahydropyranyl, chromanyl, dioxanyl, piperidinyl, 1,2,3,4-tetrahydroquinolinyl, 1,2,3,4-tetrahydroisoquinolinyl, homopiperidinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, thienopyrimidinyl (including thieno[2,3-d]pyrimidinyl), pyrrolyl, indolyl, pyrrolopyridinyl (including pyrrolo[2,3-b]pyridinyl and pyrrolo[3,2-c]pyridinyl), pyrrolotriazinyl (including pyrrolo[2,1-f][1,2,4]triazinyl), pyrazolyl, indazolyl, pyrazolopyridinyl (including pyrazolo[1,5-a]pyridinyl), pyrazolopyrimidinyl (including pyrazolo[1,5-a]pyrimidinyl and pyrazolo[3,4-d]pyrimidinyl), pyrazolotriazinyl (including pyrazolo[1,5-a][1,3,5]triazinyl), oxazolyl, benzoxazolyl, isoxazolyl, thiazolyl, benzothiazolyl, isothiazolyl, imidazolyl, benzimidazolyl, imidazopyridinyl (including imidazo[1,2-a]pyridinyl and imidazo[4,5-b]pyridinyl), purinyl, imidazo[1,2-a]pyrimidinyl, imidazopyrazinyl (including imidazo[1,2-a]pyrazinyl), oxadiazolyl, thiadiazolyl, triazolyl, triazolopyrimidinyl (including [1,2,4]triazolo[1,5-a]pyrimidinyl), benzotriazolyl, tetrazolyl, pyridinyl, quinolinyl, isoquinolinyl, naphthyridinyl, pyridopyrimidinyl (including pyrido[3,2-d]pyrimidinyl), pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C{=}O$)$\leftrightarrow$ enol ($CH{=}CHOH$) tautomers or amide ($NHC{=}O$)$\leftrightarrow$ hydroxyimine ($N{=}COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

Specific sub-classes of compounds in accordance with the present invention are represented by the compounds of formula (IA) and (IB):

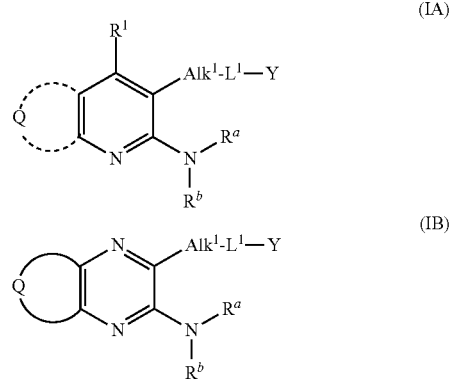

wherein Q, $Alk^1$, $L^1$, Y, $R^1$, $R^a$ and $R^b$ are as defined above.

In the compounds of formula (I), the moiety Q is defined as representing the residue of an optionally substituted phenyl ring, or of an optionally substituted five-membered or six-membered heteroaromatic ring as specified above. From this it is to be understood that the variable Q, when taken together with the two carbon atoms of the pyridine or pyrazine ring to which the Q-containing ring is fused, represents an optionally substituted phenyl ring, or an optionally substituted five-membered or six-membered heteroaromatic ring as specified above.

In one embodiment, the moiety Q in the compounds of formula (I) above represents the residue of an optionally substituted phenyl ring. In another embodiment, the moiety Q in the compounds of formula (I) above represents the residue of an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl. In a further embodiment, the moiety Q in the compounds of formula (I) above represents the residue of an optionally substituted six-membered heteroaromatic ring selected from pyridinyl, pyridazinyl, pyrimidinyl, pyrazinyl and triazinyl.

Suitably, the moiety Q represents the residue of a phenyl ring, which may be optionally substituted by one or two substitutents. In one embodiment, the moiety Q represents the residue of an unsubstituted phenyl ring. In another embodiment, the moiety Q represents the residue of a substituted phenyl ring. In one aspect of that embodiment, the moiety Q represents the residue of a monosubstituted phenyl ring. In another aspect of that embodiment, the moiety Q represents the residue of a disubstituted phenyl ring.

The ring of which the moiety Q is the residue may be unsubstituted, or may suitably be substituted, where possible, by one more, typically by one or two, substituents. In one embodiment, this ring is unsubstituted. In another embodiment, this ring is monosubstituted. In a further embodiment, this ring is disubstituted. Examples of typical substituents on the ring of which the moiety Q is the residue include $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$)alkylamino, halogen, cyano and trifluoromethyl.

Typically, the ring of which the moiety Q is the residue may optionally be substituted by $C_{1-6}$ alkyl or halogen.

Suitably, the ring of which the moiety Q is the residue may optionally be substituted by $C_{1-6}$ alkyl, especially methyl.

Suitably, the ring of which the moiety Q is the residue may optionally be substituted by halogen, especially fluoro or chloro. In one embodiment, the ring of which the moiety Q is the residue is optionally substituted by fluoro. In another embodiment, the ring of which the moiety Q is the residue is optionally substituted by chloro.

In one embodiment, W represents C—$R^1$. In another embodiment, W represents N.

Typical values of $Alk^1$ include methylene (—$CH_2$—), (methyl)methylene, ethylene (—$CH_2CH_2$—), (ethyl)methylene, (dimethyl)methylene, (methyl)ethylene and (dimethyl)ethylene, any of which chains may be optionally substituted by one or more substituents. Suitably, such chains are unsubstituted, monosubstituted or disubstituted. Preferably, such chains are unsubstituted or monosubstituted. In one embodiment, such chains are unsubstituted. In another embodiment, such chains are monosubstituted.

Examples of suitable substituents on the alkylene chain represented by $Alk^1$ include trifluoromethyl, aryl, oxo, hydroxy, $C_{1-6}$ alkoxy, $C_{2-6}$ alkoxycarbonyl($C_{1-6}$)alkoxy, aminocarbonyl($C_{1-6}$)alkoxy, trifluoromethoxy, aminocarbonyl, $C_{1-6}$ alkylaminocarbonyl and di($C_{1-6}$)alkylaminocarbonyl.

Examples of particular substituents on the alkylene chain represented by $Alk^1$ include trifluoromethyl, phenyl, oxo, hydroxy, ethoxy, ethoxycarbonylmethoxy, aminocarbonylmethoxy, trifluoromethoxy, aminocarbonyl, methylaminocarbonyl and dimethylaminocarbonyl.

Typically, $Alk^1$ represents methylene or (methyl)methylene.

A particular value of $Alk^1$ is (methyl)methylene, i.e. —CH($CH_3$)—. Another value of $Alk^1$ is methylene, i.e. —$CH_2$—.

In one embodiment, $L^1$ represents oxygen. In another embodiment, $L^1$ represents sulfur. In a further embodiment, $L^1$ represents N—$R^2$. In a still further embodiment, $L^1$ represents a covalent bond.

The expression "mono- or bicyclic heteroaryl group containing at least one nitrogen atom" in relation to the group Y refers in particular to a mono- or bicyclic aromatic ring system containing one, two, three or four heteroatoms selected from oxygen, sulfur and nitrogen atoms, with at least one of the heteroatoms being nitrogen. The ring Y may be linked to the group $L^1$ through any available carbon or nitrogen atom. Suitable examples of Y include pyrrolyl, pyridinyl, indolyl, quinolinyl, isoquinolinyl, imidazolyl, pyrazolyl, triazolyl, pyridazinyl, pyrimidinyl, pyrazinyl, triazinyl, indazolyl, benzimidazolyl, furopyridinyl, thienopyridinyl, benzoxazolyl, benzothiazolyl, cinnolinyl, phthalazinyl, quinazolinyl, quinoxalinyl, imidazopyridinyl, pyrazolopyridinyl, purinyl, pyrazolopyrimidinyl, pyrrolopyrimidinyl, triazolopyrimidinyl, pyridopyrimidinyl, pyridopyrazinyl, pyridopyridazinyl, naphthyridinyl and pteridinyl, any of which groups may be optionally substituted by one or more substituents. An additional example of Y is optionally substituted pyrazolotriazinyl. Further examples of Y include thieno-pyrimidinyl and pyrrolotriazinyl, either of which groups may be optionally substituted by one or more substituents.

Typically, Y may represent pyrrolyl, pyridin-2-yl, pyridin-3-yl, indolyl, isoquinolinyl, imidazolyl, pyrazolyl, triazolyl, pyridazinyl, pyrimidin-2-yl, pyrimidin-5-yl, pyrazinyl, triazinyl, indazolyl, furopyridinyl, thienopyridinyl, benzoxazolyl, benzothiazolyl, cinnolinyl, phthalazinyl, quinazolinyl, purin-1-yl, purin-2-yl, purin-3-yl, 7H-purin-6-yl, 9H-purin-6-yl, purin-7-yl, purin-8-yl, pyrazolo[3,4-d]pyrimidin-4-yl, triazolopyrimidinyl, pyridopyrimidin-4-yl, pyridopyrazinyl, pyridopyridazinyl, naphthyridinyl or pteridinyl, any of which groups may be optionally substituted by one or more substituents. Furthermore, Y may represent optionally substituted pyrazolotriazinyl. In addition, Y may represent pyrimidin-4-yl, pyrazolo[1,5-a]pyrimidinyl, thieno-pyrimidinyl or pyrrolotriazinyl, any of which groups may be optionally substituted by one or more substituents.

Selected values of Y include thienopyrimidinyl (especially thieno[2,3-d]pyrimidin-4-yl), pyrrolotriazinyl (especially pyrrolo[2,1-f][1,2,4]triazin-4-yl), pyrazolopyrimidinyl (especially pyrazolo[1,5-a]pyrimidin-7-yl and pyrazolo[3,4-d]pyrimidin-4-yl), pyrazolotriazinyl (especially pyrazolo[1,5-a][1,3,5]triazin-2-yl and pyrazolo[1,5-a][1,3,5]triazin-4-yl), purinyl (especially 9H-purin-6-yl), triazolopyrimidinyl (especially [1,2,4]triazolo[1,5-a]pyrimidin-7-yl), pyridopyrimidinyl (especially pyrido[3,2-d]pyrimidin-4-yl), pyrimidinyl (especially pyrimidin-2-yl and pyrimidin-4-yl) and triazinyl (especially [1,3,5]triazin-2-yl), any of which groups may be optionally substituted by one or more substituents.

Typical values of Y include triazinyl, purinyl (especially 9H-purin-6-yl), pyrazolopyrimidinyl (especially pyrazolo[3,4-d]pyrimidin-4-yl) and pyrazolotriazinyl (especially pyrazolo[1,5-a][1,3,5]triazin-4-yl), any of which groups may be optionally substituted by one or more substituents.

Particular values of Y include purinyl (especially 9H-purin-6-yl) and pyrazolopyrimidinyl (especially pyrazolo[3,4-d]pyrimidin-4-yl), either of which groups may be optionally substituted by one or more substituents.

Examples of optional substituents which may be present on the group Y include one, two or three substituents independently selected from halogen, cyano, nitro, oxo, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on the group Y include halogen, cyano, $C_{1-6}$ alkyl, $C_{1-6}$ alkylthio, $C_{1-6}$ alkylsulphonyl, amino and $C_{1-6}$ alkylamino.

Illustrative examples of optional substituents on the group Y include $C_{1-6}$ alkyl, $C_{1-6}$ alkylthio, $C_{1-6}$ alkylsulphonyl and amino.

Typical examples of optional substituents on the group Y include $C_{1-6}$ alkyl and amino.

Examples of particular substituents on the group Y include fluoro, chloro, bromo, cyano, nitro, oxo, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methoxycarbonylamino, methylsulfonylamino, formyl, acetyl, cyclopropylcarbonyl, azetidinylcarbonyl, N-methylazetidinylcarbonyl, pyrrolidinylcarbonyl, N-methylpyrrolidinylcarbonyl, piperidinylcarbonyl, N-methylpiperidinylcarbonyl, piperazinylcarbonyl, N-methylpiperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Selected examples of particular substituents on the group Y include fluoro, cyano, methyl, methylthio, methylsulphonyl, amino and methylamino.

Illustrative examples of particular substituents on the group Y include methyl, methylthio, methylsulphonyl and amino.

Typical examples of particular substituents on the group Y include amino and methyl.

In one embodiment, Y represents optionally substituted purinyl. In one aspect of that embodiment, Y represents unsubstituted purinyl, especially 9H-purin-6-yl. In another aspect of that embodiment, Y represents substituted purinyl, including halopurinyl, especially 2-fluoro-9H-purin-6-yl; and aminopurinyl, especially 2-amino-9H-purin-6-yl.

In another embodiment, Y represents optionally substituted pyrazolopyrimidinyl. In one aspect of that embodiment, Y represents pyrazolo[1,5-a]pyrimidin-4-yl. In another aspect of that embodiment, Y represents pyrazolo[3,4-d]pyrimidin-4-yl. In a further aspect of that embodiment, Y represents pyrazolopyrimidinyl substituted by $C_{1-6}$ alkyl, especially 1-methyl-1H-pyrazolo[3,4-d]pyrimidin-4-yl.

In another embodiment, Y represents optionally substituted triazinyl. In one aspect of that embodiment, Y represents 4-amino-[1,3,5]triazin-2-yl. In another aspect of that embodiment, Y represents 4-(methylamino)-[1,3,5]triazin-2-yl. In a further aspect of that embodiment, Y represents 4-amino-6-methyl-[1,3,5]triazin-2-yl.

In another embodiment, Y represents optionally substituted pyrazolotriazinyl. In one aspect of that embodiment, Y represents pyrazolo[1,5-a][1,3,5]triazin-4-yl. In another aspect of that embodiment, Y represents 2-(methylthio)pyrazolo[1,5-a][1,3,5]-triazin-4-yl. In a further aspect of that embodiment, Y represents 2-(methylsulphonyl)-pyrazolo[1,5-a][1,3,5]triazin-4-yl. In a still further aspect of that embodiment, Y represents 4-aminopyrazolo[1,5-a][1,3,5]triazin-2-yl.

In another embodiment, Y represents optionally substituted thienopyrimidinyl, especially thieno[2,3-d]pyrimidin-4-yl.

In another embodiment, Y represents optionally substituted pyrrolotriazinyl, especially pyrrolo[2,1-f][1,2,4]triazin-4-yl.

In another embodiment, Y represents optionally substituted triazolopyrimidinyl. In one aspect of that embodiment, Y represents triazolopyrimidinyl substituted by $C_{1-6}$ alkyl, especially 5-methyl-[1,2,4]triazolo[1,5-a]pyrimidin-7-yl.

In another embodiment, Y represents optionally substituted pyridopyrimidinyl, especially pyrido[3,2-d]pyrimidin-4-yl.

In another embodiment, Y represents optionally substituted pyrimidinyl. In one aspect of that embodiment, Y represents optionally substituted pyrimidin-2-yl, especially 4-amino-5-cyanopyrimidin-2-yl. In another aspect of that embodiment, Y represents optionally substituted pyrimidin-4-yl, especially 2-aminopyrimidin-4-yl and 2-amino-5-cyanopyrimidin-4-yl.

Typically, $R^1$ represents hydrogen or $C_{1-6}$ alkyl.

In one embodiment, $R^1$ represents hydrogen. In another embodiment, $R^1$ represents halogen, particularly fluoro or chloro. In one aspect of that embodiment, $R^1$ represents fluoro. In another aspect of that embodiment, $R^1$ represents chloro. In a further embodiment, $R^1$ represents $C_{1-6}$ alkyl, especially methyl. In an additional embodiment, $R^1$ represents $C_{1-6}$ alkoxy, especially methoxy.

Suitable values of the group $R^1$ include hydrogen, fluoro, chloro, bromo, methyl and methoxy. Suitably, $R^1$ represents hydrogen or methyl. Typically, $R^1$ represents hydrogen.

In one embodiment, $R^2$ represents hydrogen. In another embodiment, $R^2$ represents $C_{1-6}$ alkyl, especially methyl.

Suitable values of the group $R^2$ include hydrogen and methyl.

Suitably, $R^a$ may represent trifluoromethyl; or $C_{1-6}$ alkyl, $C_{2-6}$ alkenyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Generally, $R^a$ may represent trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents.

Selected values of $R^a$ include $C_{1-6}$ alkyl, $C_{2-6}$ alkenyl, $C_{3-7}$ cycloalkyl, $C_{3-7}$ cycloalkyl($C_{1-6}$)alkyl, aryl($C_{1-6}$)alkyl, $C_{3-7}$ heterocycloalkyl, $C_{3-7}$ heterocycloalkyl-($C_{1-6}$)alkyl and heteroaryl($C_{1-6}$)alkyl, any of which groups may be optionally substituted by one or more substituents. In addition, $R^a$ may represent hydrogen.

Illustrative values of $R^a$ include $C_{1-6}$ alkyl, $C_{2-6}$ alkenyl, $C_{3-7}$ cycloalkyl, $C_{3-7}$ heterocycloalkyl and $C_{3-7}$ heterocycloalkyl($C_{1-6}$)alkyl, any of which groups may be optionally substituted by one or more substituents.

Typical values of $R^a$ include $C_{1-6}$ alkyl and $C_{3-7}$ cycloalkyl, either of which groups may be optionally substituted by one or more substituents.

Illustratively, $R^a$ represents trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents. Furthermore, $R^a$ may represent optionally substituted allyl. In addition, $R^a$ may represent hydrogen; or tetrahydropyranyl or dioxanylmethyl, either of which groups may be optionally substituted by one or more substituents.

Typically, $R^a$ represents methyl, ethyl, n-propyl, isopropyl, n-butyl, 2-methyl-propyl, tert-butyl, pentyl, hexyl, cyclopropyl, cyclobutyl, cyclopentyl or cyclohexyl, any of which groups may be optionally substituted by one or more substituents. Typically, $R^a$ may also represent allyl, piperidinyl, tetrahydrofurylmethyl or imidazolidinylethyl, any of which groups may be optionally substituted by one or more substituents. Typically, $R^a$ may further represent hydrogen; or cyclopropylmethyl, benzyl, tetrahydropyranyl, pyrrolidinylmethyl, pyrrolidinylpropyl, dioxanylmethyl, imidazolylmethyl or pyridinylmethyl, any of which groups may be optionally substituted by one or more substituents.

Desirably, $R^a$ represents hydrogen; or methyl, ethyl, n-propyl, isopropyl, n-butyl, 2-methylpropyl, allyl, cyclopropyl, cyclopropylmethyl, benzyl, tetrahydropyranyl, piperidinyl, tetrahydrofurylmethyl, pyrrolidinylmethyl, pyrrolidinylpropyl, dioxanylmethyl, imidazolidinylethyl, imidazolylmethyl or pyridinylmethyl, any of which groups may be optionally substituted by one or more substituents.

Appositely, $R^a$ represents methyl, ethyl, n-propyl, n-butyl, allyl, cyclopropyl, piperidinyl, tetrahydrofurylmethyl or imidazolidinylethyl, any of which groups may be optionally substituted by one or more substituents.

Typical examples of suitable substituents on $R^a$ include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, amino, $C_{1-6}$ alkylamino, di($C_{1-6}$)-alkylamino, phenylamino, pyridinylamino, $C_{2-6}$ alkylcarbonylamino, $C_{2-6}$ alkoxycarbonyl-amino and aminocarbonyl. Additional examples of suitable substituents on $R^a$ include ($C_{1-6}$)alkylaminocarbonyl and di($C_{1-6}$)alkylaminocarbonyl.

Selected examples of suitable substituents on $R^a$ include $C_{1-6}$ alkyl, $C_{1-6}$ alkoxy, $C_{1-6}$ alkylthio, hydroxy, oxo, $C_{2-6}$ alkylcarbonyl, carboxy, $C_{2-6}$ alkylcarbonylamino, ($C_{1-6}$)alkylaminocarbonyl and di($C_{1-6}$)alkylaminocarbonyl.

Illustrative examples of suitable substituents on $R^a$ include $C_{1-6}$ alkoxy, hydroxy, oxo, $C_{2-6}$ alkylcarbonyl, $C_{2-6}$ alkylcarbonylamino and di($C_{1-6}$)alkylaminocarbonyl.

Typical examples of specific substituents on $R^a$ include fluoro, chloro, bromo, methyl, ethyl, isopropyl, methoxy, isopropoxy, difluoromethoxy, trifluoromethoxy, methoxymethyl, methylthio, ethylthio, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, amino, methylamino, ethylamino, dimethylamino, phenylamino, pyridinylamino, acetylamino, tert-butoxycarbonylamino and aminocarbonyl. Additional examples of specific substituents on $R^a$ include ethoxy, methylaminocarbonyl and dimethylaminocarbonyl.

Selected examples of specific substituents on $R^a$ include methyl, methoxy, ethoxy, methylthio, hydroxy, oxo, acetyl, carboxy, acetylamino, methylaminocarbonyl and dimethylaminocarbonyl.

Illustrative examples of specific substituents on $R^a$ include methoxy, ethoxy, hydroxy, oxo, acetyl, acetylamino and dimethylaminocarbonyl.

Particular values of $R^a$ include hydrogen, methyl, carboxymethyl, methylaminocarbonylmethyl, dimethylaminocarbonylmethyl, ethyl, methoxyethyl, ethoxyethyl, methylthioethyl, hydroxyethyl, acetylaminoethyl, methoxypropyl, dihydroxypropyl, methoxyprop-2-yl, n-butyl, 2-hydroxy-2-methylpropyl, allyl, cyclopropyl, hydroxycyclopropylmethyl, benzyl, tetrahydropyranyl, oxopiperidinyl, acetylpiperidinyl, tetrahydrofurylmethyl, oxopyrrolidinylmethyl, acetylpyrrolidinylmethyl, oxopyrrolidinylpropyl, dioxanylmethyl, imidazolidinonylethyl, methylimidazolylmethyl and pyridinylmethyl.

Selected values of $R^a$ include methyl, dimethylaminocarbonylmethyl, ethyl, methoxyethyl, ethoxyethyl, hydroxyethyl, acetylaminoethyl, methoxypropyl, n-butyl, allyl, cyclopropyl, oxopiperidinyl, acetylpiperidinyl, tetrahydrofurylmethyl and imidazolidinonylethyl.

In a particular embodiment, $R^a$ represents $C_{1-6}$ alkyl. In one aspect of that embodiment, $R^a$ represents methyl. In another aspect of that embodiment, $R^a$ represents n-butyl.

A particular value of $R^a$ is oxopiperidinyl, especially 2-oxopiperidin-5-yl.

In a favoured embodiment, $R^a$ represents oxopyrrolidinylmethyl, especially 2-oxopyrrolidin-5-ylmethyl.

Favourably, $R^a$ represents pyridinylmethyl, especially the N-oxide derivative thereof.

Suitably, $R^b$ represents hydrogen or $C_{1-6}$ alkyl. In one embodiment, $R^b$ is hydrogen. In another embodiment, $R^b$ represents $C_{1-6}$ alkyl, especially methyl or ethyl, particularly methyl. In one aspect of that embodiment, $R^b$ represents methyl. In another aspect of that embodiment, $R^b$ represents ethyl. In a further embodiment, $R^b$ represents $C_{3-7}$ cycloalkyl, e.g. cyclopropyl, cyclobutyl, cyclopentyl or cyclohexyl.

One sub-class of compounds according to the invention is represented by the compounds of formula (IIA) and N-oxides thereof, and pharmaceutically acceptable salts and solvates thereof:

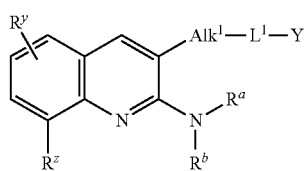

(IIA)

wherein $Alk^1$, $L^1$, Y, $R^a$ and $R^b$ are as defined above; and $R^y$ and $R^z$ independently represent hydrogen, $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$) alkylamino, halogen, cyano or trifluoromethyl.

Typically, $R^y$ represents hydrogen or halogen. Suitably, $R^y$ represents hydrogen.

In one embodiment, $R^y$ represents hydrogen. In another embodiment, $R^y$ represents halogen. In one aspect of that embodiment, $R^y$ represents fluoro. In another aspect of that embodiment, $R^y$ represents chloro.

Typically, $R^z$ represents hydrogen, $C_{1-6}$ alkyl or halogen. Appositely, $R^z$ represents $C_{1-6}$ alkyl or halogen. Suitably, $R^z$ represents $C_{1-6}$ alkyl, especially methyl.

In one embodiment, $R^z$ represents hydrogen. In another embodiment, $R^z$ represents $C_{1-6}$ alkyl. In one aspect of that embodiment, $R^z$ represents methyl. In another aspect of that embodiment, $R^z$ represents ethyl. In a further embodiment, $R^z$ represents halogen. In one aspect of that embodiment, $R^z$ represents fluoro. In another aspect of that embodiment, $R^z$ represents chloro.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above wherein $L^1$ represents oxygen, sulphur or N—$R^2$ may be prepared by a process which comprises reacting a compound of formula (III) with a compound of formula (IV):

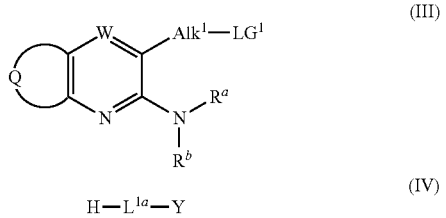

wherein $L^{1a}$ represents oxygen, sulphur or N—$R^2$, $LG^1$ represents a suitable leaving group, and Q, W, $Alk^1$, Y, $R^2$, $R^a$ and $R^b$ are as defined above.

The leaving group $LG^1$ is typically a halogen atom, e.g. bromo or iodo.

The reaction is conveniently effected at ambient or elevated temperature in a suitable solvent, e.g. N,N-dimethylformamide or acetonitrile. The reaction may be performed in the presence of a suitable base, e.g. an inorganic base such as potassium carbonate, cesium carbonate, sodium hydride or aqueous sodium hydroxide.

The intermediates of formula (III) above wherein $LG^1$ is bromo or iodo may be prepared from a compound of formula (V):

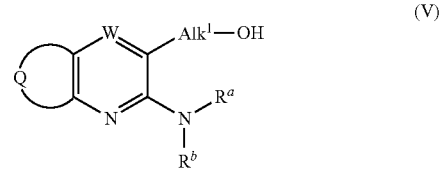

wherein Q, W, $Alk^1$, $R^a$ and $R^b$ are as defined above; by bromination or iodination:

The bromination reaction is conveniently effected by stirring compound (V) with an appropriate brominating agent, e.g. phosphorus tribromide, in a suitable solvent, e.g. a halogenated hydrocarbon such as dichloromethane.

The iodination reaction is conveniently effected by stirring compound (V) with an appropriate iodinating agent, e.g. elemental iodine, in a suitable solvent, e.g. a halogenated hydrocarbon such as dichloromethane, typically in the presence of triphenylphosphine and imidazole.

Alternatively, the intermediates of formula (III) above wherein $Alk^1$ represents methylene and $LG^1$ is bromo may be prepared from a compound of formula (VI):

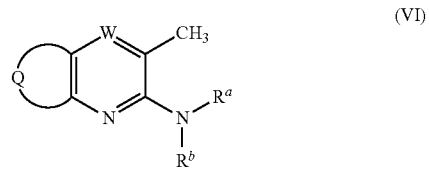

wherein Q, W, $R^a$ and $R^b$ are as defined above; by bromination.

The reaction is conveniently effected at an elevated temperature in a suitable solvent, e.g. a halogenated solvent such as carbon tetrachloride, in the presence of a suitable brominating agent, e.g. N-bromosuccinimide, typically in the presence of a catalyst such as benzoyl peroxide.

In another procedure, the compounds of formula (I) wherein $L^1$ represents oxygen may be prepared by a process which comprises reacting a compound of formula (V) as defined above with a compound of formula $LG^2$-Y, in which Y is as defined above and $LG^2$ represents a suitable leaving group.

The leaving group $LG^2$ is typically a halogen atom, e.g. chloro or bromo. Alternatively, $LG^2$ may be a $C_{1-6}$ alkylsulphonyl group, e.g. methylsulphonyl.

The reaction is conveniently effected by stirring compound (V), typically at an elevated temperature, with a compound $LG^2$-Y in a suitable solvent, e.g. N,N-dimethylformamide or 1,4-dioxane, typically under basic conditions, e.g. in the presence of an inorganic base such as sodium hydride.

In another procedure, the compounds of formula (I) wherein $L^1$ represents sulfur may be prepared by a process which comprises reacting a compound of formula $LG^2$-Y with a compound of formula (VII):

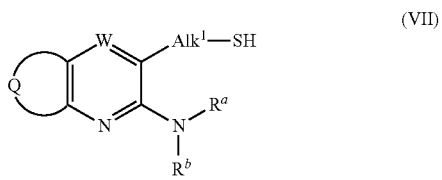

wherein Q, W, $Alk^1$, Y, $R^a$, $R^b$ and $LG^2$ are as defined above.

The reaction is conveniently effected by stirring compound (VII) with a compound $LG^2$-Y in a suitable solvent, e.g. a lower alkanol such as methanol, typically under basic conditions, e.g. in the presence of an alkali metal alkoxide such as sodium methoxide.

The intermediates of formula (VII) may typically be prepared by treating a suitable compound of formula (III) above with thiolacetic acid; followed by treatment of the resulting compound with a base, e.g. an alkali metal alkoxide such as sodium methoxide.

In another procedure, the compounds of formula (I) wherein $L^1$ represents N—$R^2$ may be prepared by a process which comprises reacting a compound of formula $LG^2$-Y with a compound of formula (VIII):

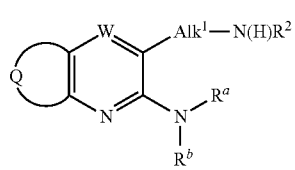
(VIII)

wherein Q, W, $Alk^1$, Y, $R^2$, $R^a$, $R^b$ and $LG^2$ are as defined above.

The reaction is conveniently effected at an appropriate temperature, e.g. at ambient temperature or at an elevated temperature, in a suitable solvent, e.g. tetrahydrofuran, n-butanol, 1-methyl-2-pyrrolidinone (NMP) or 1,4-dioxane. The reaction may be performed in the presence of a suitable base, e.g. an organic base such as N,N-diisopropylethylamine.

The intermediates of formula (VIII) wherein $R^2$ represents hydrogen may be prepared by treating a suitable compound of formula (III) above with potassium phthalimide; followed by treatment of the resulting compound with hydrazine. Alternatively, they may be prepared by treating a suitable compound of formula (III) above with sodium azide; followed by treatment of the resulting compound with triphenylphosphine.

In an additional procedure, the compounds of formula (I) wherein $Alk^1$ represents methylene and $L^1$ represents $N-R^2$ may be prepared by a process which comprises reacting a compound of formula Y—$N(H)R^2$ with a compound of formula (IX):

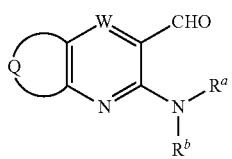
(IX)

wherein Q, W, Y, $R^2$, $R^a$ and $R^b$ are as defined above; under reducing conditions.

The reaction is conveniently effected by stirring compound (IX) with a compound Y—$N(H)R^2$ at an elevated temperature in a suitable solvent, e.g. a cyclic ether such as tetrahydrofuran, in the presence of a reducing agent. A suitable reducing agent comprises a mixture of di-n-butyltin dichloride and phenylsilane.

The intermediates of formula (VIII) wherein $Alk^1$ represents methylene and $R^2$ represents $C_{1-6}$ alkyl, e.g. methyl, may be prepared by treating a suitable compound of formula (IX) above with a $C_{1-6}$ alkylamine, e.g. methylamine, in the presence of titanium(IV) n-propoxide and a base, e.g. an organic base such as N,N-diisopropylamine; followed by treatment of the resulting compound with a reducing agent, e.g. sodium triacetoxyborohydride.

The intermediates of formula (V) wherein $Alk^1$ represents methylene may be prepared from the corresponding compound of formula (IX) by treatment with a reducing agent, e.g. sodium borohydride.

The intermediates of formula (V), (VII) and (VIII) may be prepared by reacting a compound of formula (X) with a compound of formula (XI):

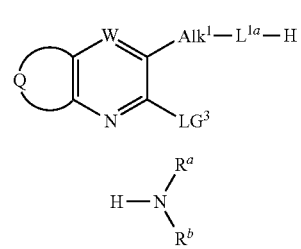
(X)

(XI)

wherein Q, W, $Alk^1$, $L^{1a}$, $R^a$ and $R^b$ are as defined above, and $LG^3$ represents a suitable leaving group.

The leaving group $LG^3$ is typically a halogen atom, e.g. chloro.

The reaction is conveniently effected at an elevated temperature in a suitable solvent, e.g. tetrahydrofuran, isopropanol, n-butanol or 1-methyl-2-pyrrolidinone (NMP). The reaction may be performed in the presence of a suitable base, e.g. an organic base such as N,N-diisopropylethylamine.

In a further procedure, the compounds of formula (I) may be prepared by a process which comprises reacting a compound of formula (XI) as defined above with a compound of formula (XII):

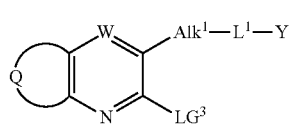
(XII)

wherein Q, W, $Alk^1$, $L^1$, Y and $LG^3$ are as defined above.

In a variant of the above procedure, the compounds of formula (I) wherein $R^a$ and $R^b$ both represent hydrogen may be prepared by a process which comprises reacting a compound of formula (XII) as defined above with trifluoroacetamide and a catalytic quantity of trans-N,N'-dimethylcyclohexane-1,2-diamine.

The above reaction, and the reaction between compounds (XI) and (XII), are both conveniently effected in the presence of a transition metal catalyst. A suitable transition metal catalyst is a copper(I) salt, e.g. a copper(I) halide such as copper(I) iodide.

Moreover, both reactions may be conveniently carried out at an elevated temperature in a suitable solvent, e.g. isopropanol, ethylene glycol or acetonitrile. The reactions may be performed in the presence of a suitable base, e.g. a phosphate salt such as potassium phosphate, or a carbonate salt such as caesium carbonate.

The intermediates of formula (XII) wherein $L^1$ represents oxygen, sulphur or $N-R^2$ may be prepared by reacting a compound of formula (X) as defined above with a compound of formula $LG^2$-Y, in which Y and $LG^2$ are as defined above, under conditions analogous to those described above for the reaction of a compound of formula (V), (VII) or (VIII) with a compound of formula $LG^2$-Y.

Where they are not commercially available, the starting materials of formula (IV), (VI), (IX), (X) and (XI) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of illustration, a compound of formula (I) wherein the moiety Y is substituted by a halogen atom, e.g. chloro, may be converted into the corresponding compound wherein Y is substituted by amino (—NH$_2$) by treatment with ammonia. Similarly, a compound of formula (I) wherein the moiety Y is substituted by a halogen atom, e.g. chloro, may be converted into the corresponding compound wherein Y is substituted by $C_{1-6}$ alkylamino (e.g. methylamino or tert-butylamino), di($C_{1-6}$)alkylamino (e.g. dimethylamino) or arylamino (e.g. phenylamino) by treatment with the appropriate $C_{1-6}$ alkylamine (e.g. methylamine or tert-butylamine), di($C_{1-6}$)alkylamine (e.g. dimethylamine) or arylamine (e.g. aniline) respectively.

A compound of formula (I) wherein Y is substituted by $C_{1-6}$ alkylthio, e.g. methylthio, may be converted into the corresponding compound wherein Y is substituted by $C_{1-6}$ alkylsulphonyl, e.g. methylsulphonyl, by treatment with an oxidising agent, e.g. 3-chloroperoxybenzoic acid. Removal of the $C_{1-6}$ alkylsulphonyl moiety from a compound of formula (I) wherein Y is substituted by $C_{1-6}$ alkylsulphonyl, e.g. methylsulphonyl, may be effected by treatment with a reducing agent, e.g. sodium borohydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 μM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the IC$_{50}$.

When tested in the above assay, the compounds of the accompanying Examples were all found to possess IC$_{50}$ values for inhibition of activity of human PI3Kα and/or PI3Kβ and/or PI3Kγ and/or PI3Kδ of 50 μM or better.

EXAMPLES

| Abbreviations | |
|---|---|
| MeCN: acetonitrile | DCM: dichloromethane |
| Et$_2$O: diethyl ether | DIPEA: N,N-diisopropylethylamine |
| DMF: N,N-dimethylformamide | EtOAc: ethyl acetate |
| NMP: 1-methyl-2-pyrrolidinone | THF: tetrahydrofuran |
| TFA: trifluoroacetic acid | PPh$_3$: triphenylphosphine |
| Me: methyl | Ph: phenyl |
| MeOH: methanol | DMSO: dimethylsulfoxide |
| MCPBA: 3-chloroperoxybenzoic acid | TBAF: tetrabutylammonium fluoride |
| r.t.: room temperature | RT: retention time |
| SiO$_2$: silica | h: hour |
| br: broad | M: mass |
| HPLC: High Performance Liquid Chromatography | |
| LCMS: Liquid Chromatography Mass Spectrometry | |
| ES+: Electrospray Positive Ionisation | |

Analytical Conditions

All NMRs were obtained at 400 MHz.

Compounds were named with the aid of Beilstein Autonom or the Cambridgesoft Chemistry Cartridge (v. 9.0.0.182) software.

All reactions involving air- or moisture-sensitive reagents were performed under a nitrogen atmosphere using dried solvents and glassware. Degassing was performed by bubbling nitrogen through the reaction mixture.

| Analytical Condition | Method | Description | |
|---|---|---|---|
| 10 cm_ESCI_AmmBicarb_MeCN<br>10 cm_ESCI_Bicarb_MeCN<br>10 cm_ESI_Bicarb<br>10 cm_ESI_Bicarb_MeCN<br>10 cm_APCI_Formic | 1 | Solvents:<br><br><br><br>Column:<br><br>Flow Rate:<br>Gradient: | Acetonitrile (far UV grade)<br>Water (high purity via PureLab Option unit) with 10 mM ammonium hydrogencarbonate<br>Waters Xterra MS 5 μm C18, 100 × 4.6 mm (Plus guard cartridge)<br>2 mL/min<br>A: Water/Bicarb<br>B: MeCN |

| Time | A % | B % |
|---|---|---|
| 0.00 | 95 | 5 |
| 0.50 | 95 | 5 |
| 4.00 | 5 | 95 |
| 5.50 | 5 | 95 |
| 5.60 | 95 | 5 |
| 6.50 | 95 | 5 |

| Analytical Condition | Method | Description | |
|---|---|---|---|
| 10 cm_ESI_Formic<br>10 cm_ESI_Formic_MeCN | 2 | Solvents:<br><br><br><br><br>Column:<br><br>Flow Rate:<br>Gradient: | Acetonitrile (far UV grade) with 0.1% (v/v) formic acid<br>Water (high purity via PureLab Option unit) with 0.1% formic acid<br>Phenomenex Luna 5 μm C18 (2), 100 × 4.6 mm (Plus guard cartridge)<br>2 mL/min<br>A: Water/formic acid<br>B: MeCN/formic acid |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

| Analytical Condition | Method | Description | |
|---|---|---|---|
| 10 cm_ESI_Formic_MeOH | 3 | Solvents:<br><br><br><br><br>Column:<br><br>Flow Rate:<br>Gradient: | Methanol (LC-MS grade) with 0.1% (v/v) formic acid<br>Water (high purity via PureLab Option unit) with 0.1% formic acid<br>Phenomenex Luna 5 μm C18 (2), 100 × 4.6 mm (Plus guard cartridge)<br>2 mL/min<br>A: Water/formic acid<br>B: MeOH/formic acid |

| Time | A % | B % |
|---|---|---|
| 0.00 | 95 | 5 |
| 3.50 | 5 | 95 |
| 7.00 | 5 | 95 |
| 7.10 | 95 | 5 |
| 8.00 | 95 | 5 |

| Analytical Condition | Method | Description | |
|---|---|---|---|
| 15 cm_Formic_Slow_Sunfire_HPLC<br>15 cm_Formic_Slow<br>15 cm_ESCI_Formic | 4 | Solvents:<br><br><br><br>Column:<br><br>Flow Rate:<br>Gradient: | Acetonitrile (far UV grade) with 0.1% (v/v) formic acid<br>Water (high purity via PureLab Ultra unit) with 0.1% formic acid<br>Waters Sunfire 5 μm C18, 150 × 4.6 mm<br>1 mL/min<br>A: Water/formic acid<br>B: MeCN/formic acid |

| Time | A % | B % |
|---|---|---|
| 0.00 | 98 | 2 |
| 4.00 | 98 | 2 |
| 20.0 | 0 | 100 |
| 22.0 | 0 | 100 |
| 22.5 | 98 | 2 |
| 24 | 98 | 2 |

| Analytical Condition | Method | Description | |
|---|---|---|---|
| 15 cm_Formic_Sunfire_HPLC_MeCN | 5 | Solvents:<br><br><br><br>Column:<br><br>Flow Rate:<br>Gradient: | Acetonitrile (far UV grade) with 0.1% (v/v) formic acid<br>Water (high purity via PureLab Ultra unit) with 0.1% formic acid<br>Waters Sunfire 5 μm C18, 150 × 4.6 mm<br>1 mL/min<br>A: Water/formic acid<br>B: MeCN/formic acid |

| Analytical Condition | Method | Description | | | |
|---|---|---|---|---|---|
| | | | Time | A % | B % |
| | | | 0.00 | 95 | 5 |
| | | | 1.00 | 95 | 5 |
| | | | 30.0 | 0 | 100 |
| | | | 40.0 | 0 | 100 |
| | | | 40.5 | 95 | 5 |
| | | | 45 | 95 | 5 |
| 25 cm_Bicarb_Slow_XBridge_HPLC_MeCN | 6 | Solvents: | Acetonitrile (far UV grade) Water (high purity via PureLab Option unit) with 10 mM ammonium hydrogencarbonate | | |
| | | Column: | Waters Xbridge 5 μm C18 (2), 250 × 4.6 mm | | |
| | | Flow Rate: | 1 mL/min | | |
| | | Gradient: | A: Water/formic acid B: MeCN/formic acid | | |
| | | | Time | A % | B % |
| | | | 0.00 | 95 | 5 |
| | | | 2.5 | 95 | 5 |
| | | | 22 | 0 | 100 |
| | | | 25 | 0 | 100 |
| | | | 25.1 | 95 | 5 |
| | | | 26.5 | 95 | 5 |
| 25 cm_Bicarb_Xbridge_HPLC | 7 | Solvents: | Acetonitrile (far UV grade) Water (high purity via PureLab Option unit) with 10 mM ammonium hydrogencarbonate | | |
| | | Column: | Waters Xterra 5 μm C18 (2), 250 × 4.6 mm | | |
| | | Flow Rate: | 1 mL/min | | |
| | | Gradient: | A: Water/formic acid B: MeCN/formic acid | | |
| | | | Time | A % | B % |
| | | | 0.00 | 95 | 5 |
| | | | 1.00 | 95 | 5 |
| | | | 30.0 | 0 | 100 |
| | | | 40.0 | 0 | 100 |
| | | | 40.5 | 95 | 5 |
| | | | 45 | 95 | 5 |
| 15 cm_Formic_Ascentis_HPLC_CH3CN | 8 | Solvents: | Acetonitrile (far UV grade) with 0.1% (v/v) formic acid Water (high purity via PureLab Option unit) with 0.1% formic acid | | |
| | | Column: | Supelco, Ascentis ® Express C18, 2.7 μm C18, 150 × 4.6 mm | | |
| | | Flow Rate: | 1 mL/min | | |
| | | Gradient: | A: Water/formic acid B: MeCN/formic acid | | |
| | | | Time | A % | B % |
| | | | 0.00 | 96 | 4 |
| | | | 3.00 | 96 | 4 |
| | | | 9.00 | 0 | 100 |
| | | | 13.6 | 0 | 100 |
| | | | 13.7 | 96 | 4 |
| | | | 15.0 | 96 | 4 |
| 15 cm_Bicarb_ETERNITY_HPLC_CH3CN | 9 | Solvents: | 100% Acetonitrile (far UV grade) Water (high purity via PureLab Ultra unit) with 10 mM ammonium bicarbonate | | |
| | | Column: | Hichrom, Kromasil Eternity, 2.5 μm C18, 150 × 4.6 mm | | |
| | | Flow Rate: | 1 mL/min | | |
| | | Gradient: | A: 10 mM Ammonium bicarbonate in water B: 100% MeCN | | |
| | | | Time | A % | B % |
| | | | 0.00 | 95.5 | 4.5 |
| | | | 3.00 | 95.5 | 4.4 |
| | | | 9.00 | 0 | 100 |
| | | | 13.6 | 0 | 10 |

| Analytical Condition | Method Description | | |
|---|---|---|---|
| | 13.7 | 95.5 | 4.5 |
| | 15 | 95.5 | 4.5 |

Intermediate 1

[1-(2-Chloro-8-methylquinolin-3-yl)ethyl]carbamic acid tert-butyl ester

To a solution of 2-chloro-8-methylquinoline-3-carboxaldehyde (3.3 g, 16 mmol) in THF (100 mL) under nitrogen cooled to −78° C. was added a solution of methyl-magnesium bromide (3M in Et$_2$O, 6.0 mL, 18 mmol). After stirring at −78° C. for 1 h the mixture was allowed to warm to r.t. and 5% aqueous acetic acid (20 mL) added. The mixture was concentrated in vacuo and the aqueous residue extracted with EtOAc (2×150 mL). The organic layers were combined, dried (MgSO$_4$), filtered and the solvent removed in vacuo. The residue was purified by column chromatography (SiO$_2$, 33% EtOAc in heptane) to give the desired alcohol as a white solid. To a solution of this solid (2.6 g, 11.6 mmol) in DCM was added PPh$_3$ (3.0 g, 11.5 mmol), iodine (2.8 g, 11.0 mmol) and imidazole (1.0 g, 14.7 mmol). The reaction mixture was stirred at r.t. for 2 h, then washed with water (2×75 mL) The organic layer was separated, dried (MgSO$_4$), filtered through silica gel (20 g) and the silica washed with DCM. The filtrate was concentrated in vacuo to give the desired iodide as a brown solid. To a solution of this iodide (2.6 g, 7.85 mmol) in dry DMF (20 mL) under nitrogen was added sodium azide (1.0 g, 15.3 mmol), and the mixture was stirred at r.t. for 18 h. Water (100 mL) was added and the mixture was extracted with EtOAc (200 mL). The organic layer was washed with water (2×50 mL), separated, dried (MgSO$_4$), filtered and the solvent removed in vacuo to give a pale yellow liquid. This was dissolved in THF (30 mL) and PPh$_3$ (2.8 g, 10.7 mmol) and water (5 mL) were added. The reaction was stirred at r.t. for 1 h and then heated at reflux for 1 h. After cooling to r.t., the organic solvent was removed in vacuo and the aqueous residue was acidified with 1M HCl and washed with EtOAc (50 mL). The aqueous layer was basified with 1M NaOH and extracted with DCM (2×75 mL). The organic layers were combined, dried (MgSO$_4$) and concentrated in vacuo to give the desired amine as a colourless gum. To a solution of this amine (2.2 g, 9.95 mmol) in dry DCM (50 mL) was added di-tert-butyl dicarbonate (2.2 g, 10.1 mmol) and the reaction was stirred at r.t. for 72 h. The mixture was concentrated in vacuo and the residue purified by column chromatography (SiO$_2$, 33% EtOAc in heptane) to give the title compound (2.6 g, 50%) as a white solid. $\delta_H$ (CDCl$_3$) 8.07 (s, 1H), 7.64 (d, J=8.0 Hz, 1H), 7.54 (d, J=7.2 Hz, 1H), 7.43 (t, J=7.6 Hz, 1H), 5.01-5.22 (m, 2H), 2.76 (s, 3H), 1.20-1.60 (m, 12H). LCMS (ES+) 321, 323 (M+H)$^+$.

Intermediate 2

{1-[2-(N-Butyl-N-methylamino)-8-methylquinolin-3-yl]ethyl}carbamic acid tert-butyl ester To a solution of Intermediate 1 (200 mg, 0.62 mmol) in NMP (4 mL) were added N-methylbutylamine (0.37 mL, 3.12 mmol) and DIPEA (0.56 mL, 3.12 mmol). The reaction mixture was heated at 140° C. in a sealed tube overnight. Water (20 mL) was added and the mixture was extracted with EtOAc (150 mL). The organic layer was washed with water (3×25 mL), separated, dried (MgSO$_4$), filtered and the solvent removed in vacuo. The residue was purified by column chromatography (SiO$_2$, 5-10% EtOAc in petrol 40-60) to give the title compound (127 mg, 55%) as a yellow viscous oil. $\delta_H$ (CDCl$_3$) 7.90 (s, 1H), 7.52 (d, J=8.0 Hz, 1H), 7.42 (d, J=7.2 Hz, 1H), 7.23 (t, J=7.6 Hz, 1H), 5.10-5.20 (m, 1H), 4.95-5.05 (m, 1H), 2.97 (s, 3H), 2.70 (s, 3H), 1.62-1.69 (m, 2H), 1.30-1.50 (m, 16H), 0.93 (t, J=8.0 Hz, 3H). LCMS (ES+) 372 (M+H)$^+$.

Intermediate 3

(R)-2-Methylpropane-2-sulfinic acid 1-(2-chloro-8-methylquinolin-3-yl)meth-(E)-ylideneamide To a solution of 2-chloro-8-methylquinoline-3-carboxaldehyde (2.05 g, 10 mmol) in dry THF (20 mL) under nitrogen was added titanium isopropoxide (5.68 g, 20 mmol) and the mixture stirred at r.t. for 10 minutes. (R)-(+)-2-Methyl-2-propanesulfinamide (1.21 g, 10 mmol) was added to the reaction which was stirred at r.t. for 72 h. Water (20 mL) was added and the mixture was extracted with DCM (150 mL). The organic layer was separated, dried (MgSO$_4$), filtered and the solvent removed in vacuo to afford the title compound (2.4 g, 72%) as a pale yellow solid. $\delta_H$ (CDCl$_3$) 9.12 (s, 1H), 8.79 (s, 1H), 7.78 (d, J=8.4 Hz, 1H), 7.67 (d, J=6.8 Hz, 1H), 7.51 (t, J=7.8 Hz, 1H), 2.79 (s, 3H), 1.32 (s, 9H). LCMS (ES+) 309, 311 (M+H)$^+$.

Intermediate 4

(R)-2-Methylpropane-2-sulfinic acid [(S)-1-(2-chloro-8-methylquinolin-3-yl)ethyl]amide To a solution of Intermediate 3 (1.9 g, 6.15 mmol) in dry DCM (40 mL) under nitrogen cooled to −78° C. was added dropwise over 10 minutes a solution of methyl-magnesium bromide (4.1 mL, 12.3 mmol, 3.0M in DCM). The reaction mixture was allowed to warm to r.t. and stirred for 18 h. Saturated NH$_4$Cl solution (50 mL) was added and the aqueous layer was extracted with DCM (100 mL). The organic layers were combined, dried (MgSO$_4$), filtered and concentrated in vacuo to give a yellow oil. This was crystallised from petrol 40-60 to afford the title compound (900 mg, 45%) as a pale yellow solid. $\delta_H$ (CDCl$_3$) 8.17 (s, 1H), 7.64 (d, J=8.0 Hz, 1H), 7.56 (d, J=7.2 Hz, 1H), 7.45 (t, J=7.6 Hz, 1H), 5.09-5.12 (m, 1H), 3.44 (d, J=4.8 Hz, 1H), 2.77 (s, 3H), 1.71 (d, J=6.8 Hz, 3H), 1.25 (s, 9H). LCMS (ES+) 325, 327 (M+H)$^+$.

Intermediate 5

N-{(S)-1-[2-(N-Allyl-N-methylamino)-8-methylquinolin-3-yl]ethyl}-(R)-2-methylpropane-2-sulfinamide Intermediate 4 (1.0 g, 3 mmol) and N-methylallylamine (5 mL) were combined in a sealed tube and heated at 110° C. for 5 days. The reaction mixture was cooled and partitioned between EtOAc and water. The organic layer was washed (water, brine), dried (phase separation cartridge) and concentrated in vacuo. The residue was purified by column chromatography (SiO$_2$, 50% EtOAc in isohexane) to give the title compound (1.0 g, 93%) as a brown solid. $\delta_H$ (CDCl$_3$) 8.02 (1H, s), 7.51 (1H, d, J=8.05 Hz), 7.44 (1H, d, J=6.89 Hz), 7.28-7.22 (1H, m), 6.09-5.99 (1H, m), 5.39 (1H, dq, J 17.17, 1.74 Hz), 5.23 (1H, dq, J 10.26, 1.62 Hz), 5.07-4.99 (1H, m), 3.97-3.89 (1H, m), 3.85-3.76 (1H, m), 3.47 (1H, d, J=4.61 Hz), 2.94 (3H, s), 2.71 (3H, s), 1.58 (3H, d, J=6.57 Hz), 1.21 (9H, s).

Intermediate 6

(S)—N-Allyl-3-(1-aminoethyl)-N,8-dimethylquinolin-2-amine

Intermediate 5 (1.1 g, 3.1 mmol) in MeOH (10 mL) was treated with 4M HCl in 1,4-dioxane (10 mL). The mixture was stirred at r.t. for 16 h and concentrated in vacuo. The residue was taken up in MeOH and placed on an SCX cartridge. The cartridge was washed through with MeOH and the target compound eluted with 7N NH$_3$/MeOH. The title compound (580 mg, 75%) was obtained as a yellow foam. $\delta_H$ (CDCl$_3$) 8.08 (1H, s), 7.54 (1H, d, J=8.05 Hz), 7.43 (1H, d, J=6.99 Hz), 7.28-7.20 (1H, m), 6.09-5.98 (1H, m), 5.35 (1H, dq, J 17.18, 1.72 Hz), 5.22 (1H, dq, J 10.23, 1.59 Hz), 4.52 (1H, q, J=6.51 Hz), 3.94-3.78 (2H, m), 2.93 (3H, s), 2.71 (3H, s), 1.48 (3H, d, J=6.52 Hz).

Intermediate 7

6-Chloro-9-{[2-(trimethylsilyl)ethoxy]methyl}-9H-purine

6-Chloropurine (5.0 g, 32 mmol) in DMF (75 mL) was treated with potassium carbonate (9.0 g, 65 mmol) and [2-(chloromethoxy)ethyl]trimethylsilane (7.0 g, 42 mmol) and stirred for 2 h. The reaction mixture was partitioned between EtOAc and water. The organic layer was dried (MgSO$_4$), concentrated in vacuo and purified by column chromatography (SiO$_2$, 20% EtOAc in isohexane) to give the title compound (4.9 g, 54%) as an off-white solid. $\delta_H$ (CDCl$_3$) 8.82 (1H, s), 8.32 (1H, s), 5.71 (2H, s), 3.71-3.61 (2H, m), 1.03-0.93 (2H, m), 0.00 (9H, s).

Intermediate 8

(S)—N-Allyl-N,8-dimethyl-3-[1-(9-{[2-(trimethylsilyl)ethoxy]methyl}-9H-purin-6-ylamino)ethyl]quinolin-2-amine Intermediate 6 (580 mg, 2.3 mmol), Intermediate 7 (840 mg, 2.95 mmol) and DIPEA (2.0 mL, 11 mmol) in n-butanol (2.0 mL) were combined in a sealed tube and heated under microwave irradiation to 150° C. for 50 minutes. The reaction mixture was partitioned between DCM and water. The organic layer was dried (phase separation cartridge) and concentrated in vacuo. The resulting residue was purified by column chromatography (SiO$_2$, 40% EtOAc in isohexane) to give the title compound (1.0 g, 86%) as a yellow solid. $\delta_H$ (CDCl$_3$) 8.39 (1H, s), 8.06 (1H, s), 7.96 (1H, s), 7.51 (1H, d, J=8.06 Hz), 7.46 (1H, d, J=7.05 Hz), 7.25 (1H, t, J=7.54 Hz), 6.22 (1H, br s), 6.22-6.06 (1H, m), 5.99-5.77 (1H, m), 5.61 (2H, s), 5.42 (1H, dd, J 17.20, 2.03 Hz), 5.24 (1H, dd, J 10.20, 1.90 Hz), 4.35 (1H, dd, J 15.53, 5.49 Hz), 3.91 (1H, dd, J 15.48, 6.01 Hz), 3.72-3.61 (2H, m), 3.09 (3H, s), 2.76 (3H, s), 1.66 (3H, d, J=6.64 Hz), 1.64-1.56 (1H, m), 1.50-1.34 (1H, m), 0.00 (9H, s).

Intermediate 9

N-(3-Fluoro-2-methylphenyl)acetamide

To a solution of 3-fluoro-2-methylaniline (6.00 g, 48 mmol) in dry DCM (100 mL) under nitrogen was added acetic anhydride (7.6 g, 75 mmol). The reaction mixture was stirred at r.t. for 18 h then washed with water (2×50 mL) and NaOH solution (1M, 2×50 mL). The organic layer was dried (MgSO$_4$), filtered and concentrated in vacuo to give the title compound (8.0 g, 100%) as a white solid. $\delta_H$ (CDCl$_3$) 7.56 (1H, s), 7.16 (1H, q, J=7.6 Hz), 6.99 (1H, br s), 6.87 (1H, t, J=8.4 Hz), 2.27 (3H, s), 2.16 (3H, s).

Intermediate 10

2-Chloro-7-fluoro-8-methylquinoline-3-carbaldehyde

To dry DMF (12 mL) at 0° C. was added POCl$_3$ (48 mL) over 30 minutes. The reaction mixture was warmed to r.t. and Intermediate 9 (8.0 g, 48 mmol) was added portionwise. After being heated to 85° C. for 18 h, the reaction mixture was cooled to r.t. and poured dropwise into ice/water (500 mL). The resulting precipitate was filtered, washed with water (500 mL) and dried to give the title compound (7.2 g, 67%) as a white solid. $\delta_H$ (CDCl$_3$) 10.56 (1H, s), 8.71 (1H, s), 7.82 (1H, q, J=7.6 Hz), 7.42 (1H, t, J=7.6 Hz), 2.67 (3H, s).

Intermediate 11

(E)-N-[(2-Chloro-7-fluoroquinolin-3-yl)methylidene]-(R)-2-methylpropane-2-sulfinamide To a solution of 2-chloro-7-fluoroquinoline-3-carboxaldehyde (6.3 g, 30 mmol) in dry THF (200 mL) under nitrogen was added titanium isopropoxide (17.0 g, 60 mmol) and the reaction mixture stirred at r.t. for 10 minutes. (R)-2-Methyl-2-propanesulfin-amide (3.6 g, 30 mmol) was added to the reaction mixture which was stirred at r.t. for 72 h and partitioned between water (20 mL) and DCM (150 mL). The organic layer was dried (MgSO$_4$), filtered and concentrated in vacuo to give the title compound (7.2 g, 76%) as a pale yellow solid. $\delta_H$ (CDCl$_3$) 9.09 (1H, s), 8.83 (1H, s), 7.96 (1H, dd, J=6.0 Hz), 7.69 (1H, d, J=7.2 Hz), 7.42 (1H, t, J=8.4 Hz), 1.32 (9H, s).

Intermediate 12

(E)-N-[(2-Chloro-7-fluoro-8-methylquinolin-3-yl)methylidene]-(R)-2-methylpropane-2-sulfinamide Similarly, Intermediate 10 (6.6 g, 29.5 mmol), titanium isopropoxide (17 g, 60 mmol), (R)-2-methyl-2-propanesulfinamide (3.6 g, 29.5 mmol) and THF (200 mL) gave the title compound (8.3 g, 86.4%) as a yellow solid. $\delta_H$ (CDCl$_3$) 9.12 (1H, s), 8.73 (1H, s), 7.71 (1H, dd, J=6.0 Hz), 7.40 (1H, t, J=8.2 Hz), 2.69 (3H, s), 1.32 (9H, s).

Intermediate 13

N—[(S)-1-(2-Chloro-7-fluoroquinolin-3-yl)ethyl]-(R)-2-methylpropane-2-sulfinamide To a solution of Intermediate 11 (7.2 g, 23.5 mmol) in dry DCM (40 mL) under nitrogen was added dropwise over 10 minutes at −78° C. a solution of methylmagnesium bromide (16.0 mL, 48 mmol; 3.0M in Et$_2$O). After warming to r.t., the reaction mixture was stirred for 18 h and partitioned between a saturated solution of NH$_4$Cl (50 mL) and DCM (100 mL) The organic layer was dried (MgSO$_4$), filtered and concentrated in vacuo to give a yellow oil which was crystallised from 40-60 petroleum ether to give the title compound (4.0 g, 53%) as a pale yellow solid. $\delta_H$ (CDCl$_3$) 8.23 (1H, s), 7.16 (1H, dd, J=6.0 Hz), 7.65 (1H, d, J=7.2 Hz), 7.46 (1H, t, J=8.4 Hz), 5.16 (1H, q, J=6.8 Hz), 3.45 (1H, br s), 1.71 (3H, d, J=6.8 Hz), 1.26 (9H, s).

Intermediate 14

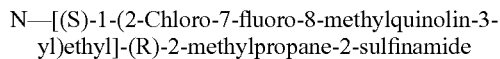

N—[(S)-1-(2-Chloro-7-fluoro-8-methylquinolin-3-yl)ethyl]-(R)-2-methylpropane-2-sulfinamide Similarly, Intermediate 12 (8.3 g, 25.4 mmol), methylmagnesium bromide (16.0 mL, 48 mmol; 3.0M in Et$_2$O), and DCM (100 mL) gave the title compound (4.2 g, 48%) as a yellow solid. $\delta_H$ (CDCl$_3$) 8.17 (1H, s), 7.63 (1H, dd, J=6.0 Hz), 7.32 (1H, t, J=8.8 Hz), 5.16 (1H, q, J=6.8 Hz), 3.45 (1H, d, J=6.8 Hz), 2.66 (3H, s) 1.70 (3H, d, J=6.8 Hz), 1.26 (9H, s).

Intermediate 15

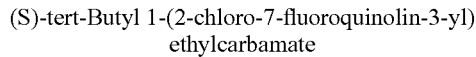

(S)-tert-Butyl 1-(2-chloro-7-fluoroquinolin-3-yl)ethylcarbamate

To a solution of Intermediate 13 (4.0 g, 12.17 mmol) in MeOH (20 mL) was added conc. HCl (1 mL) and the mixture stirred at r.t. for 2 h. The reaction mixture was partitioned between DCM (100 mL) and 2M NaOH solution (50 mL). The organic layer was dried (MgSO$_4$) and filtered. To this filtrate was added DIPEA (3.0 mL, 15.0 mmol) followed by a solution of di-tert-butyl dicarbonate (3.0 g, 13.76 mmol) in DCM (10 mL) dropwise. The reaction mixture was stirred at r.t. for 3 h, then diluted with DCM (10 mL) and washed with saturated NaHCO$_3$ solution (15 mL) and brine (15 mL). The organic layer was dried (MgSO$_4$), concentrated in vacuo and purified by column chromatography (SiO$_2$, 0-30% EtOAc in 40-60 petroleum ether) to give the title compound (3.4 g, 86%) as a white solid. $\delta_H$ (CDCl$_3$) 8.23 (1H, s), 7.16 (1H, dd, J=6.0 Hz), 7.65 (1H, d, J=7.2 Hz), 7.46 (1H, t, J=8.4 Hz), 5.18 (1H, br q, J=6.8 Hz), 3.49 (1H, d, J=6.8 Hz), 1.54 (3H, d, J=6.8 Hz), 1.48 (9H, s).

Intermediate 16

(S)-tert-Butyl 1-(2-chloro-7-fluoro-8-methylquinolin-3-yl)ethylcarbamate

Similarly, Intermediate 14 (4.2 g, 12.2 mmol), conc. HCl (1 mL), di-tert-butyl dicarbonate (2.7 g, 12.2 mmol) and DIPEA (1.6 g, 12.2 mmol) gave the title compound (4.38 g, 90%) as a yellow solid. $\delta_H$ (CDCl$_3$) 8.07 (1H, s), 7.62 (1H, dd, J=6.0 Hz), 7.30 (1H, t, J=8.8 Hz), 5.17 (1H, m), 5.07 (1H, br s), 2.65 (3H, s) 1.54 (3H, d, J=6.4 Hz), 1.42 (9H, s).

Intermediate 17

(S)-3-(1-Aminoethyl)-7-fluoro-N-(2-methoxyethyl)quinolin-2-amine hydrochloric acid salt To a solution of Intermediate 15 (0.28 g, 0.86 mmol) in n-butanol (2 mL) was added 2-methoxyethylamine (75 mg, 1.0 mmol) and DIPEA (0.42 mL, 2.33 mmol). The reaction mixture was heated at 110° C. for 18 h and then concentrated in vacuo. The residue was purified by column chromatography (SiO$_2$, 0-3% MeOH in DCM) to give a pale orange oil (97 mg, 55%). To a solution of this oil in MeOH (2 mL) was added HCl (1.0 mL, 4.0M solution in 1,4-dioxane). The reaction mixture was stirred for 2 h and concentrated in vacuo to give the title compound (200 mg, 60%) as a beige solid. $\delta_H$ (CDCl$_3$) 7.67 (1H, s), 7.52 (1H, dd, J=6.8 Hz), 7.29 (1H, d, J=8.8 Hz), 6.90 (1H, t, J=6.8 Hz), 6.10 (1H, br s), 4.92 (1H, br s), 4.56 (1H, br d), 3.83 (1H, m, 1H), 3.73 (1H, m), 3.63 (2H, m), 3.45 (3H, s), 1.60 (3H, d, J=6.8 Hz).

Intermediate 18

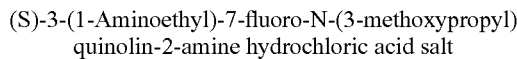

(S)-3-(1-Aminoethyl)-7-fluoro-N-(3-methoxypropyl)quinolin-2-amine hydrochloric acid salt Similarly, Intermediate 15 (0.28 g, 0.86 mmol), 3-methoxypropylamine (80 mg, 1.0 mmol) and DIPEA (0.42 mL, 2.33 mmol) gave the title compound (140 mg, 50%) as a beige solid. $\delta_H$ (CDCl$_3$) 7.65 (1H, s), 7.49 (1H, dd, J=6.8 Hz), 7.65 (1H, d, J=8.8 Hz), 6.93 (1H, t, J=6.8 Hz), 6.10 (1H, br s), 4.88 (1H, br s), 4.56 (1H, br d), 3.63 (2H, m), 3.55 (2H, t, J=6.8 Hz), 3.38 (3H, s), 1.98 (2H, m), 1.60 (3H, d, J=6.8 Hz).

Intermediate 19

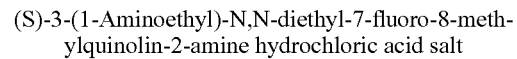

(S)-3-(1-Aminoethyl)-N,N-diethyl-7-fluoro-8-methylquinolin-2-amine hydrochloric acid salt Similarly, Intermediate 16 (0.28 g, 0.83 mmol), diethylamine (80 mg, 1.1 mmol) and DIPEA (0.42 mL, 2.33 mmol) gave the title compound (150 mg, 48%) as a beige solid. $\delta_H$ (CDCl$_3$) 7.88 (1H, s), 7.48 (1H, dd, J=6.8 Hz), 7.09 (1H, t, J=8.8 Hz), 5.10 (2H, br s), 3.46 (4H, q, J=6.8 Hz), 3.31 (1H, br s), 2.58 (3H, s), 1.41 (3H, d, J=6.8 Hz), 1.19 (6H, t, J=6.8 Hz).

Intermediate 20

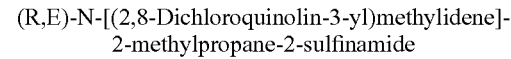

(R,E)-N-[(2,8-Dichloroquinolin-3-yl)methylidene]-2-methylpropane-2-sulfinamide

To a solution of 2,8-dichloroquinoline-3-carboxaldehyde (43.0 g, 0.19 mol) in anhydrous THF (500 mL) was added titanium isopropoxide (114 mL, 0.38 mol) at r.t. After 15 minutes, (R)-2-methyl-2-propanesulfinamide (23.0 g, 0.19 mol) was added and stirring was continued for 17 h at r.t. Water (1 L) was added to the reaction mixture and the precipitate obtained was filtered and washed with DCM. The organic layer was dried (Na$_2$SO$_4$) and concentrated in vacuo to give the title compound (61 g, 97%) as a pale yellow solid. $\delta_H$ (CDCl$_3$) 9.11 (1H, s), 8.83 (1H, s), 7.93 (1H, dd, J 7.54, 1.31 Hz), 7.88 (1H, dd, J 8.22, 1.31 Hz), 7.55 (1H, t, J 7.88 Hz), 1.33 (9H, s).

Intermediate 21

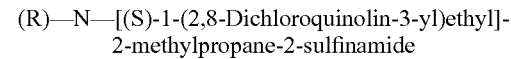

(R)—N—[(S)-1-(2,8-Dichloroquinolin-3-yl)ethyl]-2-methylpropane-2-sulfinamide

To a solution of Intermediate 20 (61 g, 0.18 mol) was added dropwise methyl-magnesium bromide (123.5 mL, 0.37 mol; 3M in Et$_2$O) over 50 minutes in DCM (1.5 L) at −70° C. under nitrogen. The reaction mixture was allowed to reach r.t. with stirring overnight. The mixture was cooled in ice-salt as saturated aqueous NH$_4$Cl (500 mL) was slowly added with stirring. The aqueous layer was extracted with DCM (2×500 mL). The combined organic layers were dried (MgSO$_4$) and concentrated in vacuo. The residue was triturated with Et$_2$O and the solid filtered, washed with Et$_2$O and dried under reduced pressure to give the title compound (32 g, 50%) as a pale pink solid. $\delta_H$ (CDCl$_3$) 8.26 (1H, s), 7.83 (1H, dd, J 7.52, 1.32 Hz), 7.74 (1H, dd, J 8.19, 1.32 Hz), 7.49 (1H, t, J=7.86 Hz), 5.16-5.07 (1H, m), 3.47 (1H, d, J=4.63 Hz), 1.71 (3H, d, J=6.75 Hz), 1.25 (9H, s).

Intermediate 22

(S)-1-(2,8-Dichloroquinolin-3-yl)ethanamine

To a solution of Intermediate 21 (37.7 g, 0.11 mol) in MeOH (370 mL) was added 4N hydrogen chloride in 1,4-dioxane (58 mL) at r.t. The reaction mixture was stirred for 2 h and concentrated in vacuo. The residue was partitioned between 5N hydrochloric acid (300 mL) and DCM (300 mL). The organic layer was extracted with 5N hydrochloric acid (100 mL) and the combined aqueous layers basified with aqueous NaOH and extracted with DCM (3×500 mL) and chloroform (3×500 mL). The organic layer was dried (MgSO$_4$) and concentrated in vacuo to afford the title compound (23.7 g, 90%) as an amber oil. $\delta_H$(CDCl$_3$) 8.40 (1H, s), 7.80 (1H, dd, J 7.51, 1.33 Hz), 7.75 (1H, dd, J 8.19, 1.33 Hz), 7.46 (1H, t, J 7.86 Hz), 4.67 (1H, q, J=6.52 Hz), 1.50 (3H, d, J=6.53 Hz).

Intermediate 23

(S)-tert-Butyl 1-(2,8-dichloroquinolin-3-yl)ethylcarbamate

To a stirred solution of Intermediate 22 (23.7 g, 98 mmol) and DIPEA (51 mL, 0.3 mol) in DCM (1 L) was added di-tert-butyl dicarbonate (25.7 g, 118 mmol). The reaction mixture was allowed to stand at r.t. overnight and concentrated in vacuo. The residue was triturated with 40-60 petroleum ether, filtered, washed with 40-60 petroleum ether and dried under reduced pressure to give the title compound (28.4 g, 85%) as a colourless solid. $\delta_H$ (CDCl$_3$) 8.13 (1H, s), 7.80 (1H, dd, J 7.51, 1.32 Hz), 7.72 (1H, dd, J 8.18, 1.31 Hz), 7.46 (1H, t, J=7.85 Hz), 5.23-5.16 (1H, m), 5.10 (1H, br s), 1.55 (3H, br d, J=7.18 Hz), 1.42 (9H, br s).

Intermediate 24

(S)-tert-Butyl 1-[2-(1-acetylpiperidin-4-ylamino)-8-chloroquinolin-3-yl]ethylcarbamate A mixture of Intermediate 23 (0.34 g, 1 mmol), 1-(4-aminopiperidin-1-yl)-ethanone (0.25 g, 1.76 mmol) and DIPEA (0.84 mL, 5 mmol) in NMP (10 mL) was heated at 140° C. for 18 h. After cooling, the reaction mixture was partitioned between Et$_2$O (200 mL) and water (100 mL). The organic layer was washed with water (3×100 mL), brine (100 mL), dried (MgSO$_4$) and concentrated in vacuo. The residue was purified by column chromatography (SiO$_2$, 0-100% EtOAc in isohexane) to give the title compound (0.1 g, 22%) as a pale orange gum. $\delta_H$ (CDCl$_3$) 7.70 (1H, s), 7.62 (1H, dd, J 7.56, 1.40 Hz), 7.47 (1H, dd, J 7.93, 1.39 Hz), 7.08 (1H, t, J=7.74 Hz), 6.39 (1H, br s), 4.97-4.87 (1H, m), 4.59 (1H, br d, J=9.95 Hz), 4.50-4.42 (2H, m), 3.85-3.78 (1H, m), 3.37-3.27 (1H, m), 3.08-2.96 (1H, m), 2.40-2.25 (1H, m), 2.23-2.13 (1H, m), 2.12 (3H, d, J=3.80 Hz), 1.67-1.62 (3H, m), 1.60-1.47 (2H, m), 1.44 (9H, s).

Intermediate 25

(S)-1-{4-[3-(1-Aminoethyl)-8-chloroquinolin-2-ylamino]piperidin-1-yl}ethanone

To a solution of Intermediate 24 (0.1 g, 0.22 mmol) in DCM (5 mL) was added TFA (2 mL). After 2 h at r.t. the mixture was concentrated in vacuo and the residue was dissolved in DCM and applied to a 2 g SCX column. The column was washed with DCM, then 50% DCM in MeOH, then MeOH, then eluted with 1M ammonia in MeOH to give the title compound (62 mg, 85%) as a pale orange gum. $\delta_H$ (CDCl$_3$) 8.03 (1H, s), 7.59 (1H, dd, J 7.56, 1.45 Hz), 7.55 (1H, s), 7.44 (1H, dd, J 7.90, 1.41 Hz), 7.06 (1H, t, J=7.73 Hz), 4.45 (1H, br s), 4.37-4.24 (2H, m), 3.83-3.71 (1H, m), 3.41-3.31 (1H, m), 3.20-3.09 (1H, m), 2.41-2.30 (1H, m), 2.34-1.99 (1H, m), 2.13 (3H, s), 1.64-1.52 (4H, m), 1.50 (3H, d, J=6.59 Hz).

Intermediate 26

(S)-tert-Butyl 1-[8-chloro-2-(diethylamino)quinolin-3-yl]ethylcarbamate

A mixture of Intermediate 23 (200 mg, 0.59 mmol), diethylamine (0.3 mL, 2.92 mmol) and DIPEA (0.52 mL, 2.92 mmol) in NMP (3 mL) was heated at 140° C. overnight. The reaction mixture was cooled and partitioned between water (10 mL) and EtOAc/Et$_2$O (100 mL). The organic layer was washed with water (2×10 mL), dried (MgSO$_4$) and concentrated in vacuo. The residue was purified by column chromatography (SiO$_2$, 5-10% EtOAc in 40-60 petroleum ether) to give the title compound (122 mg, 55%) as a yellow oil. $\delta_H$ (CDCl$_3$) 7.92 (1H, s), 7.66 (1H, dd, J 7.54, 1.39 Hz), 7.58 (1H, dd, J 8.01, 1.39 Hz), 7.23 (1H, t, J=7.78 Hz), 5.10 (1H, br s), 4.94 (1H, br s), 3.58-3.45 (2H, m), 3.37 (2H, br s), 1.47-1.36 (12H, m), 1.24 (6H, t, J=6.99 Hz).

Intermediate 27

(S)-tert-Butyl 1-[8-chloro-2-(2-methoxyethylamino)quinolin-3-yl]ethylcarbamate

Similarly, Intermediate 23 (120 mg, 0.35 mmol), 2-methoxyethylamine (132 mg, 1.75 mmol) and DIPEA (0.3 mL, 1.75 mmol) in NMP (3 mL) gave the title compound (69 mg, 52%) as a pale yellow solid. $\delta_H$ (CDCl$_3$) 7.70 (1H, s), 7.62 (1H, dd, J 7.54, 1.42 Hz), 7.47 (1H, dd, J 7.91, 1.42 Hz), 7.08 (1H, t, J=7.73 Hz), 6.31 (1H, br s), 4.93 (1H, br s), 4.56 (1H, br d, J=9.31 Hz), 3.97-3.90 (1H, m), 3.86-3.78 (1H, m), 3.75-3.69 (2H, m), 3.43 (3H, s), 1.62 (3H, d, J=6.76 Hz), 1.45 (9H, s).

Intermediate 28

(S)-tert-Butyl 1-{8-chloro-2-[N-(2-methoxyethyl)-N-methylamino]quinolin-3-yl}ethyl carbamate Similarly, Intermediate 23 (120 mg, 0.35 mmol), N-(2-methoxyethyl)methylamine (156 mg, 1.75 mmol) and DIPEA (0.3 mL, 1.75 mmol) in NMP (3 mL) gave the title compound (115 mg, 83%) as a pale yellow solid. $\delta_H$ (CDCl$_3$) 7.95 (1H, s), 7.67 (1H, dd, J 7.47, 1.37 Hz), 7.58 (1H, dd, J 8.02, 1.35 Hz), 7.26-7.20 (1H, m), 5.18 (1H, br s), 5.03 (1H, br s), 3.86-3.77 (1H, m), 3.73 (2H, t, J=5.62 Hz), 3.52 (1H, s), 3.37 (3H, s), 3.12 (3H, s), 1.46-1.39 (12H, m).

Intermediate 29

(S)-tert-Butyl 1-[8-chloro-2-(methylamino)quinolin-3-yl]ethylcarbamate

Similarly, Intermediate 23 (180 mg, 0.53 mmol), methylamine oxalate salt (424 mg, 2.63 mmol) and DIPEA (0.47 mL, 2.63 mmol) in NMP (3 mL) gave the title compound (72 mg, 41%) as a yellow oil. $\delta_H$ (CDCl$_3$) 7.68 (1H, s), 7.62 (1H, dd, J 7.54, 1.43 Hz), 7.47 (1H, dd, J 7.91, 1.42 Hz), 7.08 (1H, t, J=7.73 Hz), 4.92 (1H, br s), 4.53 (1H, d, J=9.73 Hz), 3.19 (3H, d, J=4.63 Hz), 1.64 (3H, d, J=6.81 Hz), 1.45 (9H, s).

Alternative procedure: A mixture of Intermediate 23 (700 mg, 2.05 mmol) and 2N MeNH$_2$ in THF (4 mL) was heated at 70° C. for 20 h. The reaction mixture was concentrated in vacuo onto silica gel and purified by column chromatography (SiO$_2$, 10-100% EtOAc in isohexane) to afford the title compound (649 mg, 94%) as a clear gum.

Intermediate 30 tert-Butyl (S)-1-(8-chloro-2-{[(R)-tetrahydrofur-2-ylmethyl]amino}quinolin-3-yl)ethyl-carbamate

Similarly, Intermediate 23 (150 mg, 0.44 mmol), (R)-tetrahydrofurfurylamine (0.23 mL, 2.19 mmol) and DIPEA (0.39 mL, 2.19 mmol) in NMP (3 mL) gave the title compound (100 mg, 62%) as a yellow solid. $\delta_H$ (CDCl$_3$) 7.70 (1H, s), 7.61 (1H, dd, J 7.54, 1.40 Hz), 7.47 (1H, dd, J 7.92, 1.42 Hz), 7.08 (1H, t, J=7.75 Hz), 6.20 (1H, br s), 4.92 (1H, br s), 4.57 (1H, d, J=9.17 Hz), 4.32-4.24 (1H, m), 4.04-3.89 (2H, m), 3.83-3.75 (1H, m), 3.61-3.53 (1H, m), 2.11-2.02 (1H, m), 2.01-1.85 (2H, m), 1.80-1.70 (1H, m), 1.61 (3H, d, J=6.78 Hz), 1.45 (9H, s).

Intermediate 31 tert-Butyl (S)-1-(8-chloro-2-{[(S)-tetrahydrofur-2-ylmethyl]amino}quinolin-3-yl)ethyl-carbamate

Similarly, Intermediate 23 (150 mg, 0.44 mmol), (S)-tetrahydrofurfurylamine (0.23 mL, 2.19 mmol) and DIPEA (0.39 mL, 2.19 mmol) in NMP (3 mL) gave the title compound (81 mg, 45%) as a yellow oil. $\delta_H$ (CDCl$_3$) 7.69 (1H, s), 7.61 (1H, dd, J 7.55, 1.40 Hz), 7.46 (1H, dd, J 7.91, 1.44 Hz), 7.11-7.04 (1H, m), 6.20 (1H, br s), 4.92 (1H, br s), 4.58 (1H, d, J=9.09 Hz), 4.31-4.21 (1H, m), 3.99-3.91 (1H, m), 3.82-3.75 (3H, m), 2.09-1.85 (3H, m), 1.80-1.71 (1H, m), 1.64-1.56 (3H, m), 1.45 (9H, s).

Intermediate 32

(S)-3-(1-Aminoethyl)-8-chloro-N-(2-methoxyethyl)quinolin-2-amine bis hydrochloric acid salt

A solution of Intermediate 27 (65 mg, 0.17 mmol) and hydrogen chloride (0.86 mL, 3.42 mmol; 4.0M in 1,4-dioxane) in 1,4-dioxane (5 mL) was stirred at r.t. overnight. The reaction mixture was concentrated in vacuo and purified by triturating in Et$_2$O to give the title compound (55 mg, 91%) as an off-white solid. $\delta_H$ (MeOD-d$_4$) 8.61 (1H, s), 8.06-7.98 (2H, m), 7.66-7.59 (1H, m), 3.99-3.89 (4H, m), 3.61 (3H, s), 1.79 (3H, d, J=6.73 Hz), 1H under H$_2$O.

Intermediate 33

(S)-3-(1-Aminoethyl)-8-chloro-N-(2-methoxyethyl)-N-methylquinolin-2-amine bis hydrochloric acid salt

Similarly, Intermediate 28 (110 mg, 0.28 mmol) and hydrogen chloride (1.4 mL, 5.58 mmol; 4.0M in 1,4-dioxane) in 1,4-dioxane (5 mL) gave the title compound (97 mg, 95%) as a yellow solid. $\delta_H$ (MeOD-d$_4$) 8.82 (1H, s), 8.06-8.01 (2H, m), 7.65 (1H, t, J=7.93 Hz), 5.07 (1H, q, J=6.79 Hz), 4.03-3.82 (4H, m), 3.62 (3H, s), 3.41 (3H, s), 1.88 (3H, d, J=6.78 Hz).

Intermediate 34

(S)-3-(1-Aminoethyl)-8-chloro-N-methylquinolin-2-amine bis hydrochloric acid salt

Similarly, Intermediate 29 (70 mg, 0.21 mmol) and hydrogen chloride (1.0 mL, 4.17 mmol; 4.0M in 1,4-dioxane) in 1,4-dioxane (5 mL) gave the title compound (56 mg, 87%) as a cream solid. $\delta_H$ (MeOD-d$_4$) 8.51 (1H, s), 7.99 (1H, dd, J 7.87, 1.24 Hz), 7.96 (1H, dd, J 8.01, 1.26 Hz), 7.58 (1H, t, J=7.93 Hz), 3.40 (3H, s), 1.77 (3H, d, J=6.73 Hz), 1H under H$_2$O.

Intermediate 35

3-[(S)-1-Aminoethyl]-8-chloro-N-{[(R)-tetrahydrofur-2-yl]methyl}quinolin-2-amine bis hydrochloric acid salt

Similarly, Intermediate 30 (105 mg, 0.26 mmol) and hydrogen chloride (1.3 mL, 5.17 mmol; 4.0M in 1,4-dioxane) in 1,4-dioxane (5 mL) gave the title compound (90 mg, 92%) as an off-white solid. $\delta_H$ (MeOD-d$_4$) 8.68 (1H, s), 8.02 (2H, d, J 7.88 Hz), 7.63 (1H, t, J=7.88 Hz), 5.03-4.97 (1H, m), 4.41-4.33 (1H, m), 4.22-4.11 (1H, m), 4.11-3.94 (2H, m), 3.83 (1H, dd, J 15.30, 6.61 Hz), 2.28-2.19 (1H, m), 2.12-2.05 (2H, m), 1.96-1.82 (1H, m), 1.81 (3H, d, J=6.52 Hz).

Intermediate 36

(S)-1-(2-Chloro-8-methylquinolin-3-yl)ethylamine

To a solution of Intermediate 4 (0.25 g, 0.77 mmol) in MeOH (2 mL) was added conc. HCl (1 mL) and the mixture was stirred at r.t. for 2 h. The reaction was poured into DCM (100 mL) and washed with 2M NaOH solution (50 mL). The organic layer was separated, dried (MgSO$_4$), filtered and the solvent removed in vacuo to afford the title compound (0.16 g, 94%) as a white solid. $\delta_H$ (CDCl$_3$) 829 (s, 1H), 7.66 (d, J=8.4 Hz, 1H), 7.53 (d, J=6.8 Hz, 1H), 7.41-7.45 (m, 1H), 4.61-4.67 (m, 1H), 2.76 (s, 3H), 1.50 (d, J=4.0 Hz, 3H). LCMS (ES+) 221, 223 (M+H)$^+$.

Intermediate 37

[(S)-1-(2-Chloro-8-methylquinolin-3-yl)ethyl]carbamic acid tert-butyl ester

To a solution of Intermediate 36 (1.83 g, 3.11 mmol) in dry DCM (10 mL) under nitrogen was added DIPEA (2.7 mL, 15.6 mmol) followed by a solution of di-tert-butyl dicarbonate in DCM (10 mL) dropwise. The reaction mixture was stirred at r.t. for 3 h, then diluted with DCM (10 mL) and washed with saturated NaHCO$_3$ solution (15 mL) and brine (15 mL). The organic layer was separated, dried ($Na_2SO_4$), filtered and the solvent removed in vacuo. Purification by column chromatography ($SiO_2$, 0-30% EtOAc in 40-60 petroleum ether) afforded the title compound (897 mg, 34%) as a white solid. $\delta_H$ ($CDCl_3$) 8.07 (s, 1H), 7.64 (d, J=8.0 Hz, 1H), 7.54 (d, J=7.2 Hz, 1H), 7.43 (t, J=7.6 Hz, 1H), 5.12-5.22 (m, 1H), 5.00-5.10 (m, 1H), 2.76 (s, 3H), 1.50-1.57 (m, 3H), 1.30-1.50 (m, 9H). LCMS (ES+) 321, 323 (M+H)+.

Intermediate 38

(S)-3-(1-Aminoethyl)-8-chloro-N-methylquinolin-2-amine hydrochloride

A solution of Intermediate 29 (649 mg, 1.93 mmol) and HCl (4 mL, 2.0M in $Et_2O$) in MeOH (5 mL) was stirred at r.t. overnight. The reaction mixture was concentrated in vacuo to afford the title compound (535 mg, 99%) as a white solid. $\delta_H$ (MeOD-$d_4$) as for Intermediate 34.

Intermediate 39

(S)-2-[3-(1-Aminoethyl)-8-chloroquinolin-2-ylamino]ethanol hydrochloride

A solution of Intermediate 23 (700 mg, 2.05 mmol) and ethanolamine (1 mL) in n-butanol (5 mL) was heated at 120° C. for 20 h. The reaction mixture was concentrated in vacuo onto silica gel and purified by column chromatography ($SiO_2$, 10-100% EtOAc in isohexane) to afford the required intermediate (711 mg, 95%). LCMS (ES+) 368 (M+H)+. A solution of this material (711 mg, 1.94 mmol) and HCl (5 mL, 2.0M in $Et_2O$) in MeOH (5 mL) was stirred at r.t. overnight. The reaction mixture was concentrated in vacuo to afford the title compound (619 mg, 99%) as a white solid. $\delta_H$ (DMSO-$d_6$) 8.60 (3H, s), 8.21 (1H, s), 7.75 (1H, d, J=7.57 Hz), 7.68 (1H, d, J=7.92 Hz), 7.25 (1H, t, J=7.76 Hz), 4.78 (1H, t, J=6.77 Hz), 3.79-3.61 (4H, m), 1.59 (3H, d, J=6.54 Hz), 1H under water peak. LCMS (ES+) 268 (M+H)+.

Intermediate 40

(S)-1-[3-(1-Aminoethyl)-8-chloroquinolin-2-ylamino]-2-methylpropan-2-ol hydrochloride Similarly, Intermediate 23 (700 mg, 2.05 mmol), 1-amino-2-methylpropan-2-ol (300 mg, 3.37 mmol) and DIPEA (2 mL) in n-butanol (10 mL) afforded a white solid (614 mg, 76%). This solid was dissolved in MeOH (8 mL) and treated with a solution of HCl (10 mL, 2N in $Et_2O$). The reaction mixture was stirred at r.t. overnight. The solvent was evaporated in vacuo to give the title compound (573 mg, 99%) as a white solid. LCMS (ES+) 296 (M+H)+.

Intermediate 41

(S)-1-{[3-(1-Aminoethyl)-8-chloroquinolin-2-ylamino]methyl}cyclopropanol hydrochloride Similarly, Intermediate 23 (480 mg, 1.40 mmol), 1-(aminomethyl)cyclopropanol (200 mg, 2.30 mmol) and DIPEA (2 mL) in n-butanol (8 mL) afforded an off-white solid (280 mg, 52%). This solid was dissolved in MeOH (5 mL) and treated with a solution of HCl (8 mL, 2N in $Et_2O$). The reaction mixture was stirred at r.t. overnight. The solvent was evaporated in vacuo to give the title compound (270 mg, 99%) as a tan glass. LCMS (ES+) 294 (M+H)+.

Intermediate 42

(S)-1-{3-[3-(1-Aminoethyl)-8-chloroquinolin-2-ylamino]propyl}pyrrolidin-2-one hydrochloride Similarly, Intermediate 23 (150 mg, 0.44 mmol) and 1-(3-aminopropyl)pyrrolidin-2-one (1 mL) in n-butanol (5 mL) afforded the required intermediate. This was dissolved in MeOH (3 mL) and treated with a solution of HCl (3 mL, 2N in $Et_2O$). The reaction mixture was stirred at r.t. overnight. The solvent was evaporated in vacuo to give the title compound (169 mg, 99%). LCMS (ES+) 349 (M+H)+.

Intermediate 43

(S)-5-({3-[(S)-1-Aminoethyl]-8-chloroquinolin-2-ylamino}methyl)pyrrolidin-2-one

Similarly, Intermediate 23 (700 mg, 2.05 mmol), (S)-5-(aminomethyl)pyrrolidin-2-one (500 mg, 4.38 mmol) and DIPEA (2 mL) in n-butanol (12 mL) afforded a white solid (524 mg, 61%). The solid was dissolved in DCM (8 mL) and treated with TFA (3 mL). The reaction mixture was stirred at r.t. for 2 h, poured into 15% NaOH solution (20 mL) and extracted with EtOAc (50 mL). The organic phase was separated, dried ($MgSO_4$), filtered and concentrated in vacuo to afford the title compound (398 mg, 99%) as a clear glass. $\delta_H$ (DMSO-$d_6$) 8.28 (1H, t, J=5.58 Hz), 7.91-7.83 (1H, m), 7.79 (1H, s), 7.68-7.61 (3H, m), 7.20-7.11 (1H, m), 4.26 (1H, q, J=6.56 Hz), 4.00-3.89 (1H, m), 3.71-3.58 (2H, m), 2.32-2.08 (3H, m), 1.94-1.83 (1H, m), 1.51 (1H, d, J=6.59 Hz), 1.40 (3H, d, J=6.48 Hz). LCMS (ES+) 319 (M+H)+.

Intermediate 44

1-[(S)-3-({3-[(S)-1-Aminoethyl]-8-chloroquinolin-2-ylamino}methyl)pyrrolidin-1-yl]ethanone hydrochloride Similarly, Intermediate 23 (700 mg, 2.05 mmol), (S)-1-[3-(aminomethyl)-pyrrolidin-1-yl]ethanone (710 mg, 4.02 mmol) and DIPEA (3 mL) in n-butanol (12 mL) afforded a white solid (189 mg, 20%). This was dissolved in MeOH (5 mL) and treated with a solution of HCl (5 mL, 2.0M in $Et_2O$). The reaction mixture was stirred at r.t. overnight. The solvent was evaporated in vacuo to give the title compound (186 mg, 88%) as a tan glass. LCMS (ES+) 347 (M+H)+.

Intermediate 45

(S)-3-(1-Aminoethyl)-8-chloroquinolin-2-amine hydrochloride

A solution of Intermediate 23 (700 mg, 2.05 mmol) and sodium azide (195 mg, 3.0 mmol) in DMF (8 mL) was heated in a sealed tube at 120° C. for 20 h. The reaction mixture was diluted with EtOAc (50 mL) and washed with water (4×20 mL). The organic layer was separated, dried ($MgSO_4$), filtered and concentrated in vacuo to afford a tan solid (610 mg, 86%). LCMS (ES+) 370 (M+H)+. Zn dust (440 mg, 6.68 mmol) was added to this intermediate (464 mg, 1.33 mmol) in acetic acid (20 mL) and the reaction mixture stirred at r.t for 20 h. The reaction mixture was filtered and washed with MeOH (50 mL) and the filtrate was concentrated in vacuo to afford a yellow solid (380 mg, 88%). This solid was dissolved in MeOH (5 mL) and treated with a solution of HCl (10 mL, 2.0M in Et$_2$O). The reaction mixture was stirred at r.t. overnight. The solvent was evaporated in vacuo to give the title compound (260 mg, 98%) as a green gum. LCMS (ES+) 222 (M+H)$^+$.

Intermediate 46

(S)-2-{N'-[1-(1-Aminoethyl)-8-chloroquinolin-2-yl]-N'-methylamino}-N-methyl-acetamide Following the procedure described for Intermediate 39, Intermediate 23 (700 mg, 2.05 mmol), N-methyl-2-(methylamino)acetamide (209 mg, 2.05 mmol) and DIPEA (1 mL) in n-butanol (10 mL) afforded a white solid (284 mg, 34%). LCMS (ES+) 407 (M+H)$^+$. This solid (280 mg, 0.19 mmol) was dissolved in DCM (8 mL) and treated with TFA (4 mL). The reaction mixture was stirred at r.t. for 2 h., poured onto 15% NaOH solution (30 mL) and extracted with EtOAc (50 mL). The organic phase was separated, dried (MgSO$_4$), filtered and concentrated in vacuo to afford the title compound (205 mg, 97%) as a clear glass. $\delta_H$ (CDCl$_3$) 8.89 (1H, s), 8.22 (1H, s), 7.71-7.62 (2H, m), 7.31-7.24 (1H, m), 4.52 (1H, q, J=6.44 Hz), 4.33 (1H, d, J=15.25 Hz), 4.08 (1H, d, J=15.25 Hz), 3.14 (3H, s), 2.86 (3H, d, J=4.87 Hz), 1.50 (3H, d, J=6.45 Hz). LCMS (ES+) 307 (M+H)$^+$.

Intermediate 47

(S)-3-(1-Aminoethyl)-8-chloro-N-[2-(methylthio)ethyl]quinolin-2-amine hydrochloride Similarly, Intermediate 23 (150 mg, 0.44 mmol) and 2-(methylthio)ethanamine (1 mL) in n-butanol (12 mL) afforded the required intermediate (174 mg). This was dissolved in MeOH (3 mL) and treated with a solution of HCl (3 mL, 2N in Et$_2$O). The reaction mixture was stirred at r.t. overnight. The solvent was evaporated in vacuo to give the title compound (118 mg, 90%) as a yellow solid. LCMS (ES+) 269 (M+H)$^+$.

Intermediate 48

(S)-3-(1-Aminoethyl)-8-chloro-N-[(1-methyl-1H-imidazol-4-yl)methyl]quinolin-2-amine hydrochloride Similarly, Intermediate 23 (700 mg, 2.05 mmol), (1-methyl-1H-imidazol-4-yl)methanamine (500 mg, 4.50 mmol) and DIPEA (4 mL) in n-butanol (10 mL) afforded a clear gum (701 mg, 82%). LCMS (ES+) 416 (M+H)$^+$. This was dissolved in MeOH (10 mL) and treated with a solution of HCl (8 mL, 2N in Et$_2$O). The reaction mixture was stirred at r.t. overnight. The solvent was evaporated in vacuo to give the title compound (707 mg, 99%) as a pink foam. LCMS (ES+) 316 (M+H)$^+$.

Intermediate 49 tert-Butyl (S)-1-{8-chloro-2-[(R)-2,3-dihydroxypropylamino]quinolin-3-yl}ethyl-carbamate A mixture of Intermediate 23 (150 mg, 0.44 mmol), (R)-3-amino-1,2-propanediol (200 mg, 2.19 mmol) and DIPEA (0.4 mL, 2.19 mmol) in NMP (3 mL) was heated at 100° C. overnight. The reaction mixture was cooled and partitioned between water (30 mL) and EtOAc (100 mL). The organic layer was washed with water (5×20 mL), separated, dried (MgSO$_4$) and concentrated in vacuo. The residue was purified by column chromatography (SiO$_2$, 75-100% EtOAc in isohexane) to give the title compound (147 mg, 85%) as a white solid. $\delta_H$ (CDCl$_3$) 7.75 (1H, s), 7.64 (1H, dd, J 7.6, 1.2 Hz), 7.49 (1H, dd, J 8.0, 1.2 Hz), 7.13 (1H, t, J=7.8 Hz), 7.00-6.90 (1H, m), 5.26-5.20 (1H, m), 4.98-4.90 (1H, m), 4.41 (1H, d, J=10.0 Hz), 3.90-3.75 (3H, m), 3.61-3.56 (2H, m), 3.38-3.32 (1H, m), 1.67 (3H, d, J=6.8 Hz), 1.45 (9H, s).

Intermediate 50 tert-Butyl (S)-1-{8-chloro-2-[(S)-2,3-dihydroxypropylamino]quinolin-3-yl}ethyl-carbamate Similarly, Intermediate 23 (150 mg, 0.44 mmol), (S)-3-amino-1,2-propanediol (200 mg, 2.19 mmol) and DIPEA (0.4 mL, 2.19 mmol) in NMP (3 mL) at 140° C. gave the title compound (147 mg, 85%) as a white solid. $\delta_H$ (CDCl$_3$) 7.75 (1H, s), 7.63 (1H, dd, J 7.6, 1.6 Hz), 7.49 (1H, dd, J 8.0, 1.2 Hz), 7.13 (1H, t, J=7.8 Hz), 7.00-6.90 (1H, m), 4.99-4.90 (2H, m), 4.61 (1H, d, J=10.0 Hz), 3.92-3.80 (3H, m), 3.62-3.50 (3H, m), 1.67 (3H, d, J=6.8 Hz), 1.45 (9H, s).

Intermediate 51

(S)-tert-Butyl 1-[7-fluoro-2-(2-methoxyethylamino)-8-methylquinolin-3-yl]ethyl-carbamate Similarly, Intermediate 16 (150 mg, 0.44 mmol), 2-methoxyethylamine (0.38 mL, 4.42 mmol) and DIPEA (0.3 mL, 1.75 mmol) in NMP (2 mL) at 120° C. gave the title compound (143 mg, 86%) as a yellow solid. $\delta_H$ (CDCl$_3$) 7.66 (1H, s), 7.37 (1H, dd, J 8.8, 6.4 Hz), 6.94 (1H, t, J=9.0 Hz), 6.19-6.10 (1H, m), 4.96-4.87 (1H, m), 4.58-4.52 (1H, m), 3.90-3.65 (4H, m), 3.42 (3H, s), 2.53 (3H, d, J=2.0 Hz), 1.61 (3H, d, J=6.4 Hz), 1.46 (9H, s).

Intermediate 52

(S)-tert-Butyl 1-{8-chloro-2-[2-(methylamino)-2-oxoethylamino]quinolin-3-yl}ethyl-carbamate Similarly, Intermediate 23 (150 mg, 0.44 mmol), 2-amino-N-methylacetamide hydrochloride (164 mg, 1.32 mmol) and DIPEA (0.47 mL, 2.63 mmol) in NMP (2 mL) at 120° C. for 4 days gave the title compound (62 mg, 36%) as an off-white solid. $\delta_H$ (CDCl$_3$) 7.90 (1H, br m), 7.77 (1H, s), 7.66 (1H, dd, J 7.6, 1.2 Hz), 7.52 (1H, dd J 8.0, 1.2 Hz), 7.16 (1H, br s), 7.00-6.90 (1H, m), 4.99-4.91 (1H, m), 4.61 (1H, d, J=9.2 Hz), 4.33 (1H, dd, J 14.8, 5.2 Hz), 4.16 (1H, dd, J 14.8, 5.2 Hz), 2.79 (3H, d, J=4.8 Hz), 1.65 (3H, d, J=6.8 Hz), 1.44 (9H, s).

Intermediate 53

(S)-tert-Butyl 1-[7-fluoro-2-(2-hydroxyethylamino)-8-methylquinolin-3-yl]ethyl-carbamate Similarly, Intermediate 16 (1.0 g, 2.95 mmol) and ethanolamine (1.8 mL, 29.5 mmol) in NMP (10 mL) at 120° C. gave the title compound (0.92 g, 86%) as a white solid. $\delta_H$ (CDCl$_3$) 7.69 (1H, s), 7.37 (1H, dd, J 8.8, 6.4 Hz), 6.96 (1H, t, J=9.0 Hz), 6.85-6.75 (1H, m), 5.66-5.63 (1H, m), 4.98-4.90 (1H, m), 4.60-4.56 (1H, m), 3.95-3.85 (2H, m), 3.80-3.72 (2H, m), 2.51 (3H, d, J=2.0 Hz), 1.65 (3H, d, J=6.8 Hz), 1.45 (9H, s), 1H exchanging.

Intermediate 54

(S)-tert-Butyl 1-{8-chloro-2-[2-(dimethylamino)-2-oxoethylamino]quinolin-3-yl}ethyl-carbamate Similarly, Intermediate 23 (200 mg, 0.59 mmol), 2-amino-N,N-dimethylacetamide (179 mg, 1.75 mmol) and DIPEA (0.63 mL, 3.51 mmol) in NMP (2 mL) at 120° C. gave the title compound (127 mg, 53%) as an off-white solid. $\delta_H$ (CDCl$_3$) 7.75 (1H, s), 7.62 (1H, dd, J 7.6, 1.2 Hz), 7.50 (1H, dd, J 8.0, 1.2 Hz), 7.11 (1H, br s), 6.50-6.40 (1H, m), 5.00-4.90 (1H, m), 4.80-4.70 (1H, m), 4.52 (1H, dd, J 17.2, 4.4 Hz), 4.16 (1H, dd, J 17.2, 4.4 Hz), 3.16 (3H, s), 3.04 (3H, s), 1.59 (3H, d, J=5.6 Hz), 1.43 (9H, s).

Intermediate 55

(S)-tert-Butyl 1-[8-chloro-2-(pyridin-2-ylmethylamino)quinolin-3-yl]ethylcarbamate Similarly, Intermediate 23 (250 mg, 0.73 mmol), 2-(aminomethyl)pyridine (0.38 mL, 3.65 mmol) and DIPEA (1.3 mL, 7.31 mmol) in NMP (2 mL) at 120° C. gave the title compound (255 mg, 84%) as a lemon-yellow solid. $\delta_H$ (CDCl$_3$) 8.56 (1H, d, J=4.4 Hz), 7.74 (1H, s), 7.63-7.61 (2H, m), 7.54 (1H, d, J=7.6 Hz), 7.49 (1H, d, J=8.0 Hz), 7.16-7.13 (1H, m), 7.09 (1H, t, J=7.8 Hz), 6.95-6.85 (1H, m), 5.09-4.93 (3H, m), 4.71 (1H, d, J=8.8 Hz), 1.64 (3H, d, J=6.8 Hz), 1.40 (9H, s).

Intermediate 56

(S)-tert-Butyl 1-[8-chloro-2-(pyridin-3-ylmethylamino)quinolin-3-yl]ethylcarbamate Similarly, Intermediate 23 (500 mg, 1.46 mmol), 3-(aminomethyl)pyridine (0.75 mL, 7.31 mmol) and DIPEA (2.6 mL, 14.6 mmol) in NMP (4 mL) at 120° C. gave the title compound (424 mg, 70%) as an off-white solid. $\delta_H$ (CDCl$_3$) 8.78 (1H, d, J=2.0 Hz), 8.47 (1H, dd, J 4.8, 1.6 Hz), 7.98-7.95 (1H, m), 7.71 (1H, s), 7.62 (1H, dd, J 7.6, 1.2 Hz), 7.47 (1H, dd, J 8.0, 1.2 Hz), 7.23-7.20 (1H, m), 7.09 (1H, t, J=7.8 Hz), 7.00-6.90 (1H, m), 5.00-4.90 (1H, m), 4.90-4.78 (2H, m), 4.57 (1H, d, J=9.6 Hz), 1.65 (3H, d, J=6.8 Hz), 1.39 (9H, s).

Intermediate 57

(S)-2-({3-[1-(tert-Butoxycarbonylamino)ethyl]-8-chloroquinolin-2-ylamino}methyl)-pyridine 1-oxide A mixture of Intermediate 55 (150 mg, 0.36 mmol) and MCPBA (137 mg, 0.44 mmol, 55%) in DCM (20 mL) was stirred at r.t. for 4 h. The solvent was removed in vacuo and the residue purified by column chromatography (SiO$_2$, 0-5% MeOH in EtOAc) to give the title compound (100 mg, 64%) as a cream solid. $\delta_H$ (CDCl$_3$) 8.23 (1H, d, J=6.0 Hz), 7.86-7.76 (1H, m), 7.73 (1H, s), 7.60 (1H, d, J 7.6 Hz), 7.48 (1H, dd, J 7.6, 0.8 Hz), 7.21-7.08 (3H, m), 6.98-6.84 (1H, m), 5.15 (1H, dd, J 15.2, 5.6 Hz), 5.03 (1H, dd, J 15.2, 6.0 Hz), 5.00-4.91 (1H, m), 4.80-4.70 (1H, m), 1.61 (3H, s), 1.42 (9H, s).

Intermediate 58

(R)-3-{3-[(S)-1-Aminoethyl]-8-chloroquinolin-2-ylamino}propane-1,2-diol bis hydrochloric acid salt A solution of Intermediate 49 (140 mg, 0.35 mmol) and HCl (1.8 mL, 7.07 mmol; 4.0M in 1,4-dioxane) in dry 1,4-dioxane (10 mL) was stirred at r.t. overnight. The reaction mixture was concentrated in vacuo to give the title compound (130 mg, quantitative) as a pale pink solid. $\delta_H$ (MeOD-d$_4$) 8.57 (1H, s), 8.00-7.96 (2H, m), 7.60 (1H, t, J=8.0 Hz), 4.96-4.84 (1H, m), 4.16-4.10 (1H, m), 3.98-3.83 (2H, m), 3.75-3.61 (2H, m), 1.79 (3H, d, J=6.8 Hz).

Intermediate 59

(S)-3-{3-[(S)-1-Aminoethyl]-8-chloroquinolin-2-ylamino}propane-1,2-diol bis hydrochloric acid salt Similarly, Intermediate 50 (60 mg, 0.15 mmol) and HCl (0.4 mL, 1.52 mmol; 4.0M in 1,4-dioxane) in dry 1,4-dioxane (5 mL) gave the title compound (56 mg, quantitative) as a dark pink solid. $\delta_H$ (MeOD-d$_4$) 8.57 (1H, s), 7.98-7.95 (2H, m), 7.59 (1H, t, J=8.0 Hz), 4.92-4.82 (1H, m), 4.17-4.10 (1H, m), 3.94-3.82 (2H, m), 3.72-3.54 (4H, m), 1.76 (3H, d, J=6.4 Hz).

Intermediate 60

(S)-3-(1-Aminoethyl)-7-fluoro-N-(2-methoxyethyl)-8-methylquinolin-2-amine bis hydrochloric acid salt Similarly, Intermediate 51 (140 mg, 0.37 mmol) and HCl (0.93 mL, 3.71 mmol; 4.0M in 1,4-dioxane) in dry 1,4-dioxane (5 mL) gave the title compound (144 mg, quantitative) as a white solid. $\delta_H$ (MeOD-d$_4$) 8.59 (1H, s), 7.96 (1H, dd, J 8.8, 5.6 Hz), 7.46 (1H, t, J=9.0 Hz), 4.96-4.86 (1H, m), 4.03-3.94 (4H, m), 3.66 (3H, s), 2.61 (3H, d, J=1.6 Hz), 1.80 (3H, d, J=6.4 Hz).

Intermediate 61

(S)-2-[3-(1-Aminoethyl)-8-chloroquinolin-2-ylamino]-N-methylacetamide bis hydrochloric acid salt Similarly, Intermediate 52 (60 mg, 0.15 mmol) and HCl (0.38 mL, 1.53 mmol; 4.0M in 1,4-dioxane) in dry 1,4-dioxane (5 mL) gave the title compound (54 mg, quantitative) as a white solid. $\delta_H$ (MeOD-d$_4$) 8.42 (1H, s), 7.92-7.87 (2H, m), 7.47 (1H, t, J=7.8 Hz), 4.94-4.84 (1H, m), 4.43 (1H, d, J=15.2 Hz), 4.30 (1H, d, J=15.6 Hz), 2.88 (3H, s), 1.81 (3H, d, J=6.4 Hz).

Intermediate 62

(S)-2-[3-(1-Aminoethyl)-7-fluoro-8-methylquinolin-2-ylamino]ethanol bis hydrochloric acid salt Similarly, Intermediate 53 (900 mg, 2.48 mmol) and HCl (6.2 mL, 24.8 mmol; 4.0M in 1,4-dioxane) in dry 1,4-dioxane (24 mL) gave the title compound (0.85 g, quantitative) as a white solid. $\delta_H$ (MeOD-d$_4$) 8.56 (1H, s), 7.93 (1H, dd, J 8.8, 5.6 Hz), 7.42 (1H, t, J=9.0 Hz), 4.94-4.85 m), 4.08-4.05 (2H, m), 3.93-3.91 (2H, m), 2.56 (3H, d, J=1.6 Hz), 1.78 (3H, d, J=6.8 Hz).

Intermediate 63

(S)-2-[3-(1-Aminoethyl)-8-chloroquinolin-2-ylamino]-N,N-dimethylacetamide bis hydrochloric acid salt Similarly, Intermediate 54 (120 mg, 0.30 mmol) and HCl (0.74 mL, 2.95 mmol; 4.0M in 1,4-dioxane) in dry 1,4-dioxane (5 mL) gave the title compound (120 mg, quantitative) as a white solid. $\delta_H$ (MeOD-d$_4$) 8.46 (1H, s), 7.87 (1H, d, J=8.0 Hz), 7.85 (1H, d, J=8.0 Hz), 7.43 (1H, t, J=8.0 Hz), 4.94-4.86 (1H, m), 4.76 (1H, d, J=12.0 Hz), 4.42 (1H, d, J=16.0 Hz), 3.10 (3H, d, J=8.0 Hz), 1.82 (3H, d, J=8.0 Hz).

Intermediate 64

(S)-3-(1-Aminoethyl)-8-chloro-N-(pyridin-2-ylmethyl)quinolin-2-amine tris hydrochloric acid salt Similarly, Intermediate 55 (100 mg, 0.24 mmol) and HCl (1.2 mL, 4.84 mmol; 4.0M in 1,4-dioxane) in dry 1,4-dioxane (5 mL) gave the title compound (143 mg, quantitative) as an off-white solid. $\delta_H$ (MeOD-d$_4$) 8.78-8.74 (1H, m), 8.55 (1H, td, J 7.92, 1.58 Hz), 8.25-8.19 (2H, m), 7.97-7.91 (1H, m), 7.73 (1H, dd, J 8.04, 1.33 Hz), 7.66 (1H, dd, J 7.61, 1.33 Hz), 7.27 (1H, t, J 7.82 Hz), 5.08 (2H, s), 4.98 (1H, q, J=6.74 Hz), 1.82 (3H, d, J=6.75 Hz).

Intermediate 65

(S)-3-(1-Aminoethyl)-8-chloro-N-(pyridin-3-ylmethyl)quinolin-2-amine tris hydrochloric acid salt Similarly, Intermediate 56 (100 mg, 0.24 mmol) and HCl (1.2 mL, 4.84 mmol; 4.0M in 1,4-dioxane) in dry 1,4-dioxane (5 mL) gave the title compound (143 mg, quantitative) as an off-white solid. $\delta_H$ (MeOD-d$_4$) 9.24 (1H, s), 8.88 (1H, d, J=8.17 Hz), 8.73 (1H, d, J=5.79 Hz), 8.11 (1H, s), 8.06 (1H, dd, J 8.11, 5.80 Hz), 7.71-7.67 (2H, m), 7.24 (1H, t, J=7.82 Hz), 1.76 (3H, d, J=6.74 Hz).

Intermediate 66

(S)-2-{[3-(1-Aminoethyl)-8-chloroquinolin-2-ylamino]methyl}pyridine 1-oxide bis hydrochloric acid salt Similarly, Intermediate 57 (100 mg, 0.23 mmol) and HCl (1.2 mL, 4.66 mmol; 4.0M in 1,4-dioxane) in dry 1,4-dioxane (5 mL) gave the title compound (103 mg, quantitative) as an off-white solid. $\delta_H$ (MeOD-d$_4$) 8.60 (1H, d, J=6.46 Hz), 8.47 (1H, s), 8.04 (1H, dd, J 7.87, 2.02 Hz), 7.92 (2H, ddd, J 10.68, 7.86, 1.32 Hz), 7.86-7.80 (1H, m), 7.72-7.65 (1H, m), 7.51 (1H, t, J=7.90 Hz), 5.20 (2H, s), 4.97 (1H, q, J=6.73 Hz), 1.78 (3H, d, J=6.73 Hz).

Intermediate 67

(S)-2-{7-Fluoro-8-methyl-3-[1-(9-{[2-(trimethylsilyl)ethoxy]methyl}-9H-purin-6-ylamino)ethyl] quinolin-2-ylamino}ethanol A mixture of Intermediate 62 (0.65 g, 1.93 mmol), Intermediate 7 (0.83 g, 2.90 mmol) and DIPEA (1.7 mL, 9.67 mmol) in n-butanol (12 mL) was heated at 120° C. under microwave irradiation for 3 h. The reaction mixture was concentrated in vacuo and the residue purified by column chromatography (SiO$_2$, 0-1% MeOH in EtOAc) to give the title compound (930 mg, 72%) as a cream solid. $\delta_H$ (CDCl$_3$) 8.49 (1H, s), 7.90 (2H, d, J=6.85 Hz), 7.48-7.39 (2H, m), 7.01 (1H, t, J=8.97 Hz), 5.93-5.78 (2H, m), 5.59 (2H, s), 3.94-3.74 (3H, m), 3.75-3.61 (3H, m), 2.54 (3H, d, J=2.26 Hz), 1.83 (3H, d, J=6.42 Hz), 1.01-0.92 (2H, m), 0.00 (9H, s).

Intermediate 68

(S)-2-{7-Fluoro-8-methyl-3-[1-(9-{[2-(trimethylsilyl)ethoxy]methyl}-9H-purin-6-ylamino)ethyl] quinolin-2-ylamino}acetaldehyde To a solution of oxalyl chloride (0.95 mL, 1.91 mmol; 2.0M in DCM) in dry DCM (10 mL) cooled to −78° C. was added dropwise dimethylsulphoxide (0.13 mL, 1.91 mmol) and the mixture stirred at −78° C. for 15 minutes. The slow addition of a solution of Intermediate 67 (650 mg, 1.27 mmol) in dry DCM (15 mL) took place and the mixture was stirred at −78° C. for 30 minutes. Triethylamine (0.88 mL, 6.36 mmol) was added dropwise and the reaction mixture was allowed to warm to 0° C. and stirred for 45 minutes. Water (30 mL) was added and the mixture was diluted with DCM (50 mL). The organic layer was separated, dried (MgSO$_4$), filtered and concentrated in vacuo. The residue was purified by column chromatography (SiO$_2$, 75-100% EtOAc in isohexane) to give the title compound (200 mg, 31%) as a yellow solid. $\delta_H$ (CDCl$_3$) 9.71 (1H, s), 8.51 (1H, s), 7.93 (2H, d, J=5.87 Hz), 7.55 (1H, br s), 7.48 (1H, dd, J 8.89, 6.14 Hz), 7.03 (1H, t, J=8.98 Hz), 5.98-5.84 (2H, m), 5.60 (2H, s), 4.24-4.17 (2H, m), 3.65 (2H, t, J=8.17 Hz), 2.48 (3H, m), 1.85 (3H, d, J=6.38 Hz), 0.96 (2H, t, J=8.17 Hz), 0.00 (9H, s).

Intermediate 69

(S)-2-{7-Fluoro-8-methyl-3-[1-(9-{[2-(trimethylsilyl)ethoxy]methyl}-9H-purin-6-ylamino)ethyl] quinolin-2-ylamino}acetic acid A solution of Intermediate 68 (250 mg, 0.49 mmol) in ethanol (10 mL) was treated with a solution of silver nitrate (210 mg, 1.22 mmol) in water (2 mL) followed by a solution of KOH in water (10 mL) and the mixture was stirred at r.t. for 30 minutes. The mixture was filtered through celite, washing with water (20 mL). The filtrate was washed with EtOAc (10 mL) and the aqueous layer was acidified to pH 3 with 2M HCl. This was extracted with DCM (2×50 mL), then the organic layers were combined, dried (MgSO$_4$), filtered and concentrated in vacuo to afford the title compound (82 mg, 32%) as a yellow solid. $\delta_H$ (CDCl$_3$) 8.51 (1H, s), 8.03 (1H, s), 8.02 (1H, br s), 7.96 (1H, s), 7.52 (1H, t, J=7.30 Hz), 7.08 (1H, t, J=9.00 Hz), 6.82-6.72 (1H, m), 5.88-5.78 (1H, m), 5.60 (2H, s), 4.35-4.22 (2H, m), 3.65 (2H, t, J=8.18 Hz), 2.53 (3H, s), 1.85 (3H, d, J=6.84 Hz), 0.96 (2H, t, J=8.14 Hz), 0.00 (9H, s), 1H exchanging.

Intermediate 70

N—[(S)-1-(2-Chloro-7-fluoro-8-methylquinolin-3-yl)ethyl]pyrazolo[1,5-a]pyrimidin-7-yl-amine To a solution of Intermediate 14 (4.0 g, 12.2 mmol) in MeOH (20 mL) was added conc. HCl (1 mL) and the mixture stirred at r.t. for 2 h. The reaction mixture was partitioned between DCM (100 mL) and 2M NaOH solution (50 mL). The organic layer was dried (MgSO$_4$), filtered and concentrated in vacuo. A portion of the resulting material (280 mg, 1.2 mmol), 7-chloropyrazolo[1,5-a]pyrimidine (310 mg, 1.9 mmol) and DIPEA (0.7 mL, 4 mmol) in n-butanol (3 mL) were combined and heated at 100° C. for 64 h. The mixture was cooled and partitioned between EtOAc (50 mL) and water (50 mL) The aqueous layer was separated, extracted into EtOAc (20 mL) and the combined organics washed with water (15 mL), brine (15 mL), separated, dried (Na$_2$SO$_4$), filtered and concentrated in vacuo. The residue was purified by column chromatography (SiO$_2$, 0-60% EtOAc in hexanes) to give the title compound (300 mg, 72%) as a pale yellow solid. $\delta_H$ (CDCl$_3$) 8.22 (1H, d, J 7.6 Hz), 8.11 (1H, s), 7.82 (1H, d, J=2.3 Hz), 7.57 (1H, dd, J 8.8, 6.1 Hz), 7.28 (1H, m), 6.06 (1H, d, J=2.0 Hz), 6.03 (1H, d, J=7.6 Hz), 5.51 (2H, m), 2.65 (3H, d, J=2.3 Hz), 1.69 (3H, d, J=6.8 Hz). LCMS (ES+) 356.2 (M+H)$^+$.

Example 1

N-Butyl-N-methyl-N-{8-methyl-3-[1-(9H-purin-6-ylamino)ethyl]quinolin-2-yl}amine To a solution of Intermediate 2 (140 mg, 0.38 mmol) in DCM (7 mL) was added TFA (3 mL) and the mixture was stirred at r.t. for 1 h. The solvent was removed in vacuo to give a golden-yellow viscous oil (100 mg). Half of this oil (50 mg, 0.19 mmol) was dissolved in n-butanol (2 mL) and to this solution was added 6-chloropurine (43 mg, 0.28 mmol) and DIPEA (0.14 mL, 0.78 mmol). The reaction mixture was heated at 140° C. in a microwave for 90 minutes. The solvent was removed in vacuo and the residue purified by preparative HPLC to give the title compound (44 mg, 75%) as a dark cream solid. $\delta_H$ (MeOD-d$_4$) 8.34 (s, 1H), 8.29 (s, 1H), 8.21 (s, 1H), 7.62 (d, J=8.0 Hz, 1H), 7.50 (d, J=6.8 Hz, 1H), 7.31 (t, J=7.6 Hz, 1H), 5.84-5.96 (m, 1H), 3.50-3.57 (m, 1H), 3.35-3.43 (m, 1H), 3.14 (s, 3H), 2.72 (s, 3H), 1.71-1.79 (m, 5H), 1.31-1.42 (m, 2H), 0.93 (t, J=7.4 Hz, 3H). LCMS (ES+) 390 (M+H)$^+$, RT 3.01 minutes (Method 2).

Example 2

N-Butyl-N-methyl-N-{8-methyl-3-[1-(1H-pyrazolo[3,4-d]pyrimidin-4-ylamino)ethyl]-quinolin-2-yl}amine The title compound was prepared in a similar manner to Example 1 using Intermediate 2 (140 mg, 0.38 mmol) and was obtained as a brown solid (45 mg, 63%) after purification by preparative HPLC. $\delta_H$ (MeOD-d$_4$) 8.35 (br s, 2H), 8.24 (s, 1H), 7.62 (d, J=8.0 Hz, 1H), 7.49 (d, J=6.8 Hz, 1H), 7.30 (t, J=7.6 Hz, 1H), 5.90-6.00 (m, 1H), 3.48-3.57 (m, 1H), 3.13 (s, 3H), 2.72 (s, 3H), 1.67-1.76 (m, 5H), 1.34-1.42 (m, 2H), 0.92 (t, J=7.3 Hz, 3H). LCMS (ES+) 390 (M+H)$^+$, RT 3.20 minutes (Method 2).

Example 3

(S)-3-[1-(9H-Purin-6-ylamino)ethyl]-N,N,8-trimethylquinolin-2-ylamine

To a solution of Intermediate 4 (100 mg, 0.3 mmol) in n-butanol (4 mL) were added dimethylamine hydrochloride (125 mg, 1.5 mmol) and DIPEA (0.28 mL, 1.5 mmol). The reaction mixture was heated at 160° C. in a microwave for 2 h. Conc. hydrochloric acid (1 mL) was added and the mixture was stirred at r.t. for 20 minutes. The mixture was poured into water (20 mL), basified with 5M NaOH solution (20 mL) and extracted with Et$_2$O (3×25 mL). The organic layers were combined, separated, dried (MgSO$_4$), filtered and the solvent removed in vacuo. The residue was dissolved in n-butanol (2.5 mL) and 6-chloro-9-[2-(trimethylsilanyl)ethoxymethyl]-9H-purine (100 mg, 0.35 mmol) and DIPEA (0.14 mL, 0.75 mmol) were added. The reaction mixture was heated at 160° C. in a microwave for 1 h. HCl (2 mL, 4M solution in 1,4-dioxane) was added and the mixture was stirred for 20 minutes. The reaction mixture was poured into water (20 mL) basified with solid Na$_2$CO$_3$ and extracted with DCM (3×25 mL). The organic layers were combined, separated, dried (MgSO$_4$), filtered and the solvent removed in vacuo. The residue was purified by preparative HPLC to give the title compound (11 mg, 7.2%) as a white solid. $\delta_H$ (CDCl$_3$) 8.35 (s, 1H), 8.05 (s, 1H), 7.95 (s, 1H), 7.47 (d, J=8.8 Hz, 1H), 7.40 (d, J=8.8 Hz, 1H), 7.21 (t, J=8.8 Hz, 1H), 6.52 (br s, 1H), 5.92 (br s, 1H), 3.08 (s, 6H), 2.71 (s, 3H), 1.65 (d, J=6.4 Hz, 1H). LCMS (ES+) 348 (M+H)$^+$, RT 2.17 minutes (Method 2).

Example 4

(S)—N-Allyl-N,8-dimethyl-3-[1-(9H-purin-6-ylamino)ethyl]quinolin-2-amine

Intermediate 8 (60 mg, 0.12 mmol) in THF (1 mL) was treated with 1.0M tetrabutylammonium fluoride (0.6 mL, 0.6 mmol) and heated at 50° C. for 16 h. The reaction mixture was concentrated in vacuo and purified by column chromatography [SiO$_2$, 7M NH$_3$/MeOH (10%) in EtOAc] to give the title compound (31.9 mg, 71%) as a white solid. $\delta_H$ (CDCl$_3$) 8.37 (1H, s), 8.03 (1H, s), 7.97 (1H, s), 7.43 (1H, d, J=8.04 Hz), 7.40 (1H, d, J=7.03 Hz), 7.18 (1H, t, J=7.52 Hz), 6.55 (1H, br d, J=7.12 Hz), 6.16-6.03 (1H, m), 5.85 (1H, br s), 5.38 (1H, d, J=17.21 Hz), 5.20 (1H, d, J=10.22 Hz), 4.32 (1H, dd, J 15.51, 5.41 Hz), 3.87 (1H, dd, J 15.48, 6.00 Hz), 3.04 (3H, s), 2.70 (3H, s), 1.62 (3H, d, J=6.68 Hz), 1H under H$_2$O. LCMS (ES+) 374 (M+H)$^+$, RT 15.05 minutes (Method 5).

Example 5

(S)—N,N-Diethyl-7-fluoro-3-[1-(9H-purin-6-ylamino)ethyl]quinolin-2-amine

To a solution of Intermediate 15 (0.32 g, 1.0 mmol) in n-butanol (2 mL) were added diethylamine (80 mg, 1.1 mmol) and DIPEA (0.42 mL, 2.33 mmol). The reaction mixture was heated at 110° C. for 18 h and then concentrated in vacuo. The residue was purified by column chromatography (SiO$_2$, 0-3% MeOH in DCM) to give a pale orange oil (97 mg, 55%). To a solution of this oil in MeOH (2 mL) was added HCl (1.0 mL, 4.0M solution in 1,4-dioxane). The reaction mixture was stirred for 2 h and concentrated in vacuo to give a beige solid (150 mg, 48%). To a solution of this solid (0.1 g, 0.38 mmol) in n-butanol (2 mL) were added 6-chloropurine (66 mg, 0.42 mmol) and DIPEA (100 mg, 0.78 mmol). The reaction mixture was heated at 110° C. for 18 h and then concentrated in vacuo. The residue was purified by preparative HPLC to give the title compound (30 mg, 21%) as a white solid. $\delta_H$ (CDCl$_3$) 8.35 (1H, s), 8.03 (1H, s), 7.96 (1H, s), 7.57 (1H, dd, J 8.88, 6.15 Hz), 7.47 (1H, dd, J 10.62, 2.57 Hz), 7.08 (1H, td, J 8.62, 2.58 Hz), 6.50 (1H, s), 5.81 (1H, s), 3.60-3.40 (4H, m), 1.64 (3H, d, J=6.66 Hz), 1.21 (6H, t, J=6.98 Hz). LCMS (ES+) 380 (M+H)$^+$, RT 19.26 minutes (Method 6).

Example 6

(S)—N$^2$-{1-[2-(Diethylamino)-7-fluoroquinolin-3-yl]ethyl}-[1,3,5]triazine-2,4-diamine Similarly Intermediate 15 (0.122 g, 0.38 mmol), 2-amino-4-chloro-[1,3,5]triazine (0.055 mg, 0.43 mmol) and DIPEA (100 mg, 0.78 mmol) in n-butanol (2 mL) gave the title compound (33.6 mg, 25%) as a white solid. $\delta_H$ (CDCl$_3$) 8.10 (1H, s), 7.92 (1H, s), 7.59 (1H, dd, J 8.88, 6.16 Hz), 7.47 (1H, dd, J 10.60, 2.56 Hz), 7.10 (1H, td, J 8.62, 2.58 Hz), 6.14-4.89

(4H, m), 3.54-3.46 (2H, m), 3.42-3.29 (2H, m), 1.49 (3H, d, J=6.70 Hz), 1.18 (6H, t, J=6.91 Hz). LCMS (ES+) 356 (M+H)$^+$, RT 3.04 minutes (Method 1).

Example 7

(S)—$N^2$-{1-[2-(Diethylamino)-7-fluoroquinolin-3-yl]ethyl}-6-methyl-[1,3,5]triazine-2,4-diamine Similarly, Intermediate 15 (0.073 g, 0.23 mmol), 2-amino-4-chloro-6-methyl-[1,3,5]triazine (36 mg, 0.25 mmol) and DIPEA (100 mg, 0.78 mmol) in n-butanol (2 mL) gave the title compound (11.2 mg, 14%) as a white solid. $\delta_H$ (CDCl$_3$) 7.91 (1H, s), 7.59 (1H, dd, J 8.86, 6.14 Hz), 7.47 (1H, dd, J 10.62, 2.57 Hz), 7.13-7.06 (1H, m), 5.74-5.06 (4H, m), 3.53 (2H, s), 3.39 (2H, s), 2.39-2.04 (3H, m), 1.46 (3H, s), 1.19 (6H, t, J 7.01 Hz). LCMS (ES+) 370 (M+H)$^+$, RT 3.33 minutes (Method 1).

Example 8

(S)—$N^2$-{1-[7-Fluoro-2-(2-methoxyethylamino)quinolin-3-yl]ethyl}-6-methyl-[1,3,5]-triazine-2,4-diamine To a solution of Intermediate 17 (35 mg, 0.13 mmol) in n-butanol (2 mL) were added 2-amino-4-chloro-6-methyl-[1,3,5]triazine (23 mg, 0.16 mmol) and DIPEA (45 mg, 0.35 mmol). The reaction mixture was heated at 110° C. for 18 h and then concentrated in vacuo. The residue was purified by preparative HPLC to give the title compound (12.3 mg, 25%) as a white solid. $\delta_H$ (CDCl$_3$) 7.78 (1H, d, J=1.68 Hz), 7.52 (1H, dd, J 8.79, 6.30 Hz), 7.29 (1H, dd, J 10.95, 2.50 Hz), 6.95 (1H, td, J 8.62, 2.55 Hz), 6.33 (1H, br d, J=8.70 Hz), 5.28 (1H, br t, J=7.86 Hz), 4.03 (1H, br s), 3.79 (2H, br s), 3.62-3.70 (2H, m), 3.53-3.61 (2H, m), 3.45 (3H, s), 2.22 (3H, s), 1.65 (3H, d, J=6.83 Hz). LCMS (ES+) 372 (M+H)$^+$, RT 2.33 minutes (Method 1).

Example 9

(S)-7-Fluoro-N-(2-methoxyethyl)-3-[1-(9H-purin-6-ylamino)ethyl]quinolin-2-amine

Similarly, Intermediate 17 (35 mg, 0.133 mmol), 6-chloropurine (25 mg, 0.16 mmol) and DIPEA (45 mg, 0.35 mmol) in n-butanol (2 mL) gave the title compound (7.6 mg, 15%) as a white solid. $\delta_H$ (CDCl$_3$) 8.48 (1H, s), 7.92 (1H, s), 7.85 (1H, s), 7.55 (1H, dd, J 8.80, 6.28 Hz), 7.30 (1H, dd, J 10.99, 2.54 Hz), 6.95 (1H, td, J 8.61, 2.57 Hz), 6.71 (1H, br s), 6.13 (1H, br d, J=9.19 Hz), 5.84 (1H, br s), 3.80-3.70 (2H, m), 3.62-3.48 (2H, m), 3.22 (3H, s), 1.78 (3H, d, J=6.77 Hz). LCMS (ES+) 382 (M+H)$^+$, RT 6.96 minutes (Method 8).

Example 10

(S)-7-Fluoro-N-(3-methoxypropyl)-3-[1-(9H-purin-6-ylamino)ethyl]quinolin-2-amine Similarly, Intermediate 18 (60 mg, 0.21 mmol), 6-chloropurine (37 mg, 0.24 mmol) and DIPEA (100 mg, 0.78 mmol) in n-butanol (2 mL) gave the title compound (13.3 mg, 16%) as a pale yellow solid. $\delta_H$ (CDCl$_3$) 8.44 (1H, s), 7.96 (1H, s), 7.83 (1H, s), 7.51 (1H, dd, J 8.77, 6.14 Hz), 7.31 (1H, dd, J 11.00, 2.53 Hz), 6.93 (1H, td, J 8.60, 2.57 Hz), 6.63 (2H, d, J=9.76 Hz), 5.78 (1H, s), 3.71-3.53 (2H, m), 3.48-3.33 (2H, m), 3.25 (3H, s), 1.97-1.80 (2H, m), 1.77 (3H, d, J=6.71 Hz). LCMS (ES+) 396 (M+H)$^+$, RT 7.01 minutes (Method 8).

Example 11

(S)—$N^2$-{1-[2-(Diethylamino)-7-fluoro-8-methylquinolin-3-yl]ethyl}-6-methyl-[1,3,5]-triazine-2,4-diamine Similarly, Intermediate 19 (70 mg, 0.25 mmol), 2-amino-4-chloro-6-methyl-[1.3.5]triazine (40 mg, 0.27 mmol) and DIPEA (100 mg, 0.78 mmol) in n-butanol (2 mL) gave the title compound (30 mg, 30%) as a white solid. $\delta_H$ (CDCl$_3$) 7.87 (1H, s), 7.43 (1H, t, J=7.31 Hz), 7.07 (1H, t, J=9.01 Hz), 5.62 (1H, s), 5.49 (1H, s), 5.06 (2H, s), 3.57-3.48 (2H, m), 3.45-3.36 (2H, m), 2.59 (3H, d, J=2.40 Hz), 2.27 (2H, s), 2.18 (1H, s), 1.46 (3H, d, J=6.80 Hz), 1.22 (6H, t, J=6.99 Hz). LCMS (ES+) 384 (M+H)$^+$, RT 3.73 minutes (Method 1).

Example 12

(S)-1-(4-{3-[1-(4-Amino-[1,3,5]triazin-2-ylamino)ethyl]-8-chloroquinolin-2-ylamino}piperidin-1-yl)ethanone A mixture of Intermediate 25 (62 mg, 0.18 mmol), 2-amino-4-chloro-[1,3,5]-triazine (47 mg, 0.36 mmol) and DIPEA (0.15 mL, 0.89 mmol) in 1,4-dioxane (3 mL) was heated at 130° C. under microwave irradiation for 1.5 h. The reaction mixture was concentrated in vacuo and the residue purified by preparative HPLC to give the title compound (28.7 mg, 36%). $\delta_H$ (DMSO-d$_6$) 8.14-7.90 (2H, m), 7.73-7.64 (3H, m), 7.17 (1H, t, J=7.75 Hz), 7.28-6.72 (2H, m), 6.65-6.54 (1H, m), 5.33 (1H, br s), 4.33 (2H, br s), 3.92-3.79 (1H, m), 3.23 (1H, t, J=13.52 Hz), 2.92-2.70 (1H, m), 2.30-1.70 (5H, m), 1.56 (3H, s), 1.50-1.33 (2H, m). LCMS (ES+) 441 (M+H)$^+$, RT 7.85 minutes (Method 5).

Example 13

(S)-8-Chloro-N,N-diethyl-3-[1-(9H-purin-6-ylamino)ethyl]quinolin-2-amine

A solution of Intermediate 26 (60 mg, 0.16 mmol) and hydrogen chloride (0.8 mL, 3.17 mmol; 4.0M in 1,4-dioxane) in 1,4-dioxane (5 mL) was stirred at r.t. overnight. The reaction mixture was concentrated in vacuo to give a yellow solid (64 mg). A solution of this solid (64 mg, 0.18 mmol) in n-butanol (5 mL) with DIPEA (0.2 mL, 0.91 mmol) and 6-bromopurine (54 mg, 2.7 mmol) was heated at 80° C. overnight and then heated at 120° C. for 10 h. The reaction mixture was concentrated in vacuo and purified by preparative HPLC to give the title compound (25 mg, 34%) as a beige solid. $\delta_H$ (MeOD-d$_4$) 8.26-8.15 (3H, m), 8.13 (1H, s), 7.67 (1H, dd, J 7.50, 1.39 Hz), 7.64 (1H, dd, J 8.08, 1.41 Hz), 7.26 (1H, t, J 7.79 Hz), 5.85 (1H, s), 3.67-3.51 (5H, m), 1.65 (3H, d, J=6.71 Hz), 1.27 (6H, t, J=6.97 Hz). LCMS (ES+) 396 (M+H)$^+$, RT 16.58 minutes (Method 5).

Example 14

(S)-8-Chloro-N-(2-methoxyethyl)-3-[1-(9H-purin-6-ylamino)ethyl]quinolin-2-amine

A solution of Intermediate 32 (50 mg, 0.14 mmol), 6-bromopurine (42 mg, 0.21 mmol) and DIPEA (0.13 mL, 0.71 mmol) in n-butanol (1.5 mL) was heated at 120° C. in the microwave for 3 h. The reaction mixture was concentrated in vacuo and purified by preparative HPLC to afford the title compound (9 mg, 16%) as a yellow solid. $\delta_H$ (MeOD-d$_4$) 8.35 (1H, s), 8.10 (1H, s), 8.04 (1H, s), 7.60 (2H, d, J 7.75 Hz), 7.12 (1H, t, J=7.74 Hz), 5.80 (1H, br s), 3.89-3.73 (2H, m), 3.72-3.56 (2H, m), 3.22 (3H, s), 1.77 (3H, d, J=6.78 Hz), 3 NH not visible. LCMS (ES+) 398 (M+H)$^+$, RT 3.01 minutes (Method 1).

Example 15

(S)-8-Chloro-N-(2-methoxyethyl)-N-methyl-3-[1-(9H-purin-6-ylamino)ethyl]quinolin-2-amine Similarly, Intermediate 33 (45 mg, 0.12 mmol), 6-bromopurine (37 mg, 0.18 mmol) and DIPEA (0.13 mL, 0.71 mmol) in n-butanol (1.5 mL) gave the title compound (9 mg, 18%) as an orange-yellow solid. $\delta_H$ (MeOD-d$_4$) 8.29-8.18 (2H, m), 8.13 (1H, s), 7.68 (1H, dd, J 7.49, 1.39 Hz), 7.65 (1H, dd, J 8.10, 1.38 Hz), 7.26 (1H, t, J=7.80 Hz), 5.92 (1H, s), 3.86-3.68 (4H, m), 3.35 (3H, s), 3.23 (3H, s), 1.65 (3H, d, J=6.70 Hz), 2 NH not visible. LCMS (ES+) 412 (M+H)$^+$, RT 2.31 minutes (Method 2).

Example 16

(S)-8-Chloro-N-methyl-3-[1-(9H-purin-6-ylamino)ethyl]quinolin-2-amine

Similarly, Intermediate 34 (50 mg, 0.16 mmol), 6-bromopurine (48 mg, 0.24 mmol) and DIPEA (0.14 mL, 0.81 mmol) in n-butanol (1.5 mL) gave the title compound (12 mg, 21%) as a dark cream solid. $\delta_H$ (MeOD-d$_4$) 8.30 (1H, s), 8.12 (1H, s), 7.97 (1H, s), 7.59 (1H, dd, J 7.56, 1.40 Hz), 7.55 (1H, dd, J 7.98, 1.41 Hz), 7.10 (1H, t, J=7.77 Hz), 5.71 (1H, s), 3.14 (3H, s), 1.73 (3H, d, J=6.81 Hz). LCMS (ES+) 354 (M+H)$^+$, RT 2.00 minutes (Method 2).

Example 17

8-Chloro-3-[(S)-1-(9H-purin-6-ylamino)ethyl]-N-{[(R)-tetrahydrofur-2-yl]methyl}-quinolin-2-amine Similarly, Intermediate 35 (80 mg, 0.21 mmol), 6-bromopurine (63 mg, 0.32 mmol) and DIPEA (0.19 mL, 1.06 mmol) in n-butanol (2 mL) gave the title compound (30 mg, 34%) as a yellow solid. $\delta_H$ (MeOD-d$_4$) 8.25 (1H, s), 7.99 (1H, s), 7.94 (1H, s), 7.53-7.46 (2H, m), 7.02 (1H, t, J=7.77 Hz), 5.71 (1H, br s), 4.16-4.08 (1H, m), 3.74-3.56 (2H, m), 3.52 (2H, t, J=6.75 Hz), 1.88-1.76 (1H, m), 1.75-1.60 (5H, m), 1.56-1.46 (1H, m), 3 NH not visible. LCMS (ES+) 424 (M+H)$^+$, RT 7.40 minutes (Method 8).

Example 18

8-Chloro-3-[(S)-1-(9H-purin-6-ylamino)ethyl]-N-{[(S)-tetrahydrofur-2-yl]methyl}-quinolin-2-amine A solution of Intermediate 31 (80 mg, 0.20 mmol) and hydrogen chloride (1.0 mL, 3.94 mmol; 4.0M in 1,4-dioxane) in 1,4-dioxane (5 mL) was stirred at r.t. overnight. The reaction mixture was concentrated in vacuo to give an off-white semi-solid (75 mg). A solution of this material (75 mg, 0.20 mmol) in n-butanol (2 mL) with DIPEA (0.18 mL, 0.99 mmol) and 6-bromopurine (59 mg, 3.0 mmol) was heated at 130° C. in the microwave for 2 h. The reaction mixture was concentrated in vacuo and purified by preparative HPLC to give the title compound (14 mg, 17%) as a fawn solid. $\delta_H$ (MeOD-d$_4$) 8.35 (1H, s), 8.10 (1H, s), 8.04 (1H, s), 7.60 (2H, d, J=7.77 Hz), 7.12 (1H, t, J=7.77 Hz), 5.80 (1H, br s), 4.16-4.09 (1H, m), 3.84-3.76 (2H, m), 3.73-3.60 (2H, m), 2.00-1.80 (3H, m), 1.78 (3H, d, J=6.79 Hz), 1.77-1.65 (1H, m), 3 NH not visible. LCMS (ES+) 424 (M+H)$^+$, RT 7.41 minutes (Method 8).

Example 19

(S)-8-Chloro-N-(2-methoxyethyl)-3-{1-[2-(methylthio)pyrazolo[1,5-a][1,3,5]triazin-4-ylamino]ethyl}quinolin-2-amine To a solution of Intermediate 27 (310 mg, 0.82 mmol) in DCM (3 mL) was added TFA (1 mL). The reaction mixture was stirred for 2 h and concentrated in vacuo. The residue was dissolved in MeOH and passed though an SCX cartridge [eluents: MeOH, MeOH/7N NH$_3$ (10:1)] to give crude deprotected amine. To a solution of the amine in dry THF (5 mL) were added DIPEA (0.36 mL, 2 mmol) and 4-chloro-2-(methylthio)-pyrazolo[1,5-a][1,3,5]triazine (196 mg, 0.98 mmol). The reaction mixture was stirred for 6 h and concentrated in vacuo. The residue was partitioned between DCM (50 mL) and water (10 mL). The organic layer was washed with water (2×10 mL) and brine, dried (MgSO$_4$) and concentrated in vacuo. Purification by column chromatography (SiO$_2$, 0-20% EtOAc in isohexane) afforded the title compound (213 mg, 58%) as a clear glass. $\delta_H$ (CDCl$_3$) 7.86 (1H, s), 7.84 (1H, d, J=2.11 Hz), 7.64 (1H, dd, J 7.56, 1.38 Hz), 7.51 (1H, dd, J 7.96, 1.39 Hz), 7.11 (1H, t, J=7.76 Hz), 6.50 (1H, d, J=9.57 Hz), 6.25 (1H, d, J=2.10 Hz), 6.21 (1H, t, J=5.31 Hz), 5.68-5.58 (1H, m), 3.96-3.87 (1H, m), 3.85-3.76 (1H, m), 3.67-3.53 (2H, m), 3.16 (3H, s), 2.59 (3H, s), 1.83 (3H, d, J=6.76 Hz). LCMS (ES+) 444 (M+H)$^+$, RT 3.84 minutes (Method 1).

Example 20

(S)-8-Chloro-N-(2-methoxyethyl)-3-{1-[2-(methylsulfonyl)pyrazolo[1,5-a][1,3,5]triazin-4-ylamino]ethyl}quinolin-2-amine To a solution of Example 19 (160 mg, 0.36 mmol) in DCM (4 mL) was added MCPBA (125 mg, 0.72 mmol). The reaction mixture was stirred for 3 h and concentrated in vacuo. Purification by preparative HPLC followed by trituration with Et$_2$O gave the title compound (60 mg, 35%) as a white solid. $\delta_H$ (CDCl$_3$) 8.07 (1H, d, J=2.14 Hz), 7.92 (1H, s), 7.65 (1H, dd, J 7.54, 1.35 Hz), 7.53 (1H, dd, J 7.99, 1.35 Hz), 7.13 (1H, t, J=7.77 Hz), 6.85 (1H, br s), 6.67 (1H, d, J=2.14 Hz), 6.10 (1H, br s), 5.81 (1H, br t, J=7.06 Hz), 4.04-3.97 (1H, m), 3.74-3.65 (1H, m), 3.59-3.47 (2H, m), 3.37 (3H, s), 2.96 (3H, s), 1.91 (3H, d, J=6.75 Hz). LCMS (ES+) 476 (M+H)$^+$, RT 3.00 minutes (Method 1).

Example 21

(S)-8-Chloro-N-(2-methoxyethyl)-3-[1-(pyrazolo[1,5-a][1,3,5]triazin-4-ylamino)ethyl]-quinolin-2-amine To a solution of Example 20 (60 mg, 0.12 mmol) in EtOH/CHCl$_3$ (1:1; 1.2 mL) was added portionwise NaBH$_4$ (9.6 mg, 0.25 mmol). After 10 minutes of stirring, water (1 mL) was added and the reaction mixture was concentrated in vacuo. The residue was partitioned between DCM and water. The organic layer was washed with water (2×10 mL) and brine (10 mL), dried (MgSO$_4$) and concentrated in vacuo. The resulting gum was freeze-dried to give the title compound (30 mg, 60%) as an off-white solid. δ$_H$(CDCl$_3$) 8.28 (1H, s), 7.96 (1H, d, J=2.14 Hz), 7.90 (1H, s), 7.65 (1H, dd, J 7.56, 1.39 Hz), 7.52 (1H, dd, J 7.97, 1.41 Hz), 7.12 (1H, t, J=7.76 Hz), 6.59 (1H, br d, J=9.42 Hz), 6.48-6.46 (2H, m), 5.75-5.66 (1H, m), 3.94-3.85 (1H, m), 3.83-3.74 (1H, m), 3.65-3.51 (2H, m), 3.18 (3H, s), 1.86 (3H, d, J=6.80 Hz). LCMS (ES+) 398 (M+H)$^+$, RT 19.67 minutes (Method 6).

Example 22

(S)-8-Chloro-N-cyclopropyl-3-[1-(9H-purin-6-ylamino)ethyl]quinolin-2-amine

Intermediate 23 (200 mg, 0.58 mmol), cyclopropylamine (0.2 mL, 2.93 mmol), DIPEA (0.52 mL, 2.93 mmol) and NMP (2 mL) were combined in a sealed tube and heated to 140° C. overnight. After cooling, the mixture was dissolved in a 1:1 mixture of Et$_2$O and EtOAc (100 mL) and washed with saturated brine (3×25 mL). The organic layer was dried (MgSO$_4$), filtered and concentrated in vacuo. Purification by column chromatography (SiO$_2$, 10% EtOAc in isohexane) gave a yellow gum (68 mg, 32%). LCMS (ES+) 362, 364 (M+H)$^+$. The yellow gum (68 mg, 0.19 mmol) was dissolved in DCM (3 mL) and TFA (2 mL) and the solution obtained was left to stand at r.t. for 2 h. The excess solvent was removed in vacuo and azeotroped with toluene to give a residue (60 mg). To this was added 6-chloropurine (92 mg, 0.37 mmol), DIPEA (0.22 mL, 1.25 mmol) and NMP (2 mL) and the reaction mixture was heated under microwave irradiation to 150° C. for 1 h. After cooling, the mixture was dissolved in a 1:1 mixture of Et$_2$O and EtOAc (100 mL) and washed with saturated brine (3×25 mL) The organic layer was dried (MgSO$_4$), filtered and concentrated in vacuo. Purification by preparative HPLC gave the title compound (6 mg, 6%) as a light yellow solid. δ$_H$ (DMSO-d$_6$) 8.37-8.14 (2H, m), 8.19 (1H, s), 8.00 (1H, s), 7.67-7.63 (2H, m), 7.37 (1H, d, J=3.94 Hz), 7.15 (1H, t, J=7.75 Hz), 5.66 (1H, br s), 3.22-3.12 (1H, m), 1.62 (3H, d, J=6.72 Hz), 0.83-0.72 (2H, m), 0.56-0.48 (2H, m). LCMS (ES+) 380 (M+H)$^+$, RT 7.09 minutes (Method 5).

Example 23

(R)-5-{3-[(S)-1-(4-Amino-6-methyl[1,3,5]triazin-2-ylamino)ethyl]-8-chloroquinolin-2-ylamino}piperidin-2-one Intermediate 23 (250 mg, 0.73 mmol), (R)-5-aminopiperidin-2-one (275 mg, 1.83 mmol), DIPEA (0.81 mL, 3.65 mmol) and NMP (1.5 mL) were combined in a sealed tube and heated to 140° C. for 48 h. After cooling, the mixture was dissolved in a 1:1 mixture of Et$_2$O and EtOAc (200 mL) and washed with saturated brine (3×50 mL). The organic layer was dried (MgSO$_4$), filtered and concentrated in vacuo. Purification by column chromatography (SiO$_2$, 0-8% MeOH in DCM) gave a yellow oil (100 mg, 33%). LCMS (ES+) 419, 421 (M+H)$^+$. The yellow oil (100 mg, 0.24 mmol) was dissolved in DCM (3 mL) and TFA (2 mL) and the solution was left to stand at r.t. for 2 h. The excess solvent was removed in vacuo and the residue azeotroped with toluene. Purification by ion exchange chromatography (SCX cartridge eluting with NH$_3$ in MeOH) gave a cream solid (50 mg, 66%). LCMS (ES+) 319, 321 (M+H)$^+$. The cream solid (50 mg, 0.16 mmol), 2-amino-4-chloro-6-methyl-[1,3,5]triazine (27 mg, 0.19 mmol), DIPEA (0.086 mL, 0.48 mmol) and NMP (1.5 mL) were combined and heated under microwave irradiation to 150° C. for 1 h. After cooling, the mixture was dissolved in a 1:1 mixture of Et$_2$O and EtOAc (100 mL) and washed with saturated brine (3×10 mL). The organic layer was dried (MgSO$_4$), filtered and concentrated in vacuo. Purification by preparative HPLC gave the title compound (9.3 mg, 14%) as a brown glass. δ$_H$ (CDCl$_3$) 7.82 (1H, s), 7.66 (1H, dd, J 7.56, 1.36 Hz), 7.53 (1H, dd, J 8.02, 1.39 Hz), 7.15 (1H, t, J=7.76 Hz), 6.89 (1H, br s), 6.69 (1H, s), 5.44-5.35 (2H, m), 5.30-5.23 (1H, m), 4.13-4.08 (1H, m), 4.04-3.97 (1H, m), 3.52-3.44 (1H, m), 2.40-2.32 (2H, m), 2.30 (3H, s), 2.29-2.19 (1H, m), 2.03-1.95 (1H, m), 1.69 (3H, d, J=6.71 Hz). LCMS (ES+) 427 (M+H)$^+$, RT 15.05 minutes (Method 6).

Example 24

(S)-1-(4-{8-Chloro-3-[1-(9H-purin-6-ylamino)ethyl]quinolin-2-ylamino}piperidin-1-yl)ethanone Intermediate 23 (200 mg, 0.58 mmol), 1-(4-aminopiperidin-1-yl)ethanone (416 mg, 2.93 mmol), DIPEA (0.52 mL, 2.93 mmol) and NMP (2 mL) were combined in a sealed tube and heated to 140° C. overnight. After cooling, the mixture was dissolved in a 1:1 mixture of Et$_2$O and EtOAc (100 mL) and washed with saturated brine (3×25 mL). The organic layer was dried (MgSO$_4$), filtered and concentrated in vacuo. Purification by column chromatography (SiO$_2$, 50% EtOAc in isohexane) gave a yellow gum (140 mg, 54%). LCMS (ES+) 447, 449 (M+H)$^+$. The yellow gum (140 mg, 0.31 mmol) was dissolved in DCM (6 mL) and TFA (4 mL) and the solution was left to stand at r.t. for 2 h. The excess solvent was removed in vacuo and the residue azeotroped with toluene. Purification by ion exchange chromatography (SCX cartridge eluting with NH$_3$ in MeOH) gave a yellow gum (100 mg, 90%). LCMS (ES+) 347, 349 (M+H)$^+$. The yellow gum (55 mg, 0.16 mmol), 6-chloropurine (47 mg, 0.19 mmol), DIPEA (0.086 mL, 0.48 mmol) and NMP (1.5 mL) were combined and heated under microwave irradiation to 150° C. for 1 h. After cooling, the mixture was dissolved in a 1:1 mixture of Et$_2$O and EtOAc (100 mL) and washed with saturated brine (3×25 mL). The organic layer was dried (MgSO$_4$), filtered and concentrated in vacuo. Purification by preparative HPLC gave the title compound (15.8 mg, 21%) as a light brown solid. δ$_H$(CDCl$_3$) 8.37 (1H, s), 8.08 (1H, s), 7.97 (1H, s), 7.68 (1H, dd, J 7.52, 1.33 Hz), 7.55 (1H, dd, J 8.09, 1.35 Hz), 7.26-7.22 (1H, m), 6.34 (1H, br s), 5.83 (1H, br s), 5.48 (1H, d, J=7.91 Hz), 4.11-4.00 (2H, m), 3.76-3.67 (1H, m), 3.51-3.41 (1H, m), 3.05 (1H, t, J=11.81 Hz), 2.19-2.05 (2H, m), 2.01 (3H, s), 1.93-1.78 (2H, m), 1.73-1.61 (4H, m). LCMS (ES+) 465 (M+H)$^+$, RT 2.47 minutes (Method 2).

Example 25

(S)-5-{8-Chloro-3-[(S)-1-(9H-purin-6-ylamino)ethyl]quinolin-2-ylamino}piperidin-2-one Intermediate 23 (200 mg, 0.58 mmol), (S)-5-aminopiperidin-2-one (220 mg, 1.46 mmol), DIPEA (0.52 mL, 2.93 mmol) and NMP (1.5 mL) were combined in a sealed tube and heated to 140° C. for 72 h. After cooling, the mixture was dissolved in a 1:1 mixture of Et$_2$O and EtOAc (200 mL) and washed with saturated brine (3×50 mL). The organic layer was dried (MgSO$_4$), filtered and concentrated in vacuo. Purification by column chromatography (0-5% MeOH in DCM) gave a yellow gum (65 mg, 35%). LCMS (ES+) 319, 321 (M+H)$^+$. The yellow gum (65 mg, 0.20 mmol), 6-chloropurine (60 mg, 0.24 mmol), DIPEA (0.110 mL, 0.61 mmol) and NMP (1.5 mL) were combined and heated under microwave irradiation to 150° C. for 1 h. After cooling, the mixture was dissolved in a 1:1 mixture of Et$_2$O and EtOAc (100 mL) and washed with saturated brine (3×10 mL). The organic layer was dried (MgSO$_4$), filtered and concentrated in vacuo. Purification by preparative HPLC gave the title compound (7.2 mg, 8%) as a yellow solid. $\delta_H$ (DMSO-d$_6$) 8.26-8.20 (2H, m), 8.16 (1H, s), 7.98 (1H, s), 7.71 (1H, s), 7.63-7.57 (2H, m), 7.36 (1H, t, J=5.43 Hz), 7.10 (1H, t, J=7.75 Hz), 5.70 (1H, br s), 3.94 (1H, br s), 3.67-3.56 (2H, m), 2.20-1.99 (3H, m), 1.84-1.80 (1H, m), 1.60 (3H, d, J=6.63 Hz). LCMS (ES+) 437 (M+H)$^+$, RT 7.8 minutes (Method 5).

Example 26

2-(N'-{3-[(4-Amino-6-methyl-[1,3,5]triazin-2-yloxy) methyl]-8-methylquinolin-2-yl}-N'-methylamino)-N, N-dimethylacetamide (2-Chloro-8-methylquinolin-3-yl)methanol (250 mg, 1.13 mmol), N,N-dimethyl-2-(methylamino)acetamide (658 mg, 5.66 mmol), DIPEA (1 mL, 5.66 mmol) and NMP (3 mL) were combined in a sealed tube and heated to 140° C. for 5 h. After cooling, the mixture was dissolved in a 1:1 mixture of Et$_2$O and EtOAc (100 mL) and washed with saturated brine (3×25 mL). The organic layer was dried (MgSO$_4$), filtered and concentrated in vacuo. Purification by column chromatography (SiO$_2$, 0-5% MeOH in DCM) gave a yellow solid (195 mg, 60%). LCMS (ES+) 288 (M+H)$^+$. To the yellow solid (90 mg, 0.31 mmol) in 1,4-dioxane (3 mL) was added NaH (31 mg, 0.78 mmol; 60% dispersion in mineral oil). The reaction mixture was stirred at r.t. for 5 minutes. 2-Amino-4-chloro-6-methyl-[1,3,5]triazine (50 mg, 0.34 mmol) was added and the mixture was heated in a sealed tube at 80° C. overnight. After cooling, the mixture was diluted with H$_2$O (10 mL) and extracted with DCM (3×20 mL) The combined organic layers were dried (MgSO$_4$), filtered and concentrated in vacuo. Purification by column chromatography (0-5% MeOH in DCM) gave the title compound (25 mg, 21%) as an off-white solid. $\delta_H$ (CDCl$_3$) 8.14 (1H, s), 7.50 (1H, d, J=8.07 Hz), 7.41 (1H, d, J=7.06 Hz), 7.18 (1H, t, J 7.57 Hz), 5.56 (2H, s), 4.32 (2H, s), 3.18 (3H, s), 3.13 (3H, s), 2.97 (3H, s), 2.61 (3H, s), 2.39 (3H, s). LCMS (ES+) 396 (M+H)$^+$, RT 2.76 minutes (Method 1).

Example 27

2-(N'-{3-[(4-Amino-[1,3,5]triazin-2-yloxy)methyl]-8-methylquinolin-2-yl}-N'-methyl-amino)-N,N-dimethylacetamide (2-Chloro-8-methylquinolin-3-yl)methanol (250 mg, 1.13 mmol), N,N-dimethyl-2-(methylamino)acetamide (658 mg, 5.66 mmol), DIPEA (1 mL, 5.66 mmol) and NMP (3 mL) were combined in a sealed tube and heated to 140° C. for 5 h. After cooling, the mixture was dissolved in a 1:1 mixture of Et$_2$O and EtOAc (100 mL) and washed with saturated brine (3×25 mL). The organic layer was dried (MgSO$_4$), filtered and concentrated in vacuo. Purification by chromatography (0-5% MeOH in DCM) gave a yellow solid (195 mg, 60%). LCMS (ES+) 288 (M+H)$^+$. To the yellow solid (90 mg, 0.31 mmol) in 1,4-dioxane (3 mL) was added NaH (31 mg, 0.78 mmol; 60% dispersion in mineral oil). The reaction mixture was stirred at r.t. for 5 minutes. 2-Amino-4-chloro-[1,3,5] triazine (45 mg, 0.34 mmol) was added and the mixture was heated in a sealed tube at 80° C. overnight. After cooling, the mixture was diluted with water (10 mL) and extracted with DCM (3×20 mL). The combined organic layers were dried (MgSO$_4$), filtered and concentrated in vacuo. Purification by column chromatography (SiO$_2$, 0-5% MeOH in DCM) gave the title compound (28 mg, 24%) as a white solid. $\delta_H$ (DMSO-d$_6$) 8.35 (1H, s), 8.20 (1H, s), 7.66-7.62 (3H, m), 7.47 (1H, d, J=6.99 Hz), 7.22 (1H, t, J 7.52 Hz), 5.48 (2H, s), 4.35 (2H, s), 3.20 (3H, s), 3.05 (3H, s), 2.86 (3H, s), 3H under H$_2$O. LCMS (ES+) 382 (M+H)$^+$, RT 3.07 minutes (Method 1).

Example 28

(S)-1-(4-{8-Methyl-3-[1-(9H-purin-6-ylamino)ethyl] quinolin-2-ylamino}piperidin-1-yl)ethanone Intermediate 37 (150 mg, 0.47 mmol), 1-(4-aminopiperidin-1-yl)ethanone (332 mg, 2.34 mmol), DIPEA (0.42 mL, 2.34 mmol) and NMP (3 mL) were combined in a sealed tube and heated to 140° C. overnight. After cooling, the mixture was dissolved in a 1:1 mixture of Et$_2$O and EtOAc (100 mL) and washed with saturated brine (3×25 mL). The organic layer was dried (MgSO$_4$), filtered and concentrated in vacuo. Purification by chromatography (SiO$_2$, 0-5% MeOH in DCM) gave a yellow gum (94 mg, 47%). LCMS (ES+) 427 (M+H)$^+$. The yellow gum (75 mg, 0.176 mmol) was dissolved in DCM (3 mL) and TFA (2 mL) and the solution obtained was stirred at r.t. for 2 h. The excess solvent was removed in vacuo and the residue azeotroped with toluene (3×10 mL). To the residue obtained were added 6-chloropurine (65 mg, 0.26 mmol), DIPEA (0.16 mL, 0.88 mmol) and n-butanol (2.5 mL) and the reaction mixture was heated under microwave irradiation at 120° C. for 1 h. After cooling, the mixture was dissolved in a 1:1 mixture of Et$_2$O and EtOAc (100 mL) and washed with saturated brine (3×25 mL). The organic layer was dried (MgSO$_4$), filtered and evaporated to dryness. Purification by preparative HPLC gave the title compound (29.6 mg, 38%) as a brown gum. $\delta_H$ (CDCl$_3$) 8.35 (1H, s), 8.06 (1H, s), 7.95 (1H, s), 7.51 (1H, d, J=8.18 Hz), 7.44 (1H, d, J=7.05 Hz), 6.47 (1H, br s), 5.85 (1H, br s), 5.46 (1H, d, J=8.00 Hz), 4.05 (1H, br s), 3.90 (1H, d, J=12.75 Hz), 3.65-3.43 (1H, m), 3.41-3.34 (1H, m), 2.97 (1H, d, J=8.22 Hz), 2.71 (3H, s), 2.13 (1H, d, J 11.43 Hz), 2.06 (1H, d, J=9.97 Hz), 2.01 (3H, s), 1.87-1.70 (2H, m), 1.66 (3H, d, J=6.72 Hz), 1H under CHCl$_3$. LCMS (ES+) 445 (M+H)$^+$, RT 2.33 minutes (Method 2).

Example 29

(S)—N-(2-{8-Chloro-3-[1-(9H-purin-6-ylamino) ethyl]quinolin-2-ylamino}ethyl)acetamide Intermediate 23 (150 mg, 0.44 mmol), N-acetylethylenediamine (100 mg, 1 mmol), NMP (3 mL) and DIPEA (0.5 mL) were combined in a sealed tube. The reaction mixture was heated to 100° C. for 60 h. After cooling to r.t. the reaction mixture was partitioned between EtOAc and water. The organic layer was washed with water (3×5 mL), dried (MgSO$_4$) and concentrated in vacuo. The residue was purified by column chromatography to give an off-white foam (95 mg, 53%). The foam (95 mg, 0.23 mmol) was combined with MeOH (3 mL) and 2N HCl in Et$_2$O (3 mL) and stirred at r.t. for 18 h. The reaction mixture was concentrated in vacuo and the residue was combined with 6-chloropurine (31 mg, 0.2 mmol), n-butanol (3 mL) and DIPEA (0.5 mL) in a sealed tube and heated to 120° C. for 20 h. The reaction mixture was concentrated in vacuo and purified by preparative HPLC to give the title compound (16 mg, 8%) as a yellow solid. $\delta_H$ (DMSO-d$_6$) 8.32 (1H, br s), 8.24-8.16 (2H, m), 8.02 (1H, t, J=5.48 Hz), 7.99 (1H, s), 7.64 (1H, dd, J 7.54, 1.36 Hz), 7.61

(1H, dd, J 7.99, 1.43 Hz), 7.37 (1H, t, J=5.20 Hz), 7.13 (1H, t, J=7.75 Hz), 5.65 (1H, br s), 3.78-3.68 (1H, m), 3.59-3.49 (1H, m), 3.48-3.36 (3H, m), 1.82 (3H, s), 1.63 (3H, d, J=6.70 Hz). LCMS (ES+) 425 (M+H)$^+$, RT 7.50 minutes (Method 8).

Example 30

(S)-1-(2-{8-Chloro-3-[1-(9H-purin-6-ylamino)ethyl]quinolin-2-ylamino}ethyl)-imidazolidin-2-one Similarly, Intermediate 23 (150 mg, 0.44 mmol) and 1-(2-aminoethyl)-imidazolidin-2-one (129 mg, 1 mmol) gave the title compound (16.4 mg, 8%) as a yellow solid. $\delta_H$ (DMSO-d$_6$) 8.26 (1H, d, J=7.81 Hz), 8.24-8.15 (2H, m), 7.96 (1H, s), 7.64 (1H, dd, J 7.54, 1.37 Hz), 7.59 (1H, dd, J 7.94, 1.38 Hz), 7.34 (1H, t, J=5.31 Hz), 7.12 (1H, t, J=7.75 Hz), 6.26 (1H, s), 5.65 (1H, s), 3.86-3.79 (1H, m), 3.63-3.53 (1H, m), 3.50 (2H, t, J 7.87 Hz), 3.42 (2H, t, J=6.43 Hz), 3.21-3.14 (3H, m), 1.61 (3H, d, J=6.73 Hz). LCMS (ES+) 452 (M+H)$^+$, RT 2.31 minutes (Method 2).

Example 31

(S)-8-Chloro-N-(3-methoxypropyl)-3-[1-(9H-purin-6-ylamino)ethyl]quinolin-2-amine Similarly, Intermediate 23 (150 mg, 0.44 mmol) and 3-methoxypropylamine (89 mg, 1 mmol) gave the title compound (15.4 mg, 8%) as a tan solid. $\delta_h$ (DMSO-d$_6$) 8.31-8.19 (2H, m), 8.19 (1H, s), 7.99 (1H, s), 7.65-7.61 (2H, m), 7.21 (1H, t, J=5.24 Hz), 7.12 (1H, t, J=7.74 Hz), 5.69 (1H, br s), 3.65-3.57 (2H, m), 3.18 (3H, s), 1.99-1.83 (2H, m), 1.65 (3H, d, J=6.72 Hz), 3H under H$_2$O. LCMS (ES+) 412 (M+H)$^+$, RT 7.68 minutes (Method 8).

Example 32

(S)-8-Chloro-N-(2-ethoxyethyl)-3-[1-(9H-purin-6-ylamino)ethyl]quinolin-2-amine

Similarly, Intermediate 23 (150 mg, 0.44 mmol) and 2-ethoxyethylamine (89 mg, 1 mmol) gave the title compound (13.1 mg, 7%) as a tan solid. $\delta_H$ (DMSO-d$_6$) 8.25 (1H, s), 8.22 (1H, d, J=8.91 Hz), 8.18 (1H, s), 8.01 (1H, s), 7.66-7.61 (2H, m), 7.27 (1H, br s), 7.14 (1H, t, J=7.74 Hz), 5.69 (1H, br s), 3.80-3.66 (2H, m), 3.67-3.61 (2H, m), 3.42 (2H, qd, J 6.98, 1.19 Hz), 1.65 (3H, d, J=6.71 Hz), 1.02 (3H, t, J=6.98 Hz), 1H under H$_2$O. LCMS (ES+) 412 (M+H)$^+$, RT 2.82 minutes (Method 1).

Example 33

(S)-2-{8-Chloro-3-[1-(9H-purin-6-ylamino)ethyl]quinolin-2-ylamino}ethanol

Similarly, Intermediate 23 (150 mg, 0.44 mmol) and 2-aminoethanol (61 mg, 1 mmol) gave the title compound (29.8 mg, 17%) as an off-white solid. $\delta_H$ (DMSO-d$_6$) 8.24 (2H, s), 8.18 (1H, br s), 8.00 (1H, s), 7.65-7.60 (2H, m), 7.37 (1H, br s), 7.13 (1H, t, J=7.75 Hz), 5.70 (1H, br s), 4.87 (1H, t, J=4.98 Hz), 3.77-3.68 (3H, m), 3.60-3.53 (1H, m), 1.64 (3H, d, J=6.73 Hz), 1H under H$_2$O. LCMS (ES+) 384 (M+H)$^+$, RT 6.91 minutes (Method 8).

Example 34

(S)-8-Chloro-N-methyl-3-[1-(pyrrolo[2,1-f][1,2,4]triazin-4-ylamino)ethyl]quinolin-2-amine A solution of Intermediate 38 (75 mg, 0.275 mmol), 4-bromopyrrolo[2,1-f][1,2,4]-triazine (55 mg, 0.275 mmol) and DIPEA (1.0 mL, 5.46 mmol) in n-butanol (4 mL) was heated at 140° C. under microwave irradiation for 1 h. The reaction mixture was concentrated in vacuo and purified by preparative HPLC to afford the title compound (39.2 mg, 40%) as a yellow solid. $\delta_H$ (DMSO-d$_6$) 8.63 (1H, d, J=7.61 Hz), 7.92 (1H, s), 7.89 (1H, s), 7.66 (1H, dd, J 2.65, 1.56 Hz), 7.63 (2H, d, J 7.74 Hz), 7.20-7.16 (1H, m), 7.13-7.06 (2H, m), 6.67 (1H, dd, J 4.37, 2.61 Hz), 5.64-5.58 (1H, m), 3.05 (3H, d, J=4.34 Hz), 1.60 (3H, d, J=6.75 Hz). LCMS (ES+) 353 (M+H)$^+$, 3.02 minutes (Method 2).

Example 35

(S)-8-Chloro-3-[1-(2-fluoro-9H-purin-6-ylamino)ethyl]-N-methylquinolin-2-amine

Similarly, Intermediate 38 (75 mg, 0.275 mmol), 6-chloro-2-fluoro-9H-purine (47 mg, 0.275 mmol) and DIPEA (1.0 mL, 5.46 mmol) in n-butanol (4 mL) afforded the title compound (8.4 mg, 8%) as a white solid. $\delta_H$ (DMSO-d$_6$) 8.92-8.75 (1H, m), 8.19 (1H, s), 7.92 (1H, s), 7.66-7.56 (2H, m), 7.12 (1H, t, J=7.77 Hz), 5.55-5.45 (1H, m), 3.08 (3H, d, J=4.31 Hz), 1.59 (3H, d, J=6.73 Hz), 2H missing. LCMS (ES+) 372 (M+H)$^+$, 2.43 minutes (Method 2).

Example 36

(S)—N$^2$-{1-[8-Chloro-2-(methylamino)quinolin-3-yl]ethyl}-6-methyl-[1,3,5]triazine-2,4-diamine Similarly, Intermediate 38 (75 mg, 0.275 mmol), 2-amino-4-chloro-6-methyl-[1,3,5]triazine (40 mg, 0.275 mmol) and DIPEA (1.0 mL, 5.46 mmol) in n-butanol (4 mL) afforded the title compound (45 mg, 48%) as a white solid. $\delta_H$ (DMSO-d$_6$) 7.92-7.73 (2H, m), 7.64 (2H, d, J 7.73 Hz), 7.20-7.09 (1H, m), 6.85-6.71 (2H, m), 5.38-5.16 (1H, m), 3.05 (3H, d, J=4.36 Hz), 2.16-2.12 (3H, m), 1.50 (3H, d, J=6.63 Hz), 1H under H$_2$O. LCMS (ES+) 344 (M+H)$^+$, 3.03 minutes (Method 1).

Example 37

(S)—N$^2$-{1-[8-Chloro-2-(methylamino)quinolin-3-yl]ethyl}-[1,3,5]triazine-2,4-diamine Similarly, Intermediate 38 (75 mg, 0.275 mmol), 2-amino-4-chloro-[1,3,5]triazine (35.7 mg, 0.275 mmol) and DIPEA (1.0 mL, 5.46 mmol) in n-butanol (4 mL) afforded the title compound (35.9 mg, 40%) as a white solid. $\delta_H$ (DMSO-d$_6$) 8.04-7.98 (1H, m), 7.91-7.68 (2H, m), 7.64 (2H, d, J=7.52 Hz), 7.13 (1H, t, J=7.78 Hz), 6.95-6.76 (2H, m), 5.35-5.13 (1H, m), 3.06 (3H, d, J=4.27 Hz), 2.11 (1H, s), 1.53-1.42 (3H, m). LCMS (ES+) 330 (M+H)$^+$, 9.16 minutes (Method 9).

Example 38

(S)-2-{8-Chloro-3-[1-(pyrrolo[2,1-f][1,2,4]triazin-4-ylamino)ethyl]quinolin-2-ylamino}ethanol A solution of Intermediate 39 (75 mg, 0.248 mmol), 4-bromopyrrolo[2,1-f][1,2,4]-triazine (49 mg, 0.248 mmol) and DIPEA (1.0 mL, 5.46 mmol) in n-butanol (5 mL) was stirred at r.t. for 3 days. The reaction mixture was concentrated in vacuo and purified by preparative HPLC to give the title compound (39.0 mg, 41%) as a white solid. $\delta_H$ (DMSO-$d_6$) 8.61 (1H, d, J=7.92 Hz), 8.00 (1H, s), 7.92 (1H, s), 7.70-7.63 (3H, m), 7.30-7.24 (1H, m), 7.15 (1H, t, J 7.75 Hz), 7.05 (1H, d, J=4.19 Hz), 6.68 (1H, dd, J 4.37, 2.61 Hz), 5.69 (1H, t, J=7.19 Hz), 4.85 (1H, t, J=4.97 Hz), 3.75-3.68 (3H, m), 3.60-3.53 (1H, m), 1.66 (3H, d, J=6.73 Hz). LCMS (ES+) 383 (M+H)$^+$, 3.22 minutes (Method 1).

Example 39

(S)-2-{8-Chloro-3-[1-(pyrazolo[1,5-a]pyrimidin-7-ylamino)ethyl]quinolin-2-ylamino}ethanol A solution of Intermediate 39 (75 mg, 0.248 mmol), 7-chloropyrazolo[1,5-c]pyrimidine (38 mg, 0.248 mmol) and DIPEA (1.0 mL, 5.46 mmol) in n-butanol (5 mL) was heated at 140° C. under microwave irradiation for 1 h. The reaction mixture was concentrated in vacuo and purified by preparative HPLC to afford the title compound (26.1 mg, 28%) as an off-white solid. $\delta_H$ (DMSO-$d_6$) 8.41 (1H, s), 8.21 (1H, d, J 2.29 Hz), 8.10 (1H, d, J=5.20 Hz), 8.03 (1H, s), 7.65 (1H, d, J=7.52 Hz), 7.58 (1H, d, J=7.89 Hz), 7.20 (1H, d, J=5.73 Hz), 7.12 (1H, t, J=7.73 Hz), 6.51 (1H, d, J=2.28 Hz), 5.87 (1H, d, J=5.27 Hz), 5.19 (1H, d, J=6.85 Hz), 3.82-3.62 (5H, m), 1.69 (3H, d, J=6.57 Hz). LCMS (ES+) 383 (M+H)$^+$, 13.2 minutes (Method 6).

Example 40

(S)-2-{8-Chloro-3-[1-(2-fluoro-9H-purin-6-ylamino)ethyl]quinolin-2-ylamino}ethanol Similarly, Intermediate 39 (75 mg, 0.248 mmol), 6-chloro-2-fluoro-9H-purine (42.8 mg, 0.248 mmol) and DIPEA (1.0 mL, 5.46 mmol) in n-butanol (5 mL) afforded the title compound (13.2 mg, 13%) as an off-white solid. $\delta_H$ (DMSO-$d_6$) 13.14 (1H, s), 8.20-8.15 (1H, m), 7.98 (1H, s), 7.63 (2H, dd, J 13.06, 7.57 Hz), 7.17-7.11 (2H, m), 7.02 (1H, s), 5.56-5.48 (1H, m), 4.85-4.80 (1H, m), 3.75-3.69 (3H, m), 3.65-3.58 (1H, m), 1.62 (3H, d, J=6.62 Hz). LCMS (ES+) 402 (M+H)$^+$, 7.22 minutes (Method 8).

Example 41

(S)-2-{3-[1-(4-Amino-[1,3,5]triazin-2-ylamino)ethyl]-8-chloroquinolin-2-ylamino}-ethanol Similarly, Intermediate 39 (75 mg, 0.248 mmol), 2-amino-4-chloro-[1,3,5]triazine (32 mg, 0.248 mmol) and DIPEA (1.0 mL, 5.46 mmol) in n-butanol (5 mL) afforded the title compound (42.4 mg, 48%) as an off-white solid. $\delta_H$ (DMSO-$d_6$) 8.07-7.82 (2H, m), 7.69-7.61 (2H, m), 7.23-7.10 (2H, m), 7.00-6.70 (2H, m), 5.34-5.20 (1H, m), 3.80-3.68 (3H, m), 3.61-3.54 (1H, m), 1.56-1.48 (3H, m), 2H under H$_2$O. LCMS (ES+) 360 (M+H)$^+$, 8.45 minutes (Method 6).

Example 42

(S)-2-{3-[1-(4-Amino-6-methyl-[1,3,5]triazin-2-ylamino)ethyl]-8-chloroquinolin-2-ylamino}ethanol Similarly, Intermediate 39 (75 mg, 0.248 mmol), 2-amino-4-chloro-6-methyl-[1,3,5]triazine (36 mg, 0.248 mmol) and DIPEA (1.0 mL, 5.46 mmol) in n-butanol (5 mL) afforded the title compound (45.6 mg, 49%) as an off-white solid. $\delta_H$ (DMSO-$d_6$) 7.93 (1H, s), 7.79 (1H, d, J=8.23 Hz), 7.68-7.63 (2H, m), 7.36-7.26 (1H, m), 7.18-7.12 (1H, m), 7.00-6.40 (2H, m), 6.80 (1H, s), 5.41-5.19 (1H, m), 3.80-3.65 (3H, m), 3.60-3.51 (1H, m), 2.23-2.07 (3H, m), 1.53 (3H, d, J=6.70 Hz). LCMS (ES+) 374 (M+H)$^+$, 2.65 minutes (Method 1).

Example 43

(S)-2-{8-Chloro-3-[1-(5-methyl-[1,2,4]triazolo[1,5-a]pyrimidin-7-ylamino)ethyl]-quinolin-2-ylamino}ethanol Similarly, Intermediate 39 (75 mg, 0.248 mmol), 7-chloro-5-methyl-[1,2,4]triazolo[1,5-a]pyrimidine (42 mg, 0.248 mmol) and DIPEA (1.0 mL, 5.46 mmol) in n-butanol (5 mL) afforded the title compound (61.4 mg, 62%) as a tan solid. $\delta_H$ (DMSO-$d_6$) 8.85-8.63 (1H, m), 8.50 (1H, s), 8.05 (1H, s), 7.66 (1H, dd, J 7.54, 1.36 Hz), 7.60 (1H, dd, J 7.98, 1.39 Hz), 7.17-7.09 (2H, m), 6.06 (1H, s), 5.23-5.17 (1H, m), 4.90-4.80 (1H, m), 3.78-3.67 (4H, m), 2.38 (3H, s), 1.68 (3H, d, J=6.54 Hz). LCMS (ES+) 398 (M+H)$^+$, 7.12 minutes (Method 8).

Example 44

(S)-2-{3-[1-(2-Amino-9H-purin-6-ylamino)ethyl]-8-chloroquinolin-2-ylamino}ethanol Similarly, Intermediate 39 (75 mg, 0.248 mmol), 6-chloro-9H-purin-2-amine (42 mg, 0.248 mmol) and DIPEA (1.0 mL, 5.46 mmol) in n-butanol (5 mL) afforded the title compound (11.9 mg, 12%) as a tan solid. $\delta_H$ (DMSO-$d_6$) 8.14 (1H, s), 7.93 (1H, s), 7.60-7.48 (4H, m), 7.02 (1H, t, J=7.75 Hz), 5.83 (2H, s), 5.55-5.40 (1H, m), 5.05-4.83 (1H, m), 3.72-3.54 (3H, m), 3.42-3.32 (1H, m), 1.54 (3H, d, J=6.72 Hz). LCMS (ES+) 399 (M+H)$^+$, 6.67 minutes (Method 8).

Example 45

(S)-2-Methyl-1-{3-[1-(9H-purin-6-ylamino)ethyl]-8-chloroquinolin-2-ylamino}propan-2-ol Similarly, Intermediate 40 (50 mg, 0.17 mmol), 6-bromopurine (50 mg, 0.25 mmol) and DIPEA (1.0 mL, 5.46 mmol) in n-butanol (6 mL) afforded the title compound (13.9 mg, 20%) as a yellow glass. $\delta_H$ (DMSO-$d_6$) 8.25 (1H, br s), 8.17 (1H, br s), 8.04 (1H, s), 7.64 (2H, d, J=7.71 Hz), 7.28 (1H, br s), 7.15 (1H, t, J=7.78 Hz), 5.17 (1H, s), 3.72-3.64 (1H, m), 3.53-3.45 (1H, m), 3.20 (1H, s), 1.67 (3H, d, J=6.67 Hz), 1.14 (6H, s), 2H under H$_2$O. LCMS (ES+) 412 (M+H)$^+$, 7.39 minutes (Method 8).

Example 46

(S)-1-{8-Chloro-3-[1-(pyrrolo[2,1-f][1,2,4]triazin-4-ylamino)ethyl]quinolin-2-ylamino}-2-methylpropan-2-ol Similarly, Intermediate 40 (50 mg, 0.17 mmol), 4-bromopyrrolo[2,1-j][1,2,4]-triazine (100 mg, 0.51 mmol) and DIPEA (1.0 mL, 5.46 mmol) in n-butanol (6 mL) afforded the title compound (9.2 mg, 13%) as a clear glass. $\delta_H$ (DMSO-$d_6$) 8.62 (1H, d, J=8.10 Hz), 8.06 (1H, s), 7.93 (1H, s), 7.73-7.63 (3H, m), 7.20-7.12 (2H, m), 7.03-7.00 (1H, m), 6.68-6.65 (1H, m), 5.77-5.70 (1H, m), 5.08 (1H, s), 3.68 (1H, dd, J 13.43, 5.71 Hz), 3.48 (1H, dd, J 13.42, 5.28 Hz), 1.70 (3H, d, J=6.69 Hz), 1.15 (3H, s), 1.14 (3H, s). LCMS (ES+) 411 (M+H)⁺, 7.99 minutes (Method 8).

Example 47

(S)-1-{3-[1-(4-Amino-6-methyl-[1,3,5]triazin-2-ylamino)ethyl]-8-chloroquinolin-2-ylamino}-2-methylpropan-2-ol Similarly, Intermediate 40 (50 mg, 0.17 mmol), 2-amino-4-chloro-6-methyl-[1,3,5]triazine (50 mg, 0.35 mmol) and DIPEA (1.0 mL, 5.46 mmol) in n-butanol (6 mL) afforded the title compound (26.8 mg, 39%) as a clear glass. $\delta_H$ (DMSO-$d_6$) 7.96 (1H, s), 7.83-7.52 (3H, m), 7.34-7.05 (1H, m), 7.00-6.50 (3H, m), 5.47-5.15 (2H, m), 3.75-3.21 (2H, m), 2.20-2.09 (3H, m), 1.56 (3H, d, J=6.72 Hz), 1.20-1.11 (6H, m). LCMS (ES+) 402 (M+H)⁺, 6.91 minutes (Method 8).

Example 48

(S)-1-(8-Chloro-3-{1-[4-(methylamino)-[1,3,5]triazin-2-ylamino]ethyl}quinolin-2-ylamino)-2-methylpropan-2-ol Similarly, Intermediate 40 (50 mg, 0.17 mmol), 4-chloro-2-(methylamino)-[1,3,5]triazine (50 mg, 0.28 mmol) and DIPEA (1.0 mL, 5.46 mmol) in n-butanol (6 mL) afforded the title compound (20.1 mg, 30%) as an off-white solid. $\delta_H$ (DMSO-$d_6$) 8.20-7.80 (2H, m) 7.68-7.59 (2H, m), 7.30 (1H, br s), 7.20-7.00 (2.5H, m), 6.91 (0.5H, br s), 5.45-5.10 (2H, m), 3.70-3.40 (2H, m), 2.80-2.65 (3H, m), 1.55 (3H, d, J=6.79 Hz), 1.27-1.09 (6H, m). LCMS (ES+) 402 (M+H)⁺, 7.07 minutes (Method 8).

Example 49

(S)-1-{3-[1-(4-Amino-[1,3,5]triazin-2-ylamino)ethyl]-8-chloroquinolin-2-ylamino}-2-methylpropan-2-ol Similarly, Intermediate 40 (50 mg, 0.17 mmol), 2-amino-4-chloro-[1,3,5]triazine (50 mg, 0.30 mmol) and DIPEA (1.0 mL, 5.46 mmol) in n-butanol (6 mL) afforded the title compound (14.8 mg, 22%) as an off-white solid. $\delta_H$ (DMSO-$d_6$) 8.12-7.81 (2H, m), 7.71-7.62 (2H, m), 7.33-6.85 (3H, m), 5.44-5.11 (2H, m), 3.72-3.63 (1H, m), 3.65-3.41 (1H, m), 1.57 (3H, s), 1.16 (6H, d, J=6.30 Hz), 2H under H₂O. LCMS (ES+) 388 (M+H)⁺, 8.80 minutes (Method 9).

Example 50

(S)-1-{8-Chloro-3-[1-(pyrido[3,2-d]pyrimidin-4-ylamino)ethyl]quinolin-2-ylamino}-2-methylpropan-2-ol Similarly, Intermediate 40 (50 mg, 0.17 mmol), 4-chloropyrido[3,2-d]pyrimidine (50 mg, 0.30 mmol) and DIPEA (1.0 mL, 5.46 mmol) in n-butanol (6 mL) afforded the title compound (24.5 mg, 34%) as a brown solid. $\delta_H$ (DMSO-$d_6$) 9.02 (1H, d, J=8.34 Hz), 8.88 (1H, dd, J 4.25, 1.57 Hz), 8.55 (1H, s), 8.17 (1H, dd, J 8.45, 1.58 Hz), 8.11 (1H, s), 7.89 (1H, dd, J 8.47, 4.24 Hz), 7.66 (2H, d, J=7.75 Hz), 7.22-7.11 (2H, m), 5.80-5.71 (1H, m), 5.11 (1H, s), 3.67 (1H, dd, J 13.42, 5.72 Hz), 3.55-3.47 (1H, m), 1.76 (3H, d, J=6.75 Hz), 1.13 (6H, d, J=11.92 Hz). LCMS (ES+) 423 (M+H)⁺, 9.72 minutes (Method 9).

Example 51

(S)-1-{3-[1-(2-Amino-9H-purin-6-ylamino)ethyl]-8-chloroquinolin-2-ylamino}-2-methylpropan-2-ol Similarly, Intermediate 40 (50 mg, 0.17 mmol), 6-chloro-9H-purin-2-amine (50 mg, 0.29 mmol) and DIPEA (1.0 mL, 5.46 mmol) in n-butanol (6 mL) at 150° C. afforded the title compound (10.1 mg, 14%) as a white solid. $\delta_H$ (DMSO-$d_6$) 8.44 (1H, s), 8.07 (1H, s), 8.00-7.88 (1H, m), 7.76-7.57 (4H, m), 7.15 (1H, t, J=7.75 Hz), 6.02-5.92 (2H, m), 5.70-5.58 (1H, m), 5.46-5.37 (1H, m), 3.79-3.69 (1H, m), 1.69 (3H, d, J=6.68 Hz), 1.16 (3H, s), 1.08 (3H, s), 1H under H₂O. LCMS (ES+) 427 (M+H)⁺, 6.86 minutes (Method 8).

Example 52

(S)-1-{8-Chloro-3-[1-(thieno[2,3-d]pyrimidin-4-ylamino)ethyl]quinolin-2-ylamino}-2-methylpropan-2-ol Similarly, Intermediate 40 (50 mg, 0.17 mmol), 4-chlorothieno[2,3-d]pyrimidine (50 mg, 0.29 mmol) and DIPEA (1.0 mL, 5.46 mmol) in n-butanol (6 mL) afforded the title compound (6 mg, 8%) as a brown solid. $\delta_H$ (DMSO-$d_6$) 8.41-8.33 (2H, m), 8.05 (1H, s), 7.77 (1H, d, J=5.96 Hz), 7.72-7.62 (3H, m), 7.19-7.13 (1H, m), 7.11-7.06 (1H, m), 5.75-5.70 m), 5.12 (1H, s), 3.69 (1H, dd, J 13.33, 5.50 Hz), 3.48 (1H, dd, J 13.35, 5.17 Hz), 1.69 (3H, d, J=6.58 Hz), 1.15 (3H, s), 1.12 (3H, s). LCMS (ES+) 428 (M+H)⁺, 1.84 minutes (Method 2).

Example 53

(S)-1-{8-Chloro-3-[1-(pyrazolo[1,5-a]pyrimidin-7-ylamino)ethyl]quinolin-2-ylamino}-2-methylpropan-2-ol Similarly, Intermediate 40 (50 mg, 0.17 mmol), 7-chloropyrazolo[1,5-a]-pyrimidine (100 mg, 0.51 mmol) and DIPEA (1.0 mL, 5.46 mmol) in n-butanol (6 mL) afforded the title compound (15.1 mg, 22%) as a tan glass. $\delta_H$ (DMSO-$d_6$) 8.20 (1H, d, J=2.28 Hz), 8.11 (1H, d, J=5.21 Hz), 8.06 (1H, s), 7.66 (1H, dd, J 7.55, 1.35 Hz), 7.60 (1H, dd, J 7.99, 1.38 Hz), 7.16-7.09 (2H, m), 6.51 (1H, d, J=2.28 Hz), 5.91 (1H, d, J=5.27 Hz), 5.27-5.19 (2H, m), 3.77 (1H, dd, J 13.45, 5.77 Hz), 3.57 (1H, dd, J 13.46, 5.60 Hz), 1.73 (3H, d, J=6.59 Hz), 1.21 (3H, s), 1.19 (3H, s), 1H under H₂O. LCMS (ES+) 411 (M+H)⁺, 2.99 minutes (Method 1).

Example 54

(S)-1-({3-[1-(4-Amino-[1,3,5]triazin-2-ylamino)ethyl]-8-chloroquinolin-2-ylamino}methyl)cyclopropanol Similarly, Intermediate 41 (50 mg, 0.15 mmol), 2-amino-4-chloro-[1,3,5]triazine (50 mg, 0.38 mmol) and DIPEA (1.0 mL, 5.46 mmol) in n-butanol (1 mL) afforded the title compound (6.0 mg, 10%) as a clear glass. $\delta_H$ (DMSO-$d_6$) 8.15-7.70 m), 7.67 (3H, t, J=8.97 Hz), 7.28 (1H, t, J=5.23 Hz), 7.16 (1H, t, J=7.70 Hz), 7.10-6.70 (2H, m), 5.95 (0.5H, br s), 5.75 (0.5H, br s), 5.40-5.20 (1H, m), 3.75-3.50 (2H, m), 1.56 (3H, br s), 0.63 (4H, br s). LCMS (ES+) 386 (M+H)⁺, 8.80 minutes (Method 9).

Example 55

(S)-1-[(8-Chloro-3-{1-[4-(methylamino)-[1,3,5]triazin-2-ylamino]ethyl}quinolin-2-ylamino)methyl]cyclopropanol Similarly, Intermediate 41 (50 mg, 0.15 mmol), 4-chloro-2-(methylamino)-[1,3,5]triazine (50 mg, 0.35 mmol) and DIPEA (1.0 mL, 5.46 mmol) in n-butanol (1 mL) afforded the title compound (10.3 mg, 17%) as a clear glass. $\delta_H$ (DMSO-$d_6$) 8.14-7.84 (3H, m), 7.70-7.62 (3H, m), 7.34-6.97 (2H, m), 5.95-5.65 (1H, m), 5.40-5.20 (1H, m), 3.83-3.48 (3H, m), 3.20 (1H, s), 2.80-2.70 (4H, m), 1.56-1.52 (4H, m). LCMS (ES+) 400 (M+H)$^+$, 7.11 minutes (Method 8).

Example 56

(S)-1-({3-[1-(4-Amino-6-methyl-[1,3,5]triazin-2-ylamino)ethyl]-8-chloroquinolin-2-ylamino}methyl)cyclopropanol Similarly, Intermediate 41 (50 mg, 0.15 mmol), 2-amino-4-chloro-6-methyl-[1,3,5]triazine (50 mg, 0.35 mmol) and DIPEA (1.0 mL, 5.46 mmol) in n-butanol (1 mL) afforded the title compound (14.1 mg, 24%) as an off-white solid. $\delta_H$ (DMSO-$d_6$) 7.84 (1H, s), 7.67 (1H, d, J=8.29 Hz), 7.58-7.51 (2H, m), 7.26 (1H, s), 7.08-7.02 (1H, m), 6.60-6.64 (1H, m), 5.30-5.08 (1H, m), 3.70-3.12 (8H, m), 2.10-1.98 (3H, m), 1.44 (3H, d, J=6.55 Hz). LCMS (ES+) 400 (M+H)$^+$, 8.92 minutes (Method 9).

Example 57

(S)-1-({8-Chloro-3-[1-(9H-purin-6-ylamino)ethyl]quinolin-2-ylamino}methyl)-cyclopropanol Similarly, Intermediate 41 (50 mg, 0.15 mmol), 6-chloropurine (50 mg, 0.32 mmol) and DIPEA (1.0 mL, 5.46 mmol) in n-butanol (6 mL) afforded the title compound (6.0 mg, 10%) as an off-white solid. $\delta_H$ (DMSO-$d_6$) 8.26 (1H, s), 8.18 (1H, s), 8.04 (1H, s), 7.64 (2H, d, J=7.72 Hz), 7.50-7.42 (1H, m), 7.19-7.11 (1H, m), 5.80-5.70 (2H, m), 3.82 (1H, dd, J 13.97, 5.57 Hz), 3.57 (1H, dd, J 14.05, 4.71 Hz), 1.68 (3H, d, J=6.75 Hz), 0.71-0.54 (4H, m), 2H under H$_2$O. LCMS (ES+) 410 (M+H)$^+$, 7.21 minutes (Method 8).

Example 58

(S)-1-(3-{8-Chloro-3-[1-(9H-purin-6-ylamino)ethyl]quinolin-2-ylamino}propyl)-pyrrolidin-2-one A solution of Intermediate 42 (169 mg, 0.44 mmol), 6-chloropurine (61 mg, 0.40 mmol) and DIPEA (1.0 mL, 5.46 mmol) in n-butanol (3 mL) was heated at 120° C. for 20 h. The reaction mixture was concentrated in vacuo and the residue was purified by preparative HPLC to afford the title compound (26.6 mg, 14%) as a brown solid. $\delta_H$ (DMSO-$d_6$) 8.31-8.14 (3H, m), 7.97 (1H, s), 7.65-7.56 (2H, m), 7.32-7.25 (1H, m), 7.11 (1H, t, J 7.72 Hz), 5.75-5.60 (1H, m), 3.70-3.46 (3H, m), 2.25 (2H, t, J=8.01 Hz), 2.00-1.83 (4H, m), 1.64 (3H, d, J=6.69 Hz), 3H under H$_2$O. LCMS (ES+) 465 (M+H)$^+$, 2.20 minutes (Method 1).

Example 59

(S)-5-({8-Chloro-3-[(S)-1-(pyrrolo[2,1-f][1,2,4]triazin-4-ylamino)ethyl]quinolin-2-ylamino}methyl)pyrrolidin-2-one Following the procedure described for Example 39, Intermediate 43 (50 mg, 0.16 mmol), 4-bromopyrrolo[2,1-f][1,2,4]triazine (40 mg, 0.28 mmol) and DIPEA (1.0 mL, 5.46 mmol) in n-butanol (6 mL) at 160° C. afforded the title compound (16.9 mg, 24%) as an off-white solid. $\delta_H$ (DMSO-$d_6$) 8.65 (1H, d, J 7.86 Hz), 8.02 (1H, s), 7.95 (1H, s), 7.77 (1H, s), 7.70-7.65 (3H, m), 7.32-7.26 (1H, m), 7.16 (1H, t, J=7.76 Hz), 7.08-7.05 (1H, m), 6.69 (1H, dd, J 4.37, 2.61 Hz), 5.74-5.66 (1H, m), 4.00-3.91 (1H, m), 3.86-3.77 (1H, m), 3.56-3.47 (1H, m), 2.25-2.01 (3H, m), 1.91-1.79 (1H, m), 1.66 (3H, d, J=6.72 Hz). LCMS (ES+) 436 (M+H)$^+$, 3.03 minutes (Method 1).

Example 60

(S)-5-({8-Chloro-3-[(S)-1-(pyrido[3,2-d]pyrimidin-4-ylamino)ethyl]quinolin-2-ylamino}methyl)pyrrolidin-2-one Similarly, Intermediate 43 (50 mg, 0.16 mmol), 4-chloropyrido[3,2-d]pyrimidine (40 mg, 0.27 mmol) and DIPEA (1.0 mL, 5.46 mmol) in n-butanol (6 mL) at 160° C. afforded the title compound (26.4 mg, 37%) as a brown solid. $\delta_H$ (DMSO-$d_6$) 9.06 (1H, d, J=8.09 Hz), 8.91 (1H, dd, J 4.26, 1.58 Hz), 8.56 (1H, s), 8.17 (1H, dd, J 8.45, 1.58 Hz), 8.09 (1H, s), 7.90 (1H, dd, J 8.48, 4.25 Hz), 7.77 (1H, s), 7.67-7.61 (2H, m), 7.33 (1H, t, J=5.52 Hz), 7.14 (1H, t, J=7.76 Hz), 5.75-5.69 (1H, m), 4.01-3.95 (1H, m), 3.81-3.74 (1H, m), 3.61-3.53 (1H, m), 2.25-2.02 (3H, m), 1.90-1.83 (1H, m), 1.72 (3H, d, J=6.76 Hz). LCMS (ES+) 448 (M+H)$^+$, 2.87 minutes (Method 1).

Example 61

(S)-5-({8-Chloro-3-[(S)-1-(9H-purin-6-ylamino)ethyl]quinolin-2-ylamino}methyl)-pyrrolidin-2-one Similarly, Intermediate 43 (250 mg, 0.78 mmol), 6-chloropurine (121 mg, 0.87 mmol) and DIPEA (1.0 mL, 5.46 mmol) in n-butanol (6 mL) at 150° C. afforded the title compound (56.2 mg, 17%) as a pale yellow solid. $\delta_H$ (DMSO-$d_6$) 13.02 (1H, s), 8.29-8.15 (2H, m), 8.02 (1H, s), 7.77-7.68 (1H, m), 7.66-7.60 (2H, m), 7.43-7.35 (1H, m), 7.39 (1H, s), 7.14 (1H, t, J=7.75 Hz), 5.82-5.62 (1H, m), 4.03-3.93 (1H, m), 3.98 (1H, s), 3.78-3.54 (2H, m), 2.26-2.02 (2H, m), 1.90-1.81 (1H, m), 1.64 (3H, d, J=6.67 Hz). LCMS (ES+) 437 (M+H)$^+$, 7.98 minutes (Method 8).

Example 62

(S)-5-({3-[(S)-1-(4-Amino-6-methyl-[1,3,5]triazin-2-ylamino)ethyl]-8-chloroquinolin-2-ylamino}methyl)pyrrolidin-2-one Similarly, Intermediate 43 (50 mg, 0.16 mmol), 2-amino-4-chloro-6-methyl-[1,3,5]triazine (40 mg, 0.28 mmol) and DIPEA (1.0 mL, 5.46 mmol) in n-butanol (6 mL) at 140° C. afforded the title compound (9.2 mg, 13%) as a pale yellow solid. $\delta_H$ (DMSO-$d_6$) 7.93 (1H, s), 7.73-7.61 (3H, m), 7.19-7.12 (1H, m), 6.90-6.66 (2H, m), 5.34-5.20 (1H, m), 4.00-3.88 (1H, m), 3.78-3.70 (1H, m), 3.61-3.53 (1H, m), 2.27-

2.01 (6H, m), 1.90-1.80 (1H, m), 1.52 (3H, d, J=6.71 Hz), 1H under H$_2$O. LCMS (ES+) 427 (M+H)$^+$, 2.24 minutes (Method 2).

Example 63

(S)-5-({3-[(S)-1-(2-Amino-9H-purin-6-ylamino)ethyl]-8-chloroquinolin-2-ylamino}-methyl)pyrrolidin-2-one Similarly, Intermediate 43 (50 mg, 0.16 mmol), 6-chloro-9H-purin-2-amine (40 mg, 0.28 mmol) and DIPEA (1.0 mL, 5.46 mmol) in n-butanol (6 mL) at 160° C. afforded the title compound (6.9 mg, 10%) as an off-white solid. δ$_H$ (DMSO-d$_6$) 8.03 (1H, s), 7.75-7.62 (5H, m), 7.44-7.39 (1H, m), 7.19-7.13 (1H, m), 5.94-5.45 (2H, m), 3.98-3.92 (1H, m), 3.66-3.58 (3H, m), 2.19-1.91 (3H, m), 1.75-1.58 (4H, m), 1H under H$_2$O. LCMS (ES+) 452 (M+H)$^+$, 7.32 minutes (Method 8).

Example 64

1-[(S)-3-({8-Chloro-3-[(S)-1-(9H-purin-6-ylamino)ethyl]quinolin-2-ylamino}methyl)-pyrrolidin-1-yl]ethanone Similarly, Intermediate 44 (50 mg, 0.44 mmol), 6-chloropurine (50 mg, 0.32 mmol) and DIPEA (1.0 mL, 5.46 mmol) in n-butanol (6 mL) at 160° C. afforded the title compound (7.2 mg, 11%) as an off-white solid. δ$_H$ (DMSO-d$_6$) 13.1-12.6 (1H, br s), 8.27-8.12 (3H, m), 7.97 (1H, d, J 7.19 Hz), 7.63-7.56 (2H, m), 7.40-7.29 (1H, m), 7.13-7.07 (1H, m), 5.78-5.55 (1H, m), 3.65-3.29 (4H, m), 3.22-3.07 (2H, m), 2.76-2.60 (1H, m), 1.98-1.75 (4H, m), 1.74-1.56 (4H, m). LCMS (ES+) 465 (M+H)$^+$, 2.48 minutes (Method 2).

Example 65

(S)-5-({3-[(S)-1-(2-Aminopyrimidin-4-ylamino)ethyl]-8-chloroquinolin-2-ylamino}methyl)pyrrolidin-2-one A solution of Intermediate 43 (50 mg, 0.157 mmol), 2-amino-4-chloropyrimidine (40.7 mg, 0.314 mmol) and DIPEA (0.109 mL, 0.628 mmol) in n-butanol (1.5 mL) was heated under microwave irradiation at 170° C. for 2.5 h. After cooling, the mixture was dissolved in EtOAc (75 mL) and washed with saturated brine (3×15 mL). The organic layer was separated, dried (MgSO$_4$), filtered and concentrated in vacuo. Purification by preparative HPLC gave the title compound (3.7 mg, 6%) as a white solid. δ$_H$ (MeOD-d$_4$) 8.55 (2H, br s), 7.95 (1H, s), 7.70-7.60 (3H, m), 7.18 (1H, t, J=7.78 Hz), 6.05 (1H, d, J=6.58 Hz), 5.47 (1H, d, J=7.79 Hz), 5.00-4.80 (3H, m, masked by H$_2$O), 4.22-4.15 (1H, m), 3.89 (1H, dd, J 13.83, 4.67 Hz), 3.78 (1H, dd, J 13.83, 4.98 Hz), 2.40-2.20 (3H, m), 2.05-1.95 (1H, m), 1.68 (3H, d, J=6.49 Hz). LCMS (ES+) 412 (M+H)$^+$, 2.69 minutes (Method 1).

Examples 66 & 67

4-Amino-2-[(S)-1-(8-chloro-2-{[(S)-5-oxopyrrolidin-2-yl]methylamino}quinolin-3-yl)ethylamino]pyrimidine-5-carbonitrile and 2-Amino-4-[(S)-1-(8-chloro-2-{[(S)-5-oxopyrrolidin-2-yl]methylamino}quinolin-3-yl)ethylamino]pyrimidine-5-carbonitrile A solution of Intermediate 43 (100 mg, 0.314 mmol), 2,4-dichloro-5-cyano-pyrimidine (81.9 mg, 0.471 mmol) and DIPEA (0.164 mL, 0.941 mmol) in n-butanol (2 mL) was stirred at r.t. for 72 h. The mixture was dissolved in EtOAc (150 mL) and washed with saturated brine (3×30 mL). The organic layer was dried (MgSO$_4$), filtered and concentrated in vacuo. Purification by column chromatography (SiO$_2$, 97:2:1 DCM/MeOH/NH$_3$ solution in MeOH) gave an off-white glass (60 mg, 42%). LCMS (ES+) 456 (M+H)$^+$ (mixture of regioisomers). The off-white glass (60 mg, 0.132 mmol), 7M NH$_3$ in MeOH (1.5 mL) and NH$_4$OH (1 mL) were combined and heated under microwave irradiation at 120° C. for 1 h. After addition of saturated brine (20 mL) the reaction mixture was extracted with EtOAc (3×60 mL). The combined organic layers were dried (MgSO$_4$), filtered and concentrated in vacuo. Purification by preparative HPLC gave the title compounds (9.7 mg, 17%; and 22.2 mg, 39%) as white solids. δ$_H$ (DMSO-d$_6$) 8.23 (1H, s), 8.01 (1H, s), 7.86 (1H, d, J=8.07 Hz), 7.73-7.64 (3H, m), 7.30-7.20 (1H, br s), 7.18 (2H, t, J=7.76 Hz), 6.88 (1H, t, J=5.30 Hz), 5.55-5.47 (1H, m), 3.98-3.92 (1H, m), 3.73-3.57 (2H, m), 2.22-1.96 (3H, m), 1.83-1.72 (1H, m), 1.63 (3H, d, J=6.74 Hz). δ$_H$ (DMSO-d$_6$; T=125° C.) 8.23 (1H, s), 8.00 (1H, s), 7.65 (1H, s), 7.63 (1H, s), 7.45 (1H, d, J=8.00 Hz), 7.17 (1H, t, J=8.00 Hz), 7.09 (1H, br s), 6.70-6.57 (3H, m), 5.40-5.30 (1H, m), 4.02-3.95 (1H, m), 3.80-3.68 (2H, m), 2.25-2.10 (3H, m), 1.96-1.87 (1H, m), 1.63 (3H, d, J=8.00 Hz). LCMS (ES+) 412 (M+H)$^+$, 3.11 minutes (Method 1). LCMS (ES+) 412 (M+H)$^+$, 1.70 minutes (Method 2).

Example 68

(S)—N$^6$-[1-(2-Amino-8-chloroquinolin-3-yl)ethyl]-9H-purine-2,6-diamine

Following the procedure described for Example 39, Intermediate 45 (55 mg, 0.25 mmol), 6-chloro-9H-purin-2-amine (44 mg, 0.26 mmol) and DIPEA (0.5 mL, 2.23 mmol) in n-butanol (4 mL) at 140° C. afforded the title compound (30.1 mg, 34%) as an off-white solid. δ$_H$ (DMSO-d$_6$) 8.05 (1H, s), 7.72 (1H, s), 7.68-7.60 (3H, m), 7.14 (1H, t, J 7.74 Hz), 6.80 (2H, s), 5.78 (2H, s), 5.60-5.45 (1H, m), 1.63 (3H, d, J=6.75 Hz), 1H under H$_2$O. LCMS (ES+) 355 (M+H)$^+$, 6.37 minutes (Method 8).

Example 69

(S)—N$^2$-[1-(2-Amino-8-chloroquinolin-3-yl)ethyl]-[1,3,5]triazine-2,4-diamine

Similarly, Intermediate 45 (55 mg, 0.25 mmol), 2-amino-4-chloro-[1,3,5]triazine (35 mg, 0.26 mmol) and DIPEA (0.5 mL, 2.23 mmol) in n-butanol (4 mL) at 140° C. afforded the title compound (5.2 mg, 6%) as a white solid. δ$_H$ (DMSO-d$_6$) 8.59 (1H, s), 8.00 (1H, br s), 7.92 (1H, s), 7.80 (0.5H, m), 7.70 (0.5H, m), 7.64 (1H, t, J=6.66 Hz), 7.14 (1H, s), 7.00-6.60 (4H, m), 5.30-5.10 (1H, m), 1.50 (3H, s). LCMS (ES+) 316 (M+H)$^+$, 8.28 minutes (Method 9).

Example 70

(S)—N-[1-(2-Amino-8-chloroquinolin-3-yl)ethyl]pyrido[3,2-d]pyrimidin-4-amine

Similarly, Intermediate 45 (55 mg, 0.25 mmol), 4-chloropyrido[3,2-d]pyrimidine (44 mg, 0.26 mmol) and DIPEA (0.5 mL, 2.23 mmol) in n-butanol (4 mL) at 140° C. afforded the title compound (6.4 mg, 7%) as an off-white solid. δ$_H$ (DMSO-d$_6$) 9.03 (1H, d, J=7.98 Hz), 8.92-8.89 (1H, m), 8.51

(1H, s), 8.20-8.14 (1H, m), 8.06 (1H, s), 7.90 (1H, dd, J 8.46, 4.25 Hz), 7.65-7.58 (2H, m), 7.11 (1H, t, J=7.74 Hz), 6.85 (2H, s), 5.69-5.62 (1H, m), 1.71 (3H, d, J=6.80 Hz). LCMS (ES+) 351 (M+H)$^+$, 6.71 minutes (Method 8).

Example 71

(S)-8-Chloro-3-[1-(pyrrolo[2,1-f][1,2,4]triazin-4-ylamino)ethyl]quinolin-2-amine Following the procedure described for Example 38, Intermediate 45 (70 mg, 0.26 mmol), 4-bromopyrrolo[2,1-f][1,2,4]triazine (52 mg, 0.26 mmol) and DIPEA (1.0 mL, 5.46 mmol) in n-butanol (5 mL) at r.t. for 20 h afforded the title compound (2.6 mg) as an off-white solid. $\delta_H$ (DMSO-d$_6$) 8.62-8.57 (1H, m), 8.00 (1H, s), 7.89 (1H, s), 7.69-7.63 (3H, m), 7.17-7.11 (1H, m), 7.08 (1H, d, J=4.27 Hz), 6.79 (2H, br s), 6.69 (1H, dd, J 4.35, 2.60 Hz), 5.67-5.61 (1H, m), 1.64 (3H, d, J=6.76 Hz). LCMS (ES+) 339 (M+H)$^+$, 3.19 minutes (Method 1).

Example 72

(S)-2-(N'-{8-Chloro-3-[1-(9H-purin-6-ylamino)ethyl]quinolin-2-yl}-N'-methylamino)-N-methylacetamide Following the procedure described for Example 39, Intermediate 46 (65 mg, 0.21 mmol), 6-chloropurine (50 mg, 0.32 mmol) and DIPEA (1.0 mL, 4.56 mmol) in n-butanol (6 mL) at 150° C. afforded the title compound (10.7 mg, 12%) as a clear glass. $\delta_H$ (DMSO-d$_6$) 13.04-12.76 (1H, br s), 8.29 (2H, d, J=17.68 Hz), 8.11 (2H, d, J=9.46 Hz), 8.05 (1H, d, J=5.25 Hz), 7.70-7.63 (2H, m), 7.24 (1H, t, J=7.78 Hz), 5.72-5.54 (1H, m), 4.42 (1H, d, J=16.19 Hz), 3.86 (1H, d, J=16.18 Hz), 3.13 (3H, s), 2.62 (3H, d, J=4.61 Hz), 1.56 (3H, d, J=6.70 Hz). LCMS (ES+) 425 (M+H)$^+$, 2.31 minutes (Method 2).

Example 73

(S)-2-(N'-{3-[1-(4-Amino-6-methyl-[1,3,5]triazin-2-ylamino)ethyl]-8-chloroquinolin-2-yl}-N'-methylamino)-N-methylacetamide Similarly, Intermediate 46 (65 mg, 0.21 mmol), 2-amino-4-chloro-6-methyl-[1,3,5]triazine (50 mg, 0.35 mmol) and DIPEA (1.0 mL, 4.56 mmol) in n-butanol (6 mL) at 150° C. afforded the title compound (44.9 mg, 52%) as a clear glass. $\delta_H$ (DMSO-d$_6$) 8.30-8.21 (1H, m), 8.14-8.07 (1H, m), 7.99 (1H, d, J=7.66 Hz), 7.79-7.73 (2H, m), 7.37-7.31 (1H, m), 5.41-5.33 (1H, m), 4.62-4.48 (1H, m), 3.92-3.81 (1H, m), 3.20 (2H, s), 3.14 (3H, s), 2.71 (3H, d, J=4.35 Hz), 1.40 (3H, s), 3H under H$_2$O. LCMS (ES+) 415 (M+H)$^+$, 7.47 minutes (Method 7).

Example 74

(S)-2-(N'-{3-[1-(4-Amino-[1,3,5]triazin-2-ylamino)ethyl]-8-chloroquinolin-2-yl}-N'-methylamino)-N-methylacetamide Similarly, Intermediate 46 (65 mg, 0.21 mmol), 2-amino-4-chloro-[1,3,5]triazine (50 mg, 0.38 mmol) and DIPEA (1.0 mL, 4.56 mmol) in n-butanol (6 mL) at 150° C. afforded the title compound (32.4 mg, 39%) as a white solid. $\delta_H$ (DMSO-d$_6$) 8.26 (1H, s), 8.15-8.05 (1H, m), 7.99 (1H, d, J=8.67 Hz), 7.77 (2H, d, J=7.49 Hz), 7.38-7.30 (1H, m), 5.42-5.32 (1H, m), 4.55-4.39 (1H, m), 3.90-3.83 (1H, m), 3.20-3.11 (3H, m), 2.73-2.67 (3H, m), 1.49-1.39 (3H, m), 3H under H$_2$O. LCMS (ES+) 401 (M+H)$^+$, 7.56 minutes (Method 8).

Example 75

(S)-2-(N'-{8-Chloro-3-[1-(thieno[2,3-d]pyrimidin-4-ylamino)ethyl]quinolin-2-yl}-N'-methylamino)-N-methylacetamide Similarly, Intermediate 46 (50 mg, 0.16 mmol), 4-chlorothieno[2,3-d]pyrimidine (50 mg, 0.23 mmol) and DIPEA (1.0 mL, 4.56 mmol) in n-butanol (6 mL) at 160° C. afforded the title compound (7.5 mg, 11%) as a yellow solid. $\delta_H$ (DMSO-d$_6$) 8.45 (1H, d, J=6.69 Hz), 8.32 (1H, s), 8.29 (1H, s), 8.06 (1H, d, J=5.15 Hz), 7.88 (1H, d, J=5.99 Hz), 7.80-7.74 (2H, m), 7.67 (1H, d, J=5.98 Hz), 7.34-7.29 (1H, m), 5.72-5.67 (1H, m), 4.45 (1H, d, J=16.27 Hz), 3.96 (1H, d, J=16.32 Hz), 3.20 (3H, s), 2.69 (3H, d, J=4.62 Hz), 1.62 (3H, d, J=6.69 Hz). LCMS (ES+) 441 (M+H)$^+$, 3.12 minutes (Method 1).

Example 76

(S)-2-(N'-{8-Chloro-3-[1-(pyrrolo[2,1-j][1,2,4]triazin-4-ylamino)ethyl]quinolin-2-yl)-N'-methylamino)-N-methylacetamide Similarly, Intermediate 46 (50 mg, 0.16 mmol), 4-bromopyrrolo[2,1-f][1,2,4]-triazine (50 mg, 0.25 mmol) and DIPEA (1.0 mL, 4.56 mmol) in n-butanol (6 mL) at 160° C. afforded the title compound (17.8 mg, 26%) as a beige solid. $\delta_H$ (DMSO-d$_6$) 8.61 (1H, d, J=6.86 Hz), 8.19 (1H, s), 7.96 (1H, d, J=5.33 Hz), 7.74-7.64 (3H, m), 7.57 (1H, dd, J 2.62, 1.56 Hz), 7.24 (1H, t, J=7.80 Hz), 7.04 (1H, dd, J 4.37, 1.60 Hz), 6.60 (1H, dd, J 4.37, 2.60 Hz), 5.65-5.57 (1H, m), 4.31 (1H, d, J=16.27 Hz), 3.86 (1H, d, J=16.27 Hz), 3.08 (3H, s), 2.59 (3H, d, J=4.61 Hz), 1.53 (3H, d, J=6.70 Hz). LCMS (ES+) 424 (M+H)$^+$, 3.25 minutes (Method 1).

Example 77

(S)-2-(N'-{8-Chloro-3-[1-(pyrazolo[1,5-a]pyrimidin-7-ylamino)ethyl]quinolin-2-yl}-N'-methylamino)-N-methylacetamide Similarly, Intermediate 46 (50 mg, 0.16 mmol), 7-chloropyrazolo[1,5-a]-pyrimidine (50 mg, 0.32 mmol) and DIPEA (1.0 mL, 4.56 mmol) in n-butanol (6 mL) at 160° C. afforded the title compound (35.7 mg, 53%) as a brown glass. $\delta_H$ (DMSO-d$_6$) 8.59 (1H, s), 8.40-8.34 (1H, m), 8.14-8.05 (3H, m), 7.79-7.70 (2H, m), 7.34-7.28 (1H, m), 6.44 (1H, d, J=2.28 Hz), 6.35 (1H, d, J=5.26 Hz), 5.28-5.21 (1H, m), 4.14 (1H, d, J=15.88 Hz), 3.98 (1H, d, J 15.88), 3.17 (3H, s), 2.70 (3H, d, J=4.53 Hz), 1.87 (3H, d, J=6.62 Hz). LCMS (ES+) 424 (M+H)$^+$, 7.55 minutes (Method 8).

Example 78

(S)-2-(N'-{8-Chloro-3-[1-(pyrido[3,2-d]pyrimidin-4-ylamino)ethyl]quinolin-2-yl}-N'-methylamino)-N-methylacetamide Similarly, Intermediate 46 (50 mg, 0.16 mmol), 4-chloropyrido[3,2-d]pyrimidine (50 mg, 0.30 mmol) and DIPEA (1.0 mL, 4.56 mmol) in n-butanol (6 mL) at 160° C. afforded the title compound (38.8 mg, 56%) as a white solid. $\delta_H$ (DMSO-d$_6$) 9.00-8.93 (1H, m), 8.89 (1H, dd, J 4.26, 1.58 Hz), 8.46 (2H, s), 8.14 (1H, dd, J 8.46, 1.58 Hz), 8.08-8.04 (1H, m), 7.88 (1H, dd, J 8.47, 4.26 Hz), 7.75-7.69 (2H, m), 7.29 (1H, t, J=7.80 Hz), 5.80-5.69 (1H, m), 4.42 (1H, d, J=16.32 Hz), 3.92 (1H, d, J=16.32 Hz), 3.18 (3H, s), 2.67 (3H, d, J=4.64 Hz), 1.68 (3H, d, J=6.76 Hz). LCMS (ES+) 436 (M+H)$^+$, 2.98 minutes (Method 1).

Example 79

(S)-2-(N'-{3-[1-(2-Amino-9H-purin-6-ylamino) ethyl]-8-chloroquinolin-2-yl}-N'-methylamino)-N-methylacetamide Similarly, Intermediate 46 (50 mg, 0.16 mmol), 6-chloro-9H-purin-2-amine (50 mg, 0.30 mmol) and DIPEA (1.0 mL, 4.56 mmol) in n-butanol (6 mL) at 160° C. afforded the title compound (3.11 mg, 1%) as a brown glass. $\delta_H$ (DMSO-d$_6$) 12.13 (1H, s), 8.41-8.31 (1H, m), 8.14-8.10 (1H, m), 7.91 (1H, s), 7.75-7.67 (3H, m), 7.30 (1H, t, J=7.79 Hz), 5.70-5.54 (2H, m), 4.76 (1H, s), 3.87-3.75 (1H, m), 3.22-3.10 (3H, m), 2.69 (3H, d, J=4.63 Hz), 1.49 (3H, d, J=6.63 Hz), 1H under H$_2$O. LCMS (ES+) 440 (M+H)$^+$, 2.55 minutes (Method 1).

Example 80

(S)-8-Chloro-N-[2-(methylthio)ethyl]-3-[1-(9H-purin-6-ylamino)ethyl]quinolin-2-amine Similarly, Intermediate 47 (132 mg, 0.40 mmol), 6-chloropurine (62 mg, 0.40 mmol) and DIPEA (1.0 mL, 4.56 mmol) in n-butanol (5 mL) at 120° C. afforded the title compound (24.4 mg, 15%) as a brown glass. $\delta_H$ (DMSO-d$_6$) 8.33-8.15 (3H, m), 7.99 (1H, s), 7.67-7.59 (2H, m), 7.49-7.42 (1H, m), 7.16-7.10 (1H, m), 5.71-5.60 (1H, m), 3.90-3.79 (1H, m), 3.78-3.67 (1H, m), 2.87-2.79 (2H, m), 2.16 (3H, s), 1.64 (3H, d, J=6.73 Hz), 1H under H$_2$O. LCMS (ES+) 414 (M+H)$^+$, 3.06 minutes (Method 2).

Example 81

(S)—N$^2$-(1-{8-Chloro-2-[(1-methyl-1H-imidazol-4-yl)methylamino]quinolin-3-yl}ethyl)pyrazolo[1,5-a][1,3,5]triazine-2,4-diamine Similarly, Intermediate 48 (50 mg, 0.16 mmol), 2-(methylsulfonyl)pyrazolo[1,5-a][1,3,5]triazin-4-amine (50 mg, 0.23 mmol) and DIPEA (1.0 mL, 4.56 mmol) in n-butanol (6 mL) at 130° C. afforded the title compound (2.6 mg, 4%) as an off-white solid. $\delta_H$ (MeOD-d$_4$): 7.97 (1H, s), 7.79 (1H, d, J=2.04 Hz), 7.61 (2H, d, J 7.76 Hz), 7.38 (1H, s), 7.13 (1H, t, J 7.77 Hz), 6.98 (1H, s), 5.72 (1H, s), 5.42 (1H, m), 4.76 (1H, d, J=14.70 Hz), 4.62 (1H, d, J=14.74 Hz), 3.58 (3H, s), 1.67 (3H, d, J=6.81 Hz). LCMS (ES+) 448 (M+H)$^+$, 7.38 minutes (Method 8).

Example 82

(S)—N-(1-{8-Chloro-2-[(1-methyl-1H-imidazol-4-yl)methylamino]quinolin-3-yl}ethyl)thieno[2,3-d]pyrimidin-4-amine formate salt Similarly, Intermediate 48 (50 mg, 0.16 mmol), 4-chlorothieno[2,3-d]pyrimidine (50 mg, 0.29 mmol) and DIPEA (1.0 mL, 4.56 mmol) in n-butanol (6 mL) at 130° C. for 20 h afforded the title compound (13.4 mg, 19%) as a tan solid. $\delta_H$ (DMSO-d$_6$) 8.34-8.24 (2H, m), 8.18 (1H, s), 8.03 (1H, s), 7.75 (1H, d, J=6.00 Hz), 7.68 (2H, m), 7.63 (1H, d, J=5.97 Hz), 7.47 (1H, s), 7.37 (1H, t, J=5.06 Hz), 7.15 (1H, t, J=7.75 Hz), 7.02 (1H, s), 5.73-5.65 (1H, m), 4.60 (2H, d, J=4.89 Hz), 3.60 (3H, s), 1.66 (3H, d, J=6.75 Hz). LCMS (ES+) 450 (M+H)$^+$, 3.17 minutes (Method 1).

Example 83

(S)—N-(1-{8-chloro-2-[(1-methyl-1H-imidazol-4-yl)methylamino]quinolin-3-yl}ethyl)pyrido[3,2-d]pyrimidin-4-amine formate salt Similarly, Intermediate 48 (50 mg, 0.16 mmol), 4-chloropyrido[3,2-d]pyrimidine (50 mg, 0.30 mmol) and DIPEA (1.0 mL, 4.56 mmol) in n-butanol (6 mL) at 130° C. afforded the title compound (30.1 mg, 6%) as a tan solid. $\delta_H$ (DMF-d$_7$) 9.37 (1H, d, J=8.43 Hz), 9.26 (1H, dd, J 4.24, 1.56 Hz), 8.71 (2H, d, J=6.63 Hz), 8.54 (1H, dd, J 8.47, 1.57 Hz), 8.48 (1H, s), 8.27 (1H, dd, J 8.47, 4.24 Hz), 7.90-7.82 (2H, m), 7.54 (1H, t, J=7.75 Hz), 7.43 (1H, s), 6.14-6.05 (1H, m), 5.04-4.93 (2H, m), 3.98 (3H, s), 3.59 (1H, s), 2.12 (3H, d, J=6.78 Hz). LCMS (ES+) 445 (M+H)$^+$, 3.06 minutes (Method 1).

Example 84

(S)-7-Fluoro-8-methyl-3-[1-(9H-purin-6-ylamino) ethyl]-N-(tetrahydro-2H-pyran-4-yl)quinolin-2-amine A solution of Intermediate 16 (151 mg, 0.45 mmol), 4-aminotetrahydro-2H-pyran (325 mg, 3.22 mmol) and DIPEA (0.388 mL, 2.23 mmol) in NMP (4 mL) and isopropanol (4 mL) was heated under microwave irradiation at 160° C. for 2 h. After cooling, the mixture was dissolved in a 1:1 mixture of Et$_2$O and EtOAc (200 mL) and washed with saturated brine (3×50 mL). The organic layer was separated, dried (MgSO$_4$), filtered and concentrated in vacuo. Purification by column chromatography (SiO$_2$, 5% EtOAc in DCM) gave a colourless oil (27 mg, 15%). LCMS (ES+) 404 (M+H)$^+$. The colourless oil (27 mg, 0.067 mmol) was dissolved in DCM (3.5 mL) and TFA (0.345 mL) and the solution was stirred at r.t. for 1.5 h. The excess solvent was removed in vacuo and the residue obtained was basified with 0.4M NaOH (10 mL) and extracted with EtOAc (3×20 mL). The organic layer was separated, dried (MgSO$_4$), filtered and concentrated in vacuo to give a colourless residue (19 mg, 93%). LCMS (ES+) 304 (M+H)$^+$. This compound (19 mg, 0.062 mmol), 6-chloropurine (13.8 mg, 0.089 mmol), DIPEA (0.031 mL, 0.179 mmol) and n-butanol (1 mL) were combined and heated under microwave irradiation at 130° C. for 1 h. Purification by preparative HPLC gave the title compound (3.7 mg, 14%) as a white solid. $\delta_H$ (CDCl$_3$) 12.20 (1H, br s), 8.48 (1H, s), 7.95 (1H, s), 7.84 (1H, s), 7.41 (1H, dd, J 8.77, 6.25 Hz), 6.95 (1H, t, J=8.97 Hz), 6.54 (1H, s), 5.95 (1H, d, J=9.64 Hz) 5.88 (1H, br s), 4.42-4.30 (1H, m), 4.05-3.99 (1H, m), 3.95-3.89 (1H, m), 3.56 (2H, dtd, J 29.99, 11.44, 2.45 Hz), 2.50 (3H, s), 2.25 (1H, d, J=12.90 Hz), 1.90 (1H, d, J=12.99 Hz), 1.79 (3H, d, J=6.49 Hz), 1.70-1.55 (1H, m, masked by H$_2$O), 1.37-1.29 (1H, m). LCMS (ES+) 422 (M+H)$^+$, 2.66 minutes (Method 2).

Example 85

8-Chloro-N-(1-methoxyprop-2-yl)-3-[(S)-1-(9H-purin-6-ylamino)ethyl]quinolin-2-amine and 8-Chloro-N—[(R)-1-methoxyprop-2-yl]-3-[(S)-1-(9H-purin-6-ylamino)ethyl]quinolin-2-amine A solution of Intermediate 23 (200 mg, 0.59 mmol), 2-amino-1-methoxypropane (0.15 mL, 1.47 mmol) and DIPEA (0.5 mL, 2.23 mmol) in NMP (3 mL) was stirred at 140° C. for 20 h. The reaction mixture was diluted with water (20 mL) and extracted with Et$_2$O (100 mL). The organic layer was washed with water (20 mL) and brine (20 mL), separated, dried (MgSO$_4$), filtered and concentrated in vacuo to afford the required intermediate (300 mg). A solution of this compound (300 mg, 0.79 mmol) and HCl (2 mL, 4 mmol; 2.0M in Et$_2$O) in MeOH (2 mL) was stirred at r.t. over a weekend. The reaction mixture was concentrated in vacuo. The resulting material (250 mg, 0.59 mmol), 6-chloropurine (117 mg, 0.76 mmol) and DIPEA (0.28 mL, 1.52 mmol) in n-butanol (5.0 mL) were stirred at 120° C. overnight. The reaction mixture was concentrated in vacuo and the residue was partitioned between DCM (100 mL) and water (30 mL). The organic layer was dried (phase separation cartridge) and concentrated in vacuo. The residue was purified by preparative HPLC to give the title compounds (24 mg, 9%; and 23 mg, 9%) as white solids. $\delta_H$ (DMSO-d$_6$) 8.29 (1H, s), 8.18 (2H, s), 8.04 (1H, s), 7.66 (2H, t, J=6.80 Hz), 7.15 (1H, t, J=7.89 Hz), 7.10-7.00 (1H, m), 5.80-5.62 (1H, m), 4.66-4.60 (1H, m), 3.61-3.55 (1H, m), 2.11-2.10 (2H, m), 1.68 (3H, d, J=6.61 Hz), 1.09 (3H, d, J=6.63 Hz), 3H under solvent peak. LCMS (ES+) 412 (M+H)$^+$, 1.70 minutes (Method 2). $\delta_H$ (DMSO-d$_6$) 8.30-8.25 (1H, m), 8.19-8.14 (2H, m), 8.04 (1H, s), 7.71-7.63 (2H, m), 7.20-7.13 (1H, m), 5.80-5.65 (0.5H, m), 4.66-4.58 (1H, m), 3.03 (2H, s), 1.68 (3H, d, J=6.68 Hz), 1.29 (3H, d, J=6.69 Hz), 3H and 2 geminal protons under solvent peak. LCMS (ES+) 412 (M+H)$^+$, 1.70 minutes (Method 2).

Example 86

(R)-3-{8-Chloro-3-[(S)-1-(9H-purin-6-ylamino)ethyl]quinolin-2-ylamino}propane-1,2-diol A solution/suspension of Intermediate 58 (60 mg, 0.16 mmol), 6-bromopurine (49 mg, 0.25 mmol) and DIPEA (0.15 mL, 0.82 mmol) in n-butanol (2 mL) was heated at 130° C. under microwave irradiation for 3 h. The reaction mixture was concentrated in vacuo and purified by preparative HPLC to afford the title compound (10 mg, 15%) as a cream solid. $\delta_H$ (MeOD-d$_4$) 8.23 (1H, s), 8.02 (1H, s), 7.97 (1H, s), 7.54-7.48 (2H, m), 7.05 (1H, t, J=7.78 Hz), 5.75-5.60 (1H, m), 3.81-3.70 (3H, m), 3.47-3.32 (2H, m), 1.67 (3H, d, J=6.80 Hz). LCMS (ES+) 414, 416 (M+H)$^+$, 1.80 minutes (Method 2).

Example 87

(S)-3-{8-Chloro-3-[(S)-1-(9H-purin-6-ylamino)ethyl]quinolin-2-ylamino}propane-1,2-diol Similarly, Intermediate 59 (50 mg, 0.14 mmol), 6-bromopurine (41 mg, 0.20 mmol) and DIPEA (0.12 mL, 0.68 mmol) in n-butanol (2 mL) gave the title compound (14 mg, 25%) as a pale yellow solid. $\delta_H$ (MeOD-d$_4$) 8.32 (1H, s), 8.12 (1H, s), 8.07 (1H, s), 7.64-7.59 (2H, m), 7.16 (1H, t, J=7.78 Hz), 5.76 (1H, s), 3.93-3.81 (2H, m), 3.80-3.73 (1H, m), 3.58-3.47 (2H, m), 2.68 (1H, s), 1.76 (3H, d, J=6.78 Hz). LCMS (ES+) 414, 416 (M+H)$^+$, 9.70 minutes (Method 4).

Example 88

(R)-3-(8-Chloro-3-{(S)-1-[4-(methylamino)-[1,3,5]triazin-2-ylamino]ethyl}quinolin-2-ylamino)propane-1,2-diol Similarly, Intermediate 58 (60 mg, 0.16 mmol), 4-chloro-2-(methylamino)-[1,3,5]triazine (36 mg, 0.25 mmol) and DIPEA (0.15 mL, 0.82 mmol) in n-butanol (2 mL) gave the title compound (30 mg, 45%) as a white solid. $\delta_H$ (MeOD-d$_4$) 8.16-7.90 (1H, br s), 8.01 (1H, s), 7.64 (1H, d, J=7.6 Hz), 7.63 (1H, d, J=8.0 Hz), 7.19 (1H, t, J=7.8 Hz), 5.50-5.30 (1H, br s), 3.93-3.78 (3H, m), 3.60-3.43 (2H, m), 2.90-2.86 (3H, m), 1.58 (3H, d, J=6.8 Hz). LCMS (ES+) 404, 406 (M+H)$^+$, 2.40 minutes (Method 1).

Example 89

(S)—N$^6$-{1-[7-Fluoro-2-(2-methoxyethylamino)-8-methylquinolin-3-yl]ethyl}-9H-purine-2,6-diamine Similarly, Intermediate 60 (60 mg, 0.17 mmol), 6-chloro-9H-purin-2-amine (44 mg, 0.26 mmol) and DIPEA (0.15 mL, 0.86 mmol) in n-butanol (2 mL) gave the title compound (24 mg, 34%) as a cream solid. $\delta_H$ (MeOD-d$_4$) 7.98 (1H, s), 7.72 (1H, s), 7.51 (1H, dd, J 8.80, 6.33 Hz), 6.95 (1H, t, J=9.10 Hz), 5.73-5.65 (1H, m), 3.92-3.84 (1H, m), 3.79-3.63 (3H, m), 2.50 (3H, d, J=2.34 Hz), 1.74 (3H, d, J=6.81 Hz), 3H under solvent peak. LCMS (ES+) 411 (M+H)$^+$, 2.40 minutes (Method 4).

Example 90

(S)-2-{8-Chloro-3-[1-(9H-purin-6-ylamino)ethyl]quinolin-2-ylamino}-N-methyl-acetamide Similarly, Intermediate 61 (50 mg, 0.14 mmol), 6-bromopurine (41 mg, 0.21 mmol) and DIPEA (0.12 mL, 0.68 mmol) in n-butanol (2 mL) gave the title compound (14 mg, 25%) as a yellow solid. $\delta_H$ (MeOD-d$_4$) 8.26 (1H, s), 8.11 (1H, s), 8.02 (1H, s), 7.60-7.56 (2H, m), 7.11 (1H, t, J=7.78 Hz), 5.72-5.63 (1H, m), 4.28 (1H, d, J=16.08 Hz), 4.17 (1H, d, J=16.09 Hz), 2.74 (3H, s), 1.74 (3H, d, J=6.79 Hz). LCMS (ES+) 411 (M+H)$^+$, 2.43 minutes (Method 1).

Example 91

(S)-2-{8-Chloro-3-[1-(9H-purin-6-ylamino)ethyl]quinolin-2-ylamino}-N,N-dimethyl-acetamide Similarly, Intermediate 63 (60 mg, 0.16 mmol), 6-bromopurine (47 mg, 0.24 mmol) and DIPEA (0.14 mL, 0.79 mmol) in n-butanol (2 mL) gave the title compound (15.3 mg, 23%) as a yellow solid. $\delta_H$ (MeOD-d$_4$) 8.32 (1H, s), 8.10 (1H, s), 8.07 (1H, s), 7.61 (2H, d, J=8.0 Hz), 7.14 (1H, t, J=7.8 Hz), 5.90-5.80 (1H, m), 4.57 (1H, d, J=16.63 Hz), 4.34 (1H, d, J=16.58 Hz), 3.23 (3H, s), 2.99 (3H, s), 1.80 (3H, d, J=6.80 Hz). LCMS (ES+) 425 (M+H)$^+$, 2.67 minutes (Method 1).

Example 92

(S)-8-Chloro-3-[1-(9H-purin-6-ylamino)ethyl]-N-(pyridin-2-ylmethyl)quinolin-2-amine Similarly, Intermediate 64 (70 mg, 0.17 mmol), 6-bromopurine (49 mg, 0.25 mmol) and DIPEA (0.18 mL, 0.99 mmol) in n-butanol (2 mL) gave the title compound (10.8 mg, 21%) as a yellow solid. $\delta_H$ (MeOD-d$_4$) 8.38 (1H, d, J=5.04 Hz), 8.15 (1H, s), 8.10-8.05 (2H, m), 7.69-7.56 (3H, m), 7.51 (1H, d, J=7.89 Hz), 7.26-7.20 (1H, m), 7.12 (1H, t, J=7.78 Hz), 5.90-5.80 (1H, m), 5.02 (1H, d, J=15.57 Hz), 1.80 (3H, d, J=6.80 Hz), 1H under H$_2$O. LCMS (ES+) 431 (M+H)$^+$, 1.98 minutes (Method 2).

Example 93

(S)-2-({8-Chloro-3-[1-(9H-purin-6-ylamino)ethyl]quinolin-2-ylamino}methyl)pyridine 1-oxide Similarly, Intermediate 66 (50 mg, 0.11 mmol), 6-bromopurine (34 mg, 0.17 mmol) and DIPEA (0.12 mL, 0.68 mmol) in n-butanol (2 mL) gave the title compound (6.8 mg, 15%) as a yellow solid. $\delta_H$ (MeOD-$d_4$) 8.30-8.25 (2H, m), 8.06 (1H, s), 8.02 (1H, s), 7.70 (1H, d, J=7.75 Hz), 7.52 (2H, t, J=8.42 Hz), 7.41-7.33 (2H, m), 7.07 (1H, t, J=7.78 Hz), 5.85-5.50 (1H, m), 5.08 (1H, d, J=16.58 Hz), 4.96 (1H, d, J=16.57 Hz), 1.75 (3H, d, J=6.81 Hz). LCMS (ES+) 431, 433 (M+H)$^+$, 1.98 minutes (Method 2).

Example 94

(S)-2-{3-[1-(4-Aminopyrazolo[1,5-a][1,3,5]triazin-2-ylamino)ethyl]-8-chloroquinolin-2-ylamino}-N,N-dimethylacetamide Similarly, Intermediate 63 (60 mg, 0.16 mmol), 2-chloropyrazolo[1,5-a][1,3,5]-triazin-4-amine (50 mg, 0.24 mmol) and DIPEA (0.17 mL, 0.95 mmol) in n-butanol (2 mL) gave the title compound (8 mg, 12%) as a white solid. $\delta_H$ (MeOD-$d_4$) 7.95 (1H, s), 7.74 (1H, d, J=2.11 Hz), 7.55 (2H, d, J=7.75 Hz), 7.09 (1H, t, J=7.73 Hz), 5.79-5.75 (1H, m), 5.42-5.38 (1H, m), 4.54-4.39 (2H, m), 3.21 (3H, s), 2.96 (3H, s), 1.64 (3H, d, J=6.82 Hz). LCMS (ES+) 440 (M+H)$^+$, 2.96 minutes (Method 1).

Example 95

(S)-8-Chloro-3-[1-(9H-purin-6-ylamino)ethyl]-N-(pyridin-3-ylmethyl)quinolin-2-amine Similarly, Intermediate 65 (100 mg, 0.24 mmol), 6-bromopurine (72 mg, 0.36 mmol) and DIPEA (0.43 mL, 2.42 mmol) in n-butanol (3 mL) gave the title compound (7 mg, 7%) as a yellow solid. $\delta_H$ (MeOD-$d_4$) 8.60 (1H, s), 8.34-8.30 (1H, m), 8.19 (1H, s), 8.10 (1H, s), 7.89 (1H, s), 8.03 (1H, s), 7.93-7.90 (1H, m), 7.61-7.57 (2H, m), 7.29-7.23 (1H, m), 7.12 (1H, t, J=7.76 Hz), 5.88-5.74 (1H, m), 4.96 (1H, d, J=15 Hz), 4.76 (1H, d, J=14.68 Hz), 1.74 (3H, d, J=6.77 Hz). LCMS (ES+) 431 (M+H)$^+$, 2.01 minutes (Method 2).

Example 96

(S)—N$^2$-{1-[7-Fluoro-2-(2-methoxyethylamino)-8-methylquinolin-3-yl]ethyl}-6-methyl-[1,3,5]triazine-2,4-diamine Similarly, Intermediate 60 (65 mg, 0.23 mmol), 2-amino-4-chloro-6-methyl-[1,3,5]triazine (40 mg, 0.27 mmol) and DIPEA (100 mg, 0.78 mmol) in n-butanol (2 mL) gave the title compound (16 mg, 20%) as a white solid. $\delta_H$ (CDCl$_3$) 7.76 (1H, s), 7.38 (1H, dd, J 8.79, 6.25 Hz), 6.97-6.90 (1H, m), 6.00-5.93 (1H, m), 5.30 (1H, d, J=8.63 Hz), 4.10-4.02 (1H, m), 3.89-3.56 (4H, m), 3.66-3.21 (5H, m), 2.52 (3H, d, J=2.38 Hz), 2.31-2.18 (3H, m), 1.66-1.59 (3H, m). LCMS (ES+) 386 (M+H)$^+$, 2.56 minutes (Method 1).

Example 97

(S)—N,N-Diethyl-7-fluoro-8-methyl-3-[1-(9H-purin-6-ylamino)ethyl]quinolin-2-amine Similarly, Intermediate 19 (70 mg, 0.25 mmol), 6-bromopurine (42 mg, 0.27 mmol) and DIPEA (100 mg, 0.78 mmol) in n-butanol (2 mL) gave the title compound (22.2 mg, 22%) as a white solid. $\delta_H$ (CDCl$_3$) 8.37 (1H, s), 7.99 (2H, d, J=5.28 Hz), 7.44-7.36 (1H, m), 7.04 (1H, t, J=9.00 Hz), 6.60-6.53 (1H, m), 5.87-5.76 (1H, m), 3.61-3.41 (4H, m), 2.63 (1H, s), 2.60 (3H, d, J=2.38 Hz), 1.64 (3H, d, J=6.62 Hz), 1.23 (6H, t, J=6.96 Hz). LCMS (ES+) 394 (M+H)$^+$, 9.05 minutes (Method 8).

Example 98

(S)—N$^2$-{1-[7-Fluoro-2-(3-methoxypropylamino)-8-methylquinolin-3-yl]ethyl}-[1,3,5]-triazine-2,4-diamine A mixture of Intermediate 16 (280 mg, 0.83 mmol), 3-methoxypropylamine (98 mg, 1.1 mmol) and DIPEA (0.4 mL, 2.19 mmol) in n-butanol (2 mL) was heated at 120° C. for 5 days. The reaction mixture was cooled and partitioned between water (30 mL) and EtOAc (100 mL). The organic layer was washed with water (5×20 mL), separated, dried (MgSO$_4$) and concentrated in vacuo. The residue was then purified by column chromatography (SiO$_2$, 75-100% EtOAc in isohexane) to give an off-white solid. This was dissolved in 1,4-dioxane (10 mL) and treated with HCl (2 mL; 4.0M in 1,4-dioxane) and the mixture was stirred at r.t. overnight. The reaction mixture was concentrated in vacuo to give an orange oil (200 mg, 81%). A portion of this oil (70 mg, 0.25 mmol), 2-amino-4-chloro-[1,3,5]triazine (35 mg, 0.27 mmol) and DIPEA (100 mg, 0.78 mmol) in n-butanol (2 mL) was heated at 110° C. overnight. The solvent was removed in vacuo and the residue purified by preparative HPLC to give the title compound (31.5 mg, 34%) as a white solid. $\delta_H$ (CDCl$_3$) 7.72 (1H, s), 7.37 (1H, dd, J 8.76, 6.25 Hz), 6.93 (1H, t, J=8.99 Hz), 6.43 (1H, s), 5.56-5.06 (4H, m), 3.89-3.34 (5H, m), 3.34 (3H, s), 2.53 (3H, d, J=2.39 Hz), 2.03-1.92 (2H, m), 1.66 (3H, d, J=6.69 Hz). LCMS (ES+) 386 (M+H)$^+$, 2.20 minutes (Method 2).

Example 99

(S)-7-Fluoro-N-(3-methoxypropyl)-8-methyl-3-[1-(9H-purin-6-ylamino)ethyl]quinolin-2-amine A mixture of Intermediate 16 (280 mg, 0.83 mmol), 3-methoxypropylamine (98 mg, 1.1 mmol) and DIPEA (0.4 mL, 2.19 mmol) in n-butanol (2 mL) was heated at 120° C. for 5 days. The reaction mixture was cooled and partitioned between water (30 mL) and EtOAc (100 mL). The organic layer was washed with water (5×20 mL), separated, dried (MgSO$_4$) and concentrated in vacuo. The residue was then purified by column chromatography (SiO$_2$, 75-100% EtOAc in isohexane) to give an off-white solid. This was dissolved in 1,4-dioxane (10 mL) and treated with HCl (2 mL; 4.0M in 1,4-dioxane) and the mixture was stirred at r.t. overnight. The reaction mixture was concentrated in vacuo to give an orange oil (200 mg, 81%). A portion of this oil (70 mg, 0.25 mmol), 6-bromopurine (39 mg, 0.27 mmol) and DIPEA (100 mg, 0.78 mmol) in n-butanol (2 mL) was heated at 110° C. overnight. The solvent was removed in vacuo and the residue purified by preparative HPLC to give the title compound (17.2 mg, 18%) as a white solid. $\delta_H$ (CDCl$_3$) 8.47 (1H, s), 7.94 (1H, s), 7.81 (1H, s), 7.39 (1H, dd, J 8.81, 6.23 Hz), 6.96-6.89 (1H, m), 6.52 (1H, s), 6.00 (1H, d, J=9.12 Hz), 5.81 (1H, s), 3.71-3.58 (2H, m), 3.47-3.32 (2H, m), 3.24 (3H, s), 2.53 (3H, d, J=2.36 Hz), 2.02-1.82 (3H, m), 1.78 (3H, d, J=6.67 Hz). LCMS (ES+) 410 (M+H)$^+$, 2.30 minutes (Method 2).

Example 100

N-[(1,4-Dioxan-2-yl)methyl]-7-fluoro-3-[(S)-1-(9H-purin-6-ylamino)ethyl]quinolin-2-amine A mixture of Intermediate 15 (280 mg, 0.83 mmol), (1,4-dioxan-2-yl)-methanamine (117 mg, 1.0 mmol) and DIPEA (0.42 mL, 2.33 mmol) in n-butanol (2 mL) was heated at 120° C. for 3 days. The reaction mixture was cooled and partitioned between water (30 mL) and EtOAc (100 mL). The organic layer was washed with water (5×20 mL), separated, dried (MgSO$_4$) and concentrated in vacuo. The residue was purified by column chromatography (SiO$_2$, 75-100% EtOAc in isohexane) to give an off-white solid. This was dissolved in 1,4-dioxane (10 mL) and treated with HCl (2 mL; 4.0M in 1,4-dioxane) and the mixture was stirred at r.t. overnight. The reaction mixture was concentrated in vacuo to give a yellow oil (120 mg). A portion of this oil (60 mg, 0.19 mmol), 6-bromopurine (37 mg, 0.24 mmol) and DIPEA (100 mg, 0.78 mmol) in n-butanol (2 mL) was heated at 110° C. overnight. The solvent was removed in vacuo and the residue purified by preparative HPLC to give the title compound (5.2 mg, 7%) as a white solid. $\delta_H$ (CDCl$_3$) 8.50-8.45 (1H, m), 7.97-7.91 (1H, m), 7.88-7.86 (1H, m), 7.56 (1H, dd, J 8.83, 6.18 Hz), 6.99-6.93 (1H, m), 6.76-6.62 (1H, m), 6.33-6.23 (1H, m), 5.92-5.78 (1H, m), 3.86-3.24 (9H, m), 1.79 (3H, d, J=6.71 Hz), 2H under H$_2$O. LCMS (ES+) 424 (M+H)$^+$, 2.20 minutes (Method 1).

Example 101

N$^2$-[(S)-1-{2-[(1,4-Dioxan-2-yl)methylamino]-7-fluoroquinolin-3-yl}ethyl]-6-methyl-[1,3,5]triazine-2,4-diamine A mixture of Intermediate 15 (280 mg, 0.83 mmol), (1,4-dioxan-2-yl)-methanamine (117 mg, 1.0 mmol) and DIPEA (0.42 mL, 2.33 mmol) in n-butanol (2 mL) was heated at 120° C. for 3 days. The reaction mixture was cooled and partitioned between water (30 mL) and EtOAc (100 mL). The organic layer was washed with water (5×20 mL), dried (MgSO$_4$) and concentrated in vacuo. The residue was purified by column chromatography (SiO$_2$, 75-100% EtOAc in isohexane) to give an off-white solid. This was dissolved in 1,4-dioxane (10 mL) and treated with HCl (2 mL; 4.0M in 1,4-dioxane) and the mixture was stirred at r.t. overnight. The reaction mixture was concentrated in vacuo to give a yellow oil (120 mg). A portion of this oil (60 mg, 0.19 mmol), 2-amino-4-chloro-6-methyl-[1,3,5]triazine (35 mg, 0.24 mmol) and DIPEA (100 mg, 0.78 mmol) in n-butanol (2 mL) was heated at 110° C. overnight. The solvent was removed in vacuo and the residue purified by preparative HPLC to give the title compound (6 mg, 9%) as a white solid. $\delta_H$ (CDCl$_3$) 7.82-7.75 (1H, m), 7.53 (1H, dd, J 8.78, 6.26 Hz), 7.31-7.24 (2H, m), 7.18-7.07 (1H, m), 6.99-6.93 (1H, m), 6.21-6.09 (1H, m), 5.34-5.22 (2H, m), 4.02-3.49 (9H, m), 2.24 (3H, s), 1.67 (3H, d, J=6.71 Hz). LCMS (ES+) 414 (M+H)$^+$, 2.17 minutes (Method 1).

Example 102

(S)—N$^2$-{1-[7-Fluoro-2-(3-methoxypropylamino)quinolin-3-yl]ethyl}-6-methyl-[1,3,5]-triazine-2,4-diamine Similarly, Intermediate 18 (60 mg, 0.21 mmol), 2-amino-4-chloro-6-methyl-[1,3,5]triazine (35 mg, 0.24 mmol) and DIPEA (100 mg, 0.78 mmol) in n-butanol (2 mL) gave the title compound (18 mg, 22%) as a white solid. $\delta_H$ (CDCl$_3$) 7.74 (1H, s), 7.52 (1H, dd, J 8.78, 6.29 Hz), 7.31 (1H, dd, J 11.05, 2.55 Hz), 6.96-6.89 (1H, m), 6.49 (1H, s), 6.58-5.89 (3H, m), 5.40-5.20 (1H, m), 4.75 (1H, br s), 3.82-3.42 (4H, m), 3.36 (3H, s), 2.40-2.22 (3H, m), 1.98-1.90 (2H, m), 1.66 (3H, d, J=6.72 Hz). LCMS (ES+) 386 (M+H)$^+$, 6.64 minutes (Method 8).

Example 103

(S)-7-Fluoro-N-(3-methoxypropyl)-8-methyl-3-[1-(pyrazolo[1,5-a]pyrimidin-7-ylamino)ethyl]quinolin-2-amine A mixture of Intermediate 16 (280 mg, 0.83 mmol), 3-methoxypropylamine (98 mg, 1.1 mmol) and DIPEA (0.4 mL, 2.19 mmol) in n-butanol (2 mL) was heated at 120° C. for 5 days. The reaction mixture was cooled and partitioned between water (30 mL) and EtOAc (100 mL). The organic layer was washed with water (5×20 mL), dried (MgSO$_4$) and concentrated in vacuo. The residue was purified by column chromatography (SiO$_2$, 75-100% EtOAc in isohexane) to give an off-white solid. This was dissolved in 1,4-dioxane (10 mL) and treated with HCl (2 mL; 4.0M in 1,4-dioxane) and the mixture was stirred at r.t. overnight. The reaction mixture was concentrated in vacuo to give an orange oil (200 mg, 81%). A portion of this oil (70 mg, 0.25 mmol), 7-chloropyrazolo[1,5-a]-pyrimidine (38 mg, 0.25 mmol) and DIPEA (100 mg, 0.78 mmol) in n-butanol (2 mL) was heated at 110° C. overnight. The solvent was removed in vacuo and the residue purified by preparative HPLC to give the title compound (29 mg, 30%) as a white solid. $\delta_H$ (CDCl$_3$) 8.11 (1H, d, J=5.12 Hz), 8.05 (1H, d, J=2.32 Hz), 7.76 (1H, s), 7.34 (1H, dd, J 8.81, 6.23 Hz), 6.94 (1H, t, J=9.00 Hz), 6.66 (1H, d, J=5.60 Hz), 6.55 (1H, d, J=2.32 Hz), 5.74 (1H, d, J=5.14 Hz), 5.69 (1H, t, J=4.76 Hz), 4.80-4.70 (1H, m), 3.79 (2H, q, J=5.57 Hz), 3.59-3.53 (2H, m), 3.27 (3H, s), 2.56 (3H, d, J=2.40 Hz), 2.06-1.93 (2H, m), 1.79 (3H, d, J=6.70 Hz). LCMS (ES+) 409 (M+H)$^+$, 3.41 minutes (Method 1).

Example 104

(S)-7-Fluoro-N-(2-methoxyethyl)-8-methyl-3-[1-(pyrazolo[1,5-a]pyrimidin-7-ylamino)ethyl]quinolin-2-amine Similarly, Intermediate 60 (65 mg, 0.23 mmol), 7-chloropyrazolo[1,5-a]-pyrimidine (38 mg, 0.25 mmol) and DIPEA (100 mg, 0.78 mmol) in n-butanol (2 mL) gave the title compound (11 mg, 12%) as a white solid. $\delta_H$ (CDCl$_3$) 8.14 (1H, d, J=5.12 Hz), 8.05 (1H, d, J=2.32 Hz), 7.81 (1H, s), 7.38 (1H, dd, J 8.82, 6.20 Hz), 6.98 (1H, t, J=8.99 Hz), 6.63 (1H, d, J=5.77 Hz), 6.56 (1H, d, J=2.32 Hz), 5.80 (1H, d, J=5.15 Hz), 5.33-5.28 (1H, m), 4.86-4.77 (1H, m), 3.93-3.79 (2H, m), 3.64-3.60 (2H, m), 3.19 (3H, s), 2.55 (3H, d, J=2.40 Hz), 1.81 (3H, d, J=6.74 Hz). LCMS (ES+) 395 (M+H)$^+$, 3.28 minutes (Method 1).

Example 105

(S)—N$^2$-{1-[2-(Diethylamino)-7-fluoro-8-methylquinolin-3-yl]ethyl}-[1,3,5]triazine-2,4-diamine Similarly, Intermediate 19 (70 mg, 0.25 mmol), 2-amino-4-chloro-[1,3,5]triazine (35 mg, 0.27 mmol) and DIPEA (100 mg, 0.78 mmol) in n-butanol (2 mL) gave the title compound (19.5 mg, 21%) as a white solid. $\delta_H$ (CDCl$_3$) 8.13 (1H, s), 7.88 (1H, s), 7.45 (1H, dd, J 8.86, 6.14 Hz), 7.08 (1H, t, J=9.01 Hz), 5.75-5.62 (1H, m), 5.51-5.35 (1H, m), 5.00-4.85 (2H, m), 3.59-3.42 (2H, m), 3.44-3.33 (2H, m), 2.60 (3H, d, J=2.41 Hz), 1.49 (3H, d, J=6.50 Hz), 1.21 (6H, t, J=6.94 Hz). LCMS (ES+) 370 (M+H)$^+$, 3.20 minutes (Method 2).

Example 106

(S)—N$^2$-{1-[7-Fluoro-2-(3-methoxypropylamino)-8-methylquinolin-3-yl]ethyl}-6-methyl-[1,3,5]triazine-2,4-diamine A mixture of Intermediate 16 (280 mg, 0.83 mmol), 3-methoxypropylamine (98 mg, 1.1 mmol) and DIPEA (0.4 mL, 2.19 mmol) in n-butanol (2 mL) was heated at 120° C. for 5 days. The reaction mixture was cooled and partitioned between water (30 mL) and EtOAc (100 mL). The organic layer was washed with water (5×20 mL), separated, dried (MgSO$_4$) and concentrated in vacuo. The residue was then purified by column chromatography (SiO$_2$, 75-100% EtOAc in isohexane) to give an off-white solid. This was dissolved in 1,4-dioxane (10 mL) and treated with HCl (2 mL; 4.0M in 1,4-dioxane) and the mixture was stirred at r.t. overnight. The reaction mixture was concentrated in vacuo to give an orange oil (200 mg, 81%). A portion of this oil (70 mg, 0.25 mmol), 2-amino-4-chloro-6-methyl-[1,3,5]triazine (36 mg, 0.25 mmol) and DIPEA (100 mg, 0.78 mmol) in n-butanol (2 mL) was heated at 110° C. overnight. The solvent was removed in vacuo and the residue purified by preparative HPLC to give the title compound (19.8 mg, 21%) as a white solid. $\delta_H$ (CDCl$_3$) 7.71 (1H, s), 7.37 (1H, dd, J 8.76, 6.27 Hz), 6.93 (1H, t, J=8.99 Hz), 6.58-5.89 (3H, m), 5.54-4.82 (4H, m), 3.87-3.41 (4H, m), 3.34 (3H, br s), 2.53 (3H, d, J=2.38 Hz), 2.30-2.20 (3H, m), 1.70-1.63 (3H, m). LCMS (ES+) 400 (M+H)$^+$, 2.14 minutes (Method 2).

Example 107

(S)-1-(2-{8-Chloro-3-[1-(pyrido[3,2-d]pyrimidin-4-ylamino)ethyl]quinolin-2-ylamino}ethyl)imidazolidin-2-one A mixture of Intermediate 23 (1.0 g, 2.9 mmol), 1-(2-aminoethyl)imidazolidin-2-one (0.5 g, 3.9 mmol) and DIPEA (0.8 mL, 5.8 mmol) in n-butanol (10 mL) was heated at 120° C. for 72 h. After cooling, the reaction mixture was partitioned between Et$_2$O (200 mL) and water (100 mL). The organic layer was washed with water (3×100 mL) and brine (100 mL), separated, dried (MgSO$_4$), filtered and concentrated in vacuo. The residue was purified by column chromatography (SiO$_2$, 5% MeOH in DCM) to give a pale yellow solid. This was dissolved in DCM (20 mL), treated with TFA (5 mL) and stirred for 4 h at r.t. After quenching with 2M NaOH solution (30 mL), the organic layer was washed with water (3×10 mL), separated, dried (MgSO$_4$), filtered and concentrated in vacuo to give an orange oil (0.8 g, 82%). A portion of this oil (100 mg, 0.3 mmol), 4-chloropyrido[3,2-d]pyrimidine (55 mg, 0.33 mmol) and DIPEA (100 mg, 0.78 mmol) in n-butanol (2 mL) was heated at 120° C. for 18 h. The solvent was removed in vacuo and the residue was purified by preparative HPLC to give the title compound (70 mg, 48%) as a pale yellow solid. $\delta_H$ (CDCl$_3$) 8.70-8.66 (2H, m), 8.15-8.09 (1H, m), 7.90 (1H, s), 7.67 (1H, dd, J 8.48, 4.25 Hz), 7.62 (1H, dd, J 7.54, 1.39 Hz), 7.53-7.46 (1H, m), 7.33 (1H, d, J 9.01 Hz), 7.10 (1H, t, J 7.75 Hz), 6.74 (1H, s), 5.75-5.64 (1H, m), 4.55 (1H, s), 3.98-3.87 (1H, m), 3.76-3.65 (1H, m), 3.63-3.42 (4H, m), 3.29-3.13 (2H, m), 1.82 (3H, d, J=6.78 Hz). LCMS (ES+) 463 (M+H)$^+$, 2.98 minutes (Method 1).

Example 108

(S)-1-(2-{8-Chloro-3-[1-(pyrrolo[2,1-f][1,2,4]triazin-4-ylamino)ethyl]quinolin-2-ylamino}ethyl)imidazolidin-2-one A mixture of Intermediate 23 (1.0 g, 2.9 mmol), 1-(2-aminoethyl)imidazolidin-2-one (0.5 g, 3.9 mmol) and DIPEA (0.8 mL, 5.8 mmol) in n-butanol (10 mL) was heated at 120° C. for 72 h. After cooling, the reaction mixture was partitioned between Et$_2$O (200 mL) and water (100 mL). The organic layer was washed with water (3×100 mL) and brine (100 mL), separated, dried (MgSO$_4$), filtered and concentrated in vacuo. The residue was purified by column chromatography (SiO$_2$, 5% MeOH in DCM) to give a pale yellow solid. This was dissolved in DCM (20 mL), treated with TFA (5 mL) and stirred for 4 h at r.t. After quenching with 2M NaOH solution (30 mL), the organic layer was washed with water (3×10 mL), separated, dried (MgSO$_4$), filtered and concentrated in vacuo to give an orange oil (0.8 g, 82%). A portion of this oil (100 mg, 0.3 mmol), 4-bromopyrrolo[2,1-f][1,2,4]triazine (66 mg, 0.33 mmol) and DIPEA (100 mg, 0.78 mmol) in n-butanol (2 mL) was heated at 120° C. for 18 h. The solvent was removed in vacuo and the residue was purified by preparative HPLC to give the title compound (100 mg, 74%) as a white solid. $\delta_H$ (CDCl$_3$) 7.97 (1H, s), 7.89 (1H, s), 7.63 (1H, dd, J 7.56, 1.38 Hz), 7.55-7.52 (2H, m), 7.14-7.09 (1H, m), 6.89 (1H, dd, J 4.40, 1.54 Hz), 6.81 (1H, d, J=7.26 Hz), 6.61 (1H, dd, J 4.41, 2.61 Hz), 6.16 (1H, s), 5.57-5.52 (1H, m), 4.09-4.03 (1H, m), 3.86 (1H, s), 3.77 (1H, dd, J 16.66, 8.33 Hz), 3.64-3.35 (4H, m), 3.21-3.05 (2H, m), 1.79 (3H, d, J=6.81 Hz). LCMS (ES+) 451 (M+H)$^+$, 2.94 minutes (Method 1).

Example 109

(S)-1-(2-{3-[1-(2-Amino-9H-purin-6-ylamino)ethyl]-8-chloroquinolin-2-ylamino}ethyl)imidazolidin-2-one A mixture of Intermediate 23 (1.0 g, 2.9 mmol), 1-(2-aminoethyl)imidazolidin-2-one (0.5 g, 3.9 mmol) and DIPEA (0.8 mL, 5.8 mmol) in n-butanol (10 mL) was heated at 120° C. for 72 h. After cooling, the reaction mixture was partitioned between Et$_2$O (200 mL) and water (100 mL). The organic layer was washed with water (3×100 mL) and brine (100 mL), separated, dried (MgSO$_4$), filtered and concentrated in vacuo. The residue was purified by column chromatography (SiO$_2$, 5% MeOH in DCM) to give a pale yellow solid. This was dissolved in DCM (20 mL), treated with TFA (5 mL) and stirred for 4 h at r.t. After quenching with 2M NaOH solution (30 mL), the organic layer was washed with water (3×10 mL), separated, dried (MgSO$_4$), filtered and concentrated in vacuo to give an orange oil (0.8 g, 82%). A portion of this oil (100 mg, 0.3 mmol), 2-amino-6-chloropurine (56 mg, 0.33 mmol) and DIPEA (100 mg, 0.78 mmol) in n-butanol (2 mL) was heated at 120° C. for 18 h. The solvent was removed in vacuo and the residue was purified by preparative HPLC to give the title compound (41.8 mg, 35%) as a white solid. $\delta_H$ (MeOD-d$_4$) 7.96 (1H, s), 7.76 (1H, s), 7.59-7.53 (2H, m), 7.08 (1H, t, J 7.77 Hz), 5.70-5.64 (1H, m), 3.99-3.89 (1H, m), 3.82-3.48 (4H, m), 3.39-3.31 (2H, m), 3.16-3.07 (2H, m), 1.70-1.66 (3H, m). LCMS (ES+) 467 (M+H)+, 2.58 minutes (Method 1).

Example 110

(S)-1-(2-{8-Chloro-3-[1-(pyrazolo[1,5-a]pyrimidin-7-ylamino)ethyl]quinolin-2-ylamino}ethyl)imidazolidin-2-one A mixture of Intermediate 23 (1.0 g, 2.9 mmol), 1-(2-aminoethyl)imidazolidin-2-one (0.5 g, 3.9 mmol) and DIPEA (0.8 mL, 5.8 mmol) in n-butanol (10 mL) was heated at 120° C. for 72 h. After cooling, the reaction mixture was partitioned between Et$_2$O (200 mL) and water (100 mL). The organic layer was washed with water (3×100 mL) and brine (100 mL), separated, dried (MgSO$_4$), filtered and concentrated in vacuo. The residue was purified by column chromatography (SiO$_2$, 5% MeOH in DCM) to give a pale yellow solid. This was dissolved in DCM (20 mL), treated with TFA (5 mL) and stirred for 4 h at r.t. After quenching with 2M NaOH solution (30 mL), the organic layer was washed with water (3×10 mL), separated, dried (MgSO$_4$), filtered and concentrated in vacuo to give an orange oil (0.8 g, 82%). A portion of this oil (100 mg, 0.3 mmol), 7-chloropyrazolo[1,5-a]pyrimidine (50 mg, 0.33 mmol) and DIPEA (100 mg, 0.78 mmol) in n-butanol (2 mL) was heated at 120° C. for 18 h. The solvent was removed in vacuo and the residue was purified by preparative HPLC to give the title compound (57 mg, 42%) as a clear glass. $\delta_H$ (CDCl$_3$) 8.09 (1H, d, J=5.17 Hz), 8.04 (1H, d, J=2.33 Hz), 7.81 (1H, s), 7.63 (1H, dd, J 7.56, 1.36 Hz), 7.46 (1H, dd, J 7.98, 1.36 Hz), 7.14-7.04 (1H, m), 6.92 (1H, d, J=5.76 Hz), 6.53 (1H, d, J=2.32 Hz), 6.37 (1H, s), 5.80 (1H, d, J=5.21 Hz), 4.94-4.84 (1H, m), 4.59 (1H, s), 3.98-3.89 (1H, m), 3.86-3.77 (1H, m), 3.68-3.52 (4H, m), 3.38-3.24 (2H, m), 1.80 (3H, d, J=6.76 Hz). LCMS (ES+) 451 (M+H)+, 3.41 minutes (Method 1).

Example 111

(S)-1-(2-{8-Chloro-3-[1-(1-methyl-1H-pyrazolo[3,4-d]pyrimidin-4-ylamino)ethyl]-quinolin-2-ylamino}ethyl)imidazolidin-2-one A mixture of Intermediate 23 (1.0 g, 2.9 mmol), 1-(2-aminoethyl)imidazolidin-2-one (0.5 g, 3.9 mmol) and DIPEA (0.8 mL, 5.8 mmol) in n-butanol (10 mL) was heated at 120° C. for 72 h. After cooling, the reaction mixture was partitioned between Et$_2$O (200 mL) and water (100 mL). The organic layer was washed with water (3×100 mL) and brine (100 mL), separated, dried (MgSO$_4$), filtered and concentrated in vacuo. The residue was purified by column chromatography (SiO$_2$, 5% MeOH in DCM) to give a pale yellow solid. This was dissolved in DCM (20 mL), treated with TFA (5 mL) and stirred for 4 h at r.t. After quenching with 2M NaOH solution (30 mL), the organic layer was washed with water (3×10 mL), separated, dried (MgSO$_4$), filtered and concentrated in vacuo to give an orange oil (0.8 g, 82%). A portion of this oil (100 mg, 0.3 mmol), 4-chloro-1-methyl-1H-pyrazolo[3,4-d]pyrimidine (34 mg, 0.2 mmol) and DIPEA (100 mg, 0.78 mmol) in n-butanol (2 mL) was heated at 120° C. for 18 h. The solvent was removed in vacuo and the residue was purified by preparative HPLC to give the title compound (22 mg, 26%) as a white solid. $\delta_H$ (CDCl$_3$) 8.44 (1H, s), 8.19-8.10 (1H, m), 7.89 (1H, s), 7.62 (1H, dd, J 7.57, 1.35 Hz), 7.53 (1H, d, J=7.68 Hz), 7.13-7.08 (1H, m), 6.05-5.94 (1H, m), 5.51-5.43 (1H, m), 4.20-4.11 (1H, m), 4.02 (3H, s), 3.95-3.86 (2H, m), 3.59-3.50 (3H, m), 3.36-3.10 (1H, m), 3.23 (1H, s), 1.79 (3H, d, J=6.75 Hz). LCMS (ES+) 466 (M+H)+, 8.86 minutes (Method 9).

Example 112

(S)-1-(2-{7-Fluoro-3-[1-(pyrazolo[1,5-a]pyrimidin-7-ylamino)ethyl]quinolin-2-ylamino}ethyl)imidazolidin-2-one Intermediate 15 (324 mg, 1.0 mmol), 1-(2-aminoethyl)imidazolidin-2-one (260 mg, 2.0 mmol), DIPEA (270 mg, 2.0 mmol) and n-butanol (5.0 mL) were combined in a sealed tube and heated to 120° C. for 72 h. After cooling, the mixture was dissolved in a 1:1 mixture of Et$_2$O and EtOAc (200 mL) and washed with saturated brine (3×50 mL). The organic layer was dried (MgSO$_4$), filtered and concentrated in vacuo. Purification by column chromatography (SiO$_2$, 0-5% MeOH in DCM) gave a yellow solid (76 mg, 17%). This was dissolved in DCM (5 mL) and treated with TFA (1 mL) and the mixture stirred for 4 h at r.t. before being quenched with 2M NaOH solution (30 mL). The organic layer was washed with water (2×10 mL), dried (MgSO$_4$), filtered and concentrated in vacuo to give a pale orange gum (55 mg, 94%). This was combined with 7-chloropyrazolo[1,5-a]-pyrimidine (38 mg, 0.22 mmol) and DIPEA (100 mg, 0.78 mmol) in n-butanol (2 mL) and the mixture heated at 120° C. for 16 h. After cooling, the mixture was dissolved in a 1:1 mixture of Et$_2$O and EtOAc (100 mL) and washed with saturated brine (3×10 mL).

The organic layer was separated, dried (MgSO$_4$), filtered and concentrated in vacuo. Purification of the residue by preparative HPLC gave the title compound (6 mg, 7.8%) as a white solid. $\delta_H$ (MeOD-d$_4$) 8.16 (1H, d, J=2.32 Hz), 8.10 (1H, d, J=5.40 Hz), 7.95 (1H, s), 7.60 (1H, dd, J 8.85, 6.33 Hz), 7.31 (1H, dd, J 11.11, 2.53 Hz), 6.97 (1H, td, J 8.72, 2.56 Hz), 6.49 (1H, d, J=2.33 Hz), 5.93 (1H, d, J=5.43 Hz), 5.06 (1H, q, J=6.73 Hz), 4.00-3.90 (1H, m), 3.83-3.73 (1H, m), 3.72-3.52 (4H, m), 3.32-3.26 (2H, m), 1.78 (3H, d, J=6.74 Hz). LCMS (ES+) 435 (M+H)+, 8.93 minutes (Method 9).

Example 113

(S)-1-(2-{8-Chloro-3-[1-(pyrazolo[1,5-a][1,3,5]triazin-4-ylamino)ethyl]quinolin-2-ylamino}ethyl)imidazolidin-2-one A mixture of Intermediate 23 (1.0 g, 2.9 mmol), 1-(2-aminoethyl)imidazolidin-2-one (0.5 g, 3.9 mmol) and DIPEA (0.8 mL, 5.8 mmol) in n-butanol (10 mL) was heated at 120° C. for 72 h. After cooling, the reaction mixture was partitioned between Et$_2$O (200 mL) and water (100 mL). The organic layer was washed with water (3×100 mL) and brine (100 mL), separated, dried (MgSO$_4$), filtered and concentrated in vacuo. The residue was purified by column chromatography (SiO$_2$, 5% MeOH in DCM) to give a pale yellow solid. This was dissolved in DCM (20 mL), treated with TFA (5 mL) and stirred for 4 h at r.t. After quenching with 2M NaOH solution (30 mL), the organic layer was washed with water (3×10 mL), separated, dried (MgSO$_4$), filtered and concentrated in vacuo to give an orange oil (0.8 g, 82%). A portion of this oil (333 mg, 1.0 mmol), 4-chloro-2-(methylthio)pyrazolo[1,5-a][1,3,5]triazine (220 mg, 1.1 mmol), DIPEA (270 mg, 2.0 mmol) and n-butanol (5 mL) were combined in a sealed tube and heated to 120° C. for 16 h. After cooling, the mixture was dissolved in a 1:1 mixture of Et$_2$O and EtOAc (200 mL) and washed with saturated brine (3×50 mL). The organic layer was separated, dried (MgSO$_4$), filtered and concentrated in vacuo. Purification by column chromatography (SiO$_2$, 0-5% MeOH in DCM) gave a yellow solid (360 mg, 80%). This was dissolved in DCM (50 mL) and treated with MCPBA (480 mg, 1.2 mmol) and the mixture was stirred for 4 h at r.t. After quenching with 2M NaOH solution (30 mL), the organic layer was washed with water (2×10 mL), separated, dried (MgSO$_4$), filtered and concentrated in vacuo to give a pale yellow gum (300 mg, 94%). To a solution of this gum (150 mg, 0.27 mmol) in EtOH (5 mL) was added portionwise NaBH$_4$ (22 mg, 0.58 mmol). After 10 minutes, water (10 mL) was added and the reaction mixture was concentrated in vacuo. The residue was partitioned between DCM (30 mL) and water (10 mL). The organic layer was washed with water (2×10 mL) and brine (10 mL), separated, dried (MgSO$_4$), filtered and concentrated in vacuo. Purification of the residue by column chromatography (SiO$_2$, 0-5% MeOH in DCM) gave the title compound (24.6 mg, 20%) as an off-white solid. $\delta_H$ (CDCl$_3$) 8.22 (1H, s), 8.00-7.90 (2H, m), 7.63 (1H, dd, J 7.52, 1.43 Hz), 7.53 (1H, dd, J 7.93, 1.42 Hz), 7.43-7.36 (1H, m), 7.11 (1H, t, J=7.74 Hz), 6.69-6.59 (1H, m), 6.44 (1H, d, J=2.18 Hz), 5.60-5.51 (1H, m), 4.54 (1H, s), 3.89-3.72 (2H, m), 3.71-3.44 (4H, m), 3.35-3.24 (2H, m), 1.85 (3H, d, J=14.20 Hz). LCMS (ES+) 452 (M+H)$^+$, 9.08 minutes (Method 9).

Example 114

(S)-2-{8-Chloro-3-[1-(9H-purin-6-ylamino)ethyl]quinolin-2-ylamino}acetic acid

A solution of Intermediate 69 (60 mg, 0.11 mmol) in dry THF (5 mL) was treated with a solution of TBAF (0.57 mL, 0.57 mmol; 1.0M in THF) and the mixture heated at 50° C. for 24 h. The solvent was removed in vacuo and the residue was purified by preparative HPLC to afford the title compound (10.7 mg, 24%) as a white solid. $\delta_H$ (MeOD-d$_4$) 8.33-8.31 (1H, m), 8.10 (1H, s), 8.03 (1H, s), 7.51 (1H, dd, J 8.83, 6.22 Hz), 7.01-6.95 (1H, m), 5.81-5.75 (1H, m), 4.30 (1H, d, J=17.2 Hz), 4.21 (1H, d, J=17.2 Hz), 2.49 (3H, d, J=2.32 Hz), 1.78 (3H, d, J=6.80 Hz). LCMS (ES+) 396 (M+H)$^+$, 2.29 minutes (Method 2).

Example 115

N-Benzyl-N-{7-fluoro-8-methyl-3-[(S)-1-(pyrazolo[1,5-a]pyrimidin-7-ylamino)ethyl]-quinolin-2-yl}amine A mixture of Intermediate 70 (150 mg, 0.4 mmol), benzylamine (0.08 mL, 0.7 mmol), copper(I) iodide (12 mg, 0.06 mmol), potassium phosphate (170 mg, 0.8 mmol) and ethylene glycol (62 mg, 1 mmol) in isopropanol (2 mL) was degassed and heated at 90° C. overnight. The mixture was cooled to r.t. and extra benzylamine (0.05 mL, 0.4 mmol), copper(I) iodide (10 mg, 0.05 mmol) and ethylene glycol (62 mg, 1 mmol) were added. The mixture was degassed and heated at 90° C. overnight. The reaction mixture was cooled to r.t., diluted with EtOAc (2.0 mL) and water (10 mL) and stirred for 15 minutes. The aqueous layer was separated and extracted into EtOAc (10 mL) The combined organic layers were washed with water (3×5 mL), brine (5 mL), separated, dried (Na$_2$SO$_4$), filtered and concentrated in vacuo to give a brown oil. This was passed through a SiO$_2$ plug (0-50% EtOAc in hexane) and concentrated in vacuo. The clear residue was purified by preparative HPLC to give the title compound (12.5 mg, 7.5%) as a white foam. $\delta_H$ (DMSO-d$_6$) 8.49 (1H, dd, J 7.6, 0.5 Hz), 7.95 (1H, d, J=7.6 Hz), 7.87 (1H, s), 7.74 (1H, d, J=2.0 Hz), 7.57 (1H, t, J=5.8 Hz), 7.51 (1H dd, J 8.6, 6.6 Hz), 7.39 (2H, d, J=7.3 Hz), 7.26 (2H, m), 7.17 (1H, m), 6.97 (1H, t, J=9.1 Hz), 6.33 (1H, d, J=7.6 Hz), 5.82 (1H, dd, J 2.3, 0.8 Hz), 5.43 (1H, t, J=7.1 Hz), 4.75 (2H, d, J=5.6 Hz), 2.36 (3H, d, J=2.0 Hz), 1.54 (3H, d, J=6.6 Hz). LCMS (ES+) 427 (M+H)$^+$, 2.58 minutes.

Example 116

7-Fluoro-8-methyl-3-[(S)-1-(pyrazolo[1,5-a]pyrimidin-7-ylamino)ethyl]quinolin-2-ylamine Intermediate 70 (150 mg, 0.4 mmol), copper(I) iodide (15 mg, 0.08 mmol), Cs$_2$CO$_3$ (400 mg, 1.2 mmol) and trifluoroacetamide (100 mg, 0.9 mmol) were added to degassed acetonitrile (3 mL). trans-N,N'-Dimethylcyclohexane-1,2-diamine (4 drops) was added and the mixture heated at 90° C. overnight. The reaction mixture was cooled to r.t., diluted with EtOAc (15 mL) and washed with water (2×5 mL). The organics were separated, dried (Na$_2$SO$_4$), filtered and concentrated in vacuo to give a crude oil which was purified by preparative HPLC to give the title compound (7.4 mg, 5%) as an off-white solid. $\delta_H$ (DMSO-d$_6$) 8.49 (1H, m), 7.88 (2H, m), 7.75 (1H, d, J=2.0 Hz), 7.51 (1H, dd, J 8.3, 6.6 Hz), 6.98 (1H, t, J=9.1 Hz), 6.48 (2H, s), 6.33 (1H, d, J=7.6 Hz), 5.91 (1H, dd, J 2.3, 0.8 Hz), 5.31 (1H, t, J=7.1 Hz), 2.42 (3H, d, J=2.0 Hz), 1.50 (3H, d, J=6.8 Hz). LCMS (ES+) 337 (M+H)$^+$, 1.99 minutes.

The invention claimed is:
1. A compound of formula (I) or an N-oxide thereof, or a pharmaceutically acceptable salt thereof:

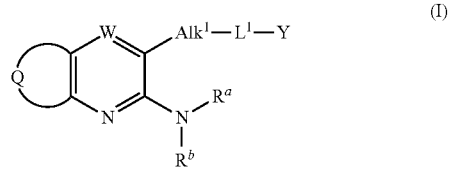

wherein
Q represents the residue of a phenyl ring optionally substituted with one or more substituents selected from the group consisting of $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$)alkylamino, halogen, cyano and trifluoromethyl;
W represents C—R$^1$;
Alk$^1$ represents a straight or branched $C_{1-3}$ alkylene chain optionally substituted with one or more substituents selected from the group consisting of trifluoromethyl, aryl, oxo, hydroxy, $C_{1-6}$ alkoxy, $C_{2-6}$ alkoxycarbonyl ($C_{1-6}$)alkoxy, aminocarbonyl($C_{1-6}$)alkoxy, trifluoromethoxy, aminocarbonyl, $C_{1-6}$ alkylaminocarbonyl and di($C_{1-6}$)alkylaminocarbonyl;
L$^1$ represents oxygen or N—R$^2$;
Y represents pyridopyrimidin-4-yl;
R$^1$ represents hydrogen, halogen, $C_{1-6}$ alkyl or $C_{1-6}$ alkoxy;
R$^2$ represents hydrogen or $C_{1-6}$ alkyl;
R$^a$ represents trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl ($C_{1-6}$)alkyl, heteroaryl or heteroaryl($C_{1-6}$)alkyl, any of which groups may be optionally substituted by one or more substituents selected from the group consisting of halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, amino, $C_{1-6}$ alkylamino, di($C_{1-6}$)-alkylamino, phenylamino, pyridinylamino, $C_{2-6}$ alkylcarbonylamino, $C_{2-6}$ alkoxycarbonyl-amino, and aminocarbonyl; and $R^b$ represents hydrogen, $C_{1-6}$ alkyl or $C_{3-7}$ cycloalkyl.

2. A compound as claimed in claim 1 represented by formula (IIA) or an N-oxide thereof, or a pharmaceutically acceptable salt thereof:

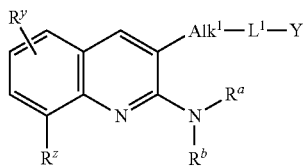

(IIA)

wherein $R^y$ and $R^z$ independently represent hydrogen, $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$)alkylamino, halogen, cyano or trifluoromethyl.

3. A compound as claimed in claim 2 wherein $R^y$ represents hydrogen.

4. A compound as claimed in claim 2 wherein $R^z$ represents $C_{1-6}$ alkyl.

5. A compound as claimed in claim 1 wherein $Alk^1$ represents (methyl)methylene.

6. A compound as claimed in claim 1 wherein $L^1$ represents $N\text{---}R^2$.

7. A compound as claimed in claim 1 wherein $R^b$ represents hydrogen or $C_{1-6}$ alkyl.

8. A pharmaceutical composition comprising a compound of formula (I) as defined in claim 1 or an N-oxide thereof, or a pharmaceutically acceptable salt thereof, in association with a pharmaceutically acceptable carrier.

* * * * *